United States Patent [19]
Adams et al.

[11] Patent Number: 5,656,644
[45] Date of Patent: Aug. 12, 1997

[54] PYRIDYL IMIDAZOLES

[75] Inventors: Jerry Leroy Adams, Wayne; Timothy Francis Gallagher, Harleysville; John C. Lee, Radnor; John Richard White, Coatesville, all of Pa.

[73] Assignee: SmithKline Beecham Corporation, Philadelphia, Pa.

[21] Appl. No.: 277,804

[22] Filed: Jul. 20, 1994

[51] Int. Cl.$^6$ .................... C07D 401/04; A61K 31/44
[52] U.S. Cl. .................. 514/341; 514/235.8; 514/306; 514/314; 514/397; 514/394; 546/274.1; 546/138; 546/167; 546/139; 546/269.1; 544/333; 544/360; 544/124; 548/313.4; 548/306.1
[58] Field of Search .................. 546/278, 269.1, 546/274.1, 138, 167, 139; 514/341, 235.8, 306, 314, 397, 394; 544/333, 124, 360; 548/313.4, 306.1

[56] References Cited

U.S. PATENT DOCUMENTS

| | | | |
|---|---|---|---|
| 3,707,475 | 12/1972 | Lombardino | 548/313.4 |
| 3,772,441 | 11/1973 | Lombardino | 548/313.4 |
| 3,929,807 | 12/1975 | Fitzi | 548/313.4 |
| 3,940,486 | 2/1976 | Fitzi | 548/313.4 |
| 4,175,127 | 11/1979 | Bender et al. | 546/271 |

FOREIGN PATENT DOCUMENTS

| | | |
|---|---|---|
| 0 011 111 | 5/1980 | European Pat. Off. . |
| 2221546 | 11/1972 | Germany . |

*Primary Examiner*—Jane Fan
*Attorney, Agent, or Firm*—Dara L. Dinner; Stephen Venetianer; Edward T. Lentz

[57] ABSTRACT

Novel 2,4,5-triaryl imidazole compounds and compositions for use in therapy.

13 Claims, No Drawings

PYRIDYL IMIDAZOLES

This invention relates to a novel group of imidazole compounds, processes for the preparation thereof, the use thereof in treating cytokine mediated diseases and pharmaceutical compositions for use in such therapy.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxermia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections; fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et al., Proc. Natl. Acad. Sci., 87:782–784 (1990)], therefore, inhibition of monokine production or activity aids in Biting HIV progression as stated above for T-cells.

TNF has also been implicated in various roles with other viral infections, such as the cytomegalia virus (CMV), influenza virus, and the herpes virus for similar reasons as those noted.

Interleukin-8 (IL-8) is a chemotactic factor first identified and characterized in 1987. IL-8 is produced by several cell types including mononuclear cells, fibroblasts, endothelial cells, and ketainocytes. Its production from endothelidl cells is induced by IL-1, TNF, or lipopolysachharide CLPS). Human IL-8 has been shown to act on Mouse, Guinea Pig, Rat, and Rabbit Neutrophils. Many different names have been applied to IL-8, such as neutophil attractant/activation protein-1 (NAP-1), monocyte derived neutrophil chemotactic factor (MDNCP), neutophil activating factor (NAF), and T-cell lymphocyte chemotactic factor.

IL-8 stimulates a number of functions in vitro. It has been shown to have chemoattractant properties for neutophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized with massive neutrophil infiltration. Conditions associated with an increased in IL-8 production (which is responsible for chemotaxis of neutrophils into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are cytokine suppressive anti-inflammatory drugs, i.e. compounds which are capable of inhibiting cytokines, such as IL-1, IL-6, IL-8 and TNF.

SUMMARY OF THE INVENTION

This invention relates to the novel compounds of Formula (I) and pharmaceutical compositions comprising a compound of Formula (I) and a pharmaceutically acceptable diluent or carrier.

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides a compound of formula (I):

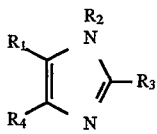

wherein:

$R_1$ is 4-pyridyl, pyrimidinyl, quinazolin-4-yl, quinolyl, isoquinolinyl, 1-imidazolyl or 1-benzimidazolyl which is optionally substituted with one or two substituents each of which is independently selected from $C_{1-4}$ alkyl, halogen, $C_{1-4}$ alkoxy, $C_{1-4}$ alkylthio, $NH_2$, mono- or di-$C_{1-6}$-alkylamino or N-heterocyclyl ring which ring has from 5 to 7 members and optionally contains an additional heteroatom selected from oxygen, sulfur or $NR_{22}$;

$R_2$ is hydrogen, $C_{1-10}$ alkyl $N_3$, $-(CR_{10}R_{20})_n$ $OR_{12}$, heterocyclyl, heterocyclyl$C_{1-10}$ alkyl, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$alkyl, $C_{5-7}$ cycloalkenyl, aryl, aryl$C_{1-10}$ alkyl, heteroaryl, heteroaryl$C_{1-10}$ alkyl, $(CR_{10}R_{20})_n$'$OR_{13}$, $(CR_{10}R_{20})_n$'$S(O)_mR_{25}$, $(CR_{10}R_{20})_n$'$NHS(O)_2R_{25}$, $(CR_{10}R_{20})_n$'$NR_8R_9$, $(CR_{10}R_{20})_n$'$NO_2$, $(CR_{10}R_{20})_n$'$CN$, $(CR_{10}R_{20})_n$'$SO_2R_{25}$, $(CR_{10}R_{20})_n$'$S(O)_mNR_8R_9$, $(CR_{10}R_{20})_n$'$C(Z)R_{13}$, $(CR_{10}R_{20})_n$'$C(Z)OR_{13}$, $(CR_{10}R_{20})_n$'$C(Z)NR_8R_9$, $(CR_{10}R_{20})_n$'$C(Z)NR_{13}OR_{12}$, $(CR_{10}R_{20})_n$'$NR_{10}C(Z)R_{13}$, $(CR_{10}R_{20})_n$'$NR_{10}C(Z)NR_8R_9$, $(CR_{10}R_{20})_n$'$N(OR_{21})C(Z)NR_8R_9$, $(CR_{10}R_{20})_n$'$N(OR_{21})C(Z)R_{13}$, $(CR_{10}R_{20})_n$'$C(=NOR_{21})R_{13}$, $(CR_{10}R_{20})_n$'$NR_{10}C(=NR_{27})NR_8R_9$, $(CR_{10}R_{20})_n$'$OC(Z)NR_8R_9$, $(CR_{10}R_{20})_n$'$NR_{10}C(Z)NR_8R_9$, $(CR_{10}R_{20})_n$'$NR_{10}C(Z)OR_{10}$, 5-($R_{25}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroarylalkyl, heterocyclyl, or heterocyclylalkyl moieties may be optionally substituted;

n' is an integer having a value of 1 to 10;

m is 0, or the integer 1 or 2;

$R_3$ is $-X_aP(Z)(X_bR_{13})_2$ or $Q-(Y_1)_t$;

Q is an aryl or heteroaryl group;

t is a number having a value of 1, 2 or 3;

$X_a$ is $-NR_8-$, $-O-$, $-S-$ or a $C_{1-10}$ alkylene chain optionally substituted by $C_{1-4}$ alkyl and optionally interrupted by $-NR_8-$, $-O-$ or $-S-$;

$X_b$ is $-(CR_{10}R_{20})_n$, $-NR_8-$, $-O-$ or $-S-$;

Z is oxygen or sulfur;

n is 0 or an integer from 1 to 10;

$Y_1$ is independently selected from hydrogen, $C_{1-5}$ alkyl, halo-substituted $C_{1-5}$ alkyl, halogen, $-X_a-P(Z)-(X_bR_{13})_2$ or $-(CR_{10}R_{20})_nY_2$;

$Y_2$ is $-OR_8$, $-NO_2$, $-S(O)_m"R_{11}$, $-SR_8$, $-S(O)_m"OR_8$, $-S(O)_mNR_8R_9$, $-NR_8R_9$, $-O(CR_{10}R_{20})_n$ '$NR_8R_9$, $-C(O)R_8$, $-CO_2R_8$, $-CO_2(CR_{10}R_{20})_n$ '$CONR_8R_9$, $-ZC(O)R_8$, $-CN$, $-C(Z)NR_8R_9$, $-NR_{10}C(Z)R_8$, $-C(Z)NR_8OR_9$, $-NR_{10}C(Z)NR_8R_9$, $-NR_{10}S(O)_m"R_{11}$, $-N(OR_{21})C(Z)NR_8R_9$, $-N(OR_{21})C(Z)R_8$, $-C(=NOR_{21})R_8$, $-NR_{10}C(=NR_{15})SR_{11}$, $-NR_{10}C(=NR_{15})NR_8R_9$, $-NR_{10}C(=CR_{14}R_{24})SR_{11}$, $-NR_{10}C(=CR_{14}R_{24})NR_8R_9$, $-NR_{10}C(O)C(O)NR_8R_9$, $-NR_{10}C(O)C(O)OR_{10}$, $-C(=NR_{13})NR_8R_9$, $-C(=NOR_{13})NR_8R_9$, $-C(=NR_{13})ZR_{11}$, $-OC(Z)NR_8R_9$, $-NR_{10}S(O)_m"CF_3$, $-NR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl;

m' is a number having it value of 1 or 2;

$R_4$ is phenyl, naphth-1-yl or naphth-2-yl which is optionally substituted by one or two substituents, each of which is independently selected, and which, for a 4-phenyl, 4-naphth-1-yl or 5-naphth-2-yl substituent, is halo, cyano, $-C(Z)NR_7R_{17}$, $-C(Z)OR_{23}$, $-(CR_{10}R_{20})_m"'COR_{36}$, $SR_5$, $-SOR_5$, $-OR_{36}$, halo-substituted-$C_{1-4}$ alkyl, $C_{1-4}$ alkyl, $-ZC(Z)R_{36}$, $-NR_{10}C(Z)R_{23}$, or $-(CR_{10}R_{20})_m"'NR_{10}R_{20}$ and which, for other positions of substitution, is halo, cyano, $-C(Z)NR_{16}R_{26}$, $-C(Z)OR_8$, $-(CR_{10}R_{20})_m"COR_8$, $-S(O)_mR_8$, $-OR_8$, halo-substituted-$C_{1-4}$ alkyl, $-C_{1-4}$ alkyl, $-(CR_{10}R_{20})_m"'NR_{10}C(Z)R_8$, $-NR_{10}S(O)_m"R_{11}$, $-NR_{10}S(O)_m"NR_7R_{17}$ $-ZC(Z)R_8$ or $-(CR_{10}R_{20})_m"'NR_{16}R_{26}$; wherein m" is 0 to 5 and m'" is 0 or 1;

$R_5$ is hydrogen, $C_{1-4}$ alkyl, $C_{2-4}$ alkenyl, $C_{2-4}$ alkynyl or $NR_7R_{17}$, excluding the moieties $-SR_5$ being $-SNR_7R_{17}$ and $-SOR_5$ being $-SOH$;

$R_6$ is $C_{1-4}$ alkyl, halo-substituted-$C_{1-4}$ alkyl, $C_{2-4}$ alkenyl, $C_{2-4}$ alkynyl or $C_{3-5}$ cycloalkyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{22}$;

$R_8$ is hydrogen, heterocyclyl, heterocyclylalkyl or $R_{11}$;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl: aryl, arylalkyl, heteroaryl or heteroarylalkyl or $R_8$ and $R_9$ may together with the nitrogen to which they are attached form a heterocyclic ring of 5 to 7 members which ring optionally contains an additional heteroatom selected from oxygen, sulfur or $NR_{12}$;

$R_{10}$ and $R_{20}$ is each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{12}$ is hydrogen, $-C(Z)R_{13}$ or optionally substituted $C_{1-4}$ alkyl, optionally substituted aryl, optionally substituted aryl$C_{1-4}$ alkyl, or $S(O)_2R_{25}$;

$R_{13}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl $C_{1-10}$ alkyl;

$R_{14}$ and $R_{24}$ is each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{12}$;

$R_{18}$ and $R_{19}$ is each independently selected from hydrogen, $C_{1-4}$ alkyl, substituted alkyl, optionally substituted aryl, optionally substituted arylalkyl or together denote a oxygen or sulfur;

$R_{21}$ is hydrogen, a pharmaceutically acceptable cation, $C_{1-10}$ alkyl, $C_{3-7}$ cycloalkyl, aryl, aryl $C_{1-4}$ alkyl, heteroaryl, heteroarylalkyl, heterocyclyl, aroyl, or $C_{1-10}$ alkanoyl;

$R_{22}$ is $R_{10}$ or C(Z)-$C_{1-4}$ alkyl;

$R_{23}$ is $C_{1-4}$ alkyl, halo-substituted-$C_{1-4}$ alkyl, or $C_{3-5}$ cycloalkyl;

$R_{36}$ is hydrogen or $R_{23}$;

$R_{25}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl;

$R_{27}$ is hydrogen, cyano, $C_{1-4}$ alkyl, $C_{3-7}$ cycloalkyl, or aryl;

or a pharmaceutically acceptable salt thereof; and excluding 2-(4-chlorophenyl)-4-(4-methoxyphenyl)-5-(4-pyridyl)imidazole, and 2-phenyl-4-phenyl-5-(4-pyridyl)imidazole.

FULL DESCRIPTION OF THE INVENTION

The novel compounds of Formula (I) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retovirus infections, such as but not limited to feline immunodeficiency virus (FIV), bovine immunodeficiency virus, or canine immunodeficiency virus or other retroviral infections.

In Formula (I), suitable $R_1$ moieties includes 4-pyridyl, 4-pyrimidinyl, 4-quinolyl, 6-isoquinolinyl, quinazolin-4-yl, 1-imidazolyl and 1-benzimidazolyl, of which 4-pyridyl, 4-pyrimidinyl and 4-quinolyl, are preferred. More preferably $R_1$ is a 4-pyridyl or 4-pyrimidinyl group. A preferred substituent for all $R_1$ moieties is $C_{1-4}$ alkyl, in particular methyl, and $NR_{10}R_{20}$, preferably where $R_{10}$ and $R_{20}$ are hydrogen or methyl, more preferably $R_{10}$ and $R_{20}$ are hydrogen. A more preferred substituent is the $NR_{10}R_{20}$ moiety. Preferred ring placement of the $R_1$ substituent on the 4-pyridyl derivative is the 2-position, such as 2-methyl-4-pyridyl. Preferred ring placement on the 4-pyrimidinyl is also at the 2-position, such as 2-methyl-pyrimidine or 2-amino-pyrimidine.

Suitably, $R_2$ is hydrogen, $-(CR_{10}R_{20})_n$ $OR_{12}$, heterocyclyl, heterocyclyl$C_{1-10}$ alkyl, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-4}$ alkyl, $C_{5-7}$ cycloalkenyl, aryl, aryl$C_{1-10}$ alkyl, heteroaryl, heteroaryl$C_{1-10}$ alkyl, $(CR_{10}R_{20})_n$'$OR_{13}$, $(CR_{10}R_{20})_n$'S(O)$_m$$R_{25}$, $(CR_{10}R_{20})_n$'NHS(O)$_2$$R_{25}$, $(CR_{10}R_{20})_n$'$NR_8R_9$, $(CR_{10}R_{20})_n$'$NO_2$, $(CR_{10}R_{20})_n$'CN, $(CR_{10}R_{20})_n$'$SO_2R_{25}$, $(CR_{10}R_{20})_n$'S(O)$_m$$NR_8R_9$, $(CR_{10}R_{20})_n$'C(Z)$R_{13}$, $(CR_{10}R_{20})_n$'C(Z)$OR_{13}$, $(CR_{10}R_{20})_n$'C(Z)$NR_8R_9$, $(CR_{10}R_{20})_n$'C(Z)$NR_{13}OR_{12}$, $(CR_{10}R_{20})_n$'$NR_{10}$C(Z)$R_{13}$, $(CR_{10}R_{20})_n$'$NR_{10}$C(Z)$NR_8R_9$, $(CR_{10}R_{20})_n$'N(OR$_{21}$)C(Z)$NR_8R_9$, $(CR_{10}R_{20})_n$'N(OR$_{21}$)C(Z)$R_{13}$, $(CR_{10}R_{20})_n$'C(=NOR$_{21}$)$R_{13}$, $(CR_{10}R_{20})_n$'$NR_{10}$C(=NR$_{27}$)$NR_8R_9$, $(CR_{10}R_{20})_n$'OC(Z)$NR_8R_9$, $(CR_{10}R_{20})_n$'$NR_{10}$C(Z)$NR_8R_9$, $(CR_{10}R_{20})_n$'$NR_{10}$C(Z)$OR_{10}$, 5-($R_{25}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroarylalkyl, heterocyclyl, or heterocyclylalkyl moieties may be optionally substituted.

Preferably $R_2$ is hydrogen, an optionally substituted heterocyclyl ring, and optionally substituted heterocyclyl$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{20})_n$'C(Z)$OR_{13}$ group, $(CR_{10}R_{20})_n$'$NR_8R_9$, $(CR_{10}R_{20})_n$'NHS(O)$_2$$R_{25}$, $(CR_{10}R_{20})_n$'S(O)$_m$$R_{25}$, an optionally substituted aryl; an optionally substituted aryl$C_{1-10}$ alkyl, $(CR_{10}R_{20})_n$'$OR_{13}$, $(CR_{10}R_{20})_n$'C(Z)$R_{13}$, or $(CR_{10}R_{20})_n$'C(=NOR$_{21}$)$R_{13}$.

More preferably $R_2$ is an optionally substituted $C_{1-10}$ alkyl, an optionally substituted heterocyclyl ring, an optionally substituted heterocyclyl$C_{1-10}$ alkyl, an optionally substituted aryl, $(CR_{10}R_{20})_n$'$NR_8R_9$, or $(CR_{10}R_{20})_n$'C(Z)$OR_{13}$ group.

When $R_2$ is an optionally substituted heterocyclyl the ring is preferably a morpholino, pyrrolidinyl, or a piperidinyl group. When the ring is optionally substituted the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl— wherein the aryl or aryl alkyl moieties themselves may be optionally substituted (as in the definition section below); C(O)$OR_{13}$, such as the C(O)$C_{1-4}$ alkyl or C(O)OH moieties; C(O)H; C(O)$C_{1-4}$ alkyl, hydroxy substituted $C_{1-4}$ alkyl, $C_{1-4}$ alkoxy, S(O)$_m$$C_{1-4}$ alkyl (wherein m is 0, 1, or 2), $NR_{10}R_{20}$ (wherein $R_{10}$ and $R_{20}$ are independently hydrogen or $C_{1-4}$alkyl).

Preferably if the ring is a piperidine, the ring is attached to the imidazole at the 4-position, and the substituents are directly on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2 or 6 position or both, such as 2,2,6,6-tetramethyl-4-piperidine. Similarly, if the ring is a pyrrole, the ring is attached to the imidazole at the 3-position, and the substituents are also directly on the available nitrogen.

When $R_2$ is an optionally substituted heterocyclyl $C_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrollidinyl propyl, and piperidinyl propyl moieties. The heterocyclic ring herein is also optionally substituted in a similar manner to that indicated above for the direct attachment of the heterocyclyl.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_5$ to $C_6$ ring which ring may be optionally substituted one or more times independently by halogen, such as fluorine, chlorine, bromine or iodine; hydroxy; $C_{1-10}$ alkoxy, such as methoxy or ethoxy; $S(O)_m$ alkyl, wherein m is 0, 1, or 2, such as methyl thio, methylsulfinyl or methyl sulfonyl; amino, mono & di-substituted amino, such as in the $NR_7R_{17}$ group; or where the $R_7R_{17}$ may cyclize together with the nitrogen to which they are attached to form a 5 to 7 membered ring which optionally includes an additional heteroatom selected from O/N/S; $C_{1-10}$ alkyl, such as methyl, ethyl, propyl, isopropyl, or t-butyl; halosubstituted alkyl, such as $CF_3$; hydroxy substituted $C_{1-10}$alkyl; $C(O)OR_{13}$, such as the free acid or methyl ester derivative; an optionally substituted aryl, such as phenyl; an optionally substituted arylalkyl, such as benzyl or phenethyl; and further where these aryl or aryl alkyl moieties may also be substituted one to two times by halogen; hydroxy; $C_{1-10}$ alkoxy; $S(O)_m$ alkyl; amino, mono & di-substituted amino, such as in the $NR_7R_{17}$ group; alkyl or halosubstituted alkyl.

When $R_2$ is $(CR_{10}R_{20})_n NR_8R_9$, $R_8$ and $R_9$ are as defined in Formula (I), preferably $R_8$ and $R_9$ are each independently selected from hydrogen, optionally substituted $C_{1-4}$ alkyl, optionally substituted aryl or an optionally substituted aryl$C_{1-4}$ alkyl, or together with the nitrogen which they are attached form a heterocyclic ring of 5 to 7 members which ring optionally contains an additional heteroatom selected from oxygen, sulfur or $NR_{12}$. It is recognized that in some instances this can yield the same moiety as a heterocyclic $C_{1-10}$ alkyl moiety noted above which is also a suitable $R_2$ variable. Preferably $R_8$ and $R_9$ are independently hydrogen, $C_{1-4}$ alkyl, preferably methyl, or benzyl. The n term is preferably 1 to 4, more preferably 3 or 4, and most preferably 3, such as in a propyl group. Preferred groups include, but ate not limited to, aminopropyl, (N-methyl-N-benzyl) aminopropyl, (N-Phenylmethyl)amino-1-propyl, or diethylamino propyl.

When $R_2$ is a $(CR_{10}R_{20})_n'C(Z)OR_{13}$ group, $R_{13}$ is suitably hydrogen, $C_{1-4}$ alkyl, especially methyl. The n' term is preferably 1 to 4, more preferably 2 or 3, such as in an ethyl or propyl group. Preferred groups include, but are not limited to, carboxymethyl-1-butyl, carboxy-1-propyl, or 2-acetoxyethyl.

When $R_2$ is a $(CR_{10}R_{20})_n'S(O)_m R_{25}$ group m is 0, 1, or 2, and $R_{18}$ is preferably aryl, especially phenyl, or $C_{1-10}$ alkyl, especially methyl. The n term is preferably 1 to 4, more preferably 2 or 3, such as in an ethyl or propyl group.

When $R_2$ is a $(CR_{10}R_{20})_n'OR_{13}$ group, $R_{13}$ is suitably hydrogen, aryl, especially phenyl, or $C_{1-10}$ alkyl, especially methyl or ethyl. The n term is preferably 1 to 4, more preferably 2 or 3, such as in an ethyl or propyl group.

When $R_2$ is a $(CR_{10}R_{20})_n'NHS(O)_2 R_{25}$ group, $R_{25}$ is suitably alkyl, especially methyl. The n term is preferably 1 to 4, more preferably 2 or 3, such as in an ethyl or propyl group.

When $R_2$ is a optionally substituted aryl, the aryl is preferably phenyl. The aryl ring may be optionally substituted one or more times, preferably by one or two substituents, independently selected from $C_{1-4}$ alkyl, halogen, especially fluoro or chloro, $(CR_{10}R_{20})_t OR_{13}$, (wherein t is 0, or an integer of 1 to 4), —$(CR_{10}R_{20})_t NR_{10}R_{20}$, especially amino or mono- or di-alkylamino —$(CR_{10}R_{20})_t S(O)_m R_{25}$, wherein m is 0, 1 or 2; —SH—, —$(CR_{10}R_{20})_n$—$NR_8R_9$, —$NR_{10}C(Z)R_8$ (such —NHCO ($C_{1-10}$ alkyl)); —$NR_{10}S(O)_m R_{25}$ (such as —$NHSO_2(C_{1-10}$ alkyl)). Preferably the phenyl is substituted in the 3 or 4-position by —$(CR_{10}R_{20})_t S(O)_m R_{25}$, and $R_{25}$ is preferably $C_{1-10}$ alkyl, especially methyl.

When $R_2$ is an optionally substituted heteroaryl or heteroarylalkyl group the ring may be optionally substituted one or more times, preferably by one or two substituents, independently selected from one or more times, by $C_{1-4}$ alkyl, halogen, especially fluoro or chloro, $(CR_{10}R_{20})_t OR_{13}$, —$(CR_{10}R_{20})_t NR_{10}R_{20}$, especially amino or mono- or di-alkylamino —$(CR_{10}R_{20})_t S(O)_m R_{25}$, wherein m is 0, 1 or 2; —SH—, —$(CR_{10}R_{20})_n$—$NR_8R_9$, —$NR_{10}C(Z)R_8$ such —NHCO($C_{1-10}$ alkyl)); —$NR_{10}S(O)_m R_{25}$ (such as —$NHSO_2(C_{1-10}$alkyl)); t is 0, or an integer of 1 to 4.

One skilled in the art would readily recognize that when $R_2$ is a $(CR_{10}R_{20})_n OC(Z)R_{13}$, or $(CR_{10}R_{20})_n OC(Z)NR_8R_9$ moiety, or any similarly substituted group that n is preferably at least 2 which will allow for the synthesis of stable compounds.

Preferably $R_2$ is a $C_{1-4}$ alkyl (branched and unbranched), a methylthio propyl, a methylsulfinyl propyl, an amino propyl, N-methyl-N-benzylamino propyl group, diethylamino propyl, cyclopropyl methyl, morpholinyl butyl, morpholinyl propyl, a morpholinyl ethyl, a piperidine or a substituted piperidine. More preferably $R_2$ is isopropyl; butyl; t-butyl; n-propyl; methylthiopropyl or methylsulfinyl propyl; morpholino propyl; morpholinyl butyl; phenyl substituted by halogen, thioalkyl or sulfinyl alkyl such as a methylthio, methylsulfinyl or methylsulfonyl moiety; piperidinyl; 1-Formyl-4-piperidine; 1-benzyl-4-piperidine; 1-methyl-4-piperidine, or a 1-ethoxycarbonyl-4-piperidine.

Suitably, $R_3$ is —$X_a P(Z)(X_b R_{13})_2$ or Q—$(Y_1)_t$. Preferably, the $R_3$ moiety is Q—$(Y_1)_t$ and Q is an (un) substituted aryl or heteroaryl moiety. Preferably, when Q is an aryl, it is phenyl, and when Q is a heteroaryl, preferred groups include thienyl, pyrrole, pyridine, or pyrimidine. More preferred Q is phenyl. Q is independently substituted 1 to 3 times by $Y_1$. Preferably t is 1 or 2. More preferably, when $R_3$ is mono-substituted phenyl, the substituent is located at the 4-position.

Preferably Q is substituted by 1 or 2 substituents which include halogen, $C_{1-5}$ alkyl and —$(CR_{10}R_{20})_n Y_2$ wherein $Y_2$ is —$OR_8$, —$NO_2$, —$S(O)_m R_{11}$, —$SR_8$, —$S(O)_m NR_8R_9$; —$NR_8R_9$, —$O(CR_{10}R_{20})_n NR_8R_9$, —$C(O)R_8$, —$CO_2 R_8$, —$CO_2(CR_{10}R_{20})_n'$ $CONR_8R_9$, —CN; —$C(Z)NR_8R_9$, —$NR_{10}S(O)_m R_{11}$, —$NR_{10}C(Z)R_8$, —$NR_{10}C(Z)NR_8R_9$, —$C(Z)NR_8OR_9$, —$N(OR_{21})C(Z)NR_8R_9$, —$NR_{10}C(=NR_{15})NR_8R_9$, —$C(=NOR_{13})NR_8R_9$, 5-$(R_{18})$-1,2,4-oxadizaol-3-yl and 4-$(R_{12})$-5-$(R_{18}R_{19})$-4,5-dihydro-1,2,4oxadiazol-3-yl.

Preferred substituents $Y_1$ for use in $R_3$ when the aryl or heteroaryl group Q is mono-substituted include —$(CR_{10}R_{20})_n Y_2$ wherein: n is 0, 1, 2 or 3, preferably 0 or 1; and $Y_2$ is —$OR_8$, especially where $R_8$ is hydrogen or $C_{1-10}$ alkyl; —$NO_2$; —$S(O)_m'R_{11}$, especially where $R_{11}$ is $C_{1-10}$ alkyl; —$SR_8$, especially where $R_8$ is $C_{1-10}$ alkyl; —$S(O)_m NR_8R_9$, especially where $R_8$ and $R_9$ is each hydrogen or $C_{1-10}$ alkyl or $R_8$ and $R_9$ together with the nitrogen to which they are attached form a 5 to 7 membered ring which optionally includes another heteroatom selected from oxygen, sulfur or $NR_{12}$ and m is 2; n' is 1 to 10; —$NR_8R_9$, especially where $R_8$ and $R_9$ is each hydrogen, methyl or benzyl or $R_8$ and $R_9$ together with the nitrogen to which they are attached form a 5 to 7 membered ring which optionally includes another heteroatom selected from oxygen, sulfur or $NR_{12}$; —$O(CR_{10}R_{20})_n NR_8R_9$, especially where $R_8$ and $R_9$ is each $C_{1-10}$ alkyl; —C(O)$R_8$, especially where $R_8$ is hydrogen or $C_{1-10}$ alkyl; —CO$_2$$R_8$, especially where $R_8$ is hydrogen or $C_{1-10}$ alkyl; —CO$_2$(CR$_{10}$R$_{20}$)$_n$'CONR$_8$R$_9$, especially where $R_8$ and $R_9$ is hydrogen or $C_{1-10}$ alkyl; —CN; —C(Z)NR$_8$R$_9$, especially where $R_8$ and $R_9$ is hydrogen or $C_{1-10}$ alkyl; —NR$_{10}$S(O)$_m$R$_{11}$, especially where $R_{10}$ is hydrogen or $C_{1-10}$ alkyl and $R_{11}$ is $C_{1-10}$ alkyl or a halosubstituted ; —NR$_{10}$C(Z)R$_8$, especially where $R_8$ is $C_{1-10}$ alkyl and $R_{10}$ is hydrogen and Z is oxygen; —C(Z)NR$_8$R$_9$, especially where $R_8$ and $R_9$ is each hydrogen and Z is oxygen; —NR$_{10}$C(Z)NR$_8$R$_9$, especially where $R_8$ and $R_9$ is each hydrogen or $C_{1-10}$ alkyl and Z is oxygen; —N(OR$_{21}$)C(Z)NR$_8$R$_9$, especially where $R_8$ especially where $R_8$, $R_9$ and $R_{21}$ is each hydrogen or $C_{1-10}$ alkyl and Z is oxygen; —C(=NOR$_{13}$)NR$_8$R$_9$, especially where $R_8$, $R_9$ and $R_{13}$ is each hydrogen; —NR$_{10}$C(=NR$_{15}$)NR$_8$R$_9$, especially where $R_8$ and $R_9$ is hydrogen, $C_{1-10}$ alkyl or arylalkyl and $R_{15}$ is cyano; and 5-(R$_{18}$)1,2,4-oxadizaol-3-yl and 4-(R$_{12}$)-5-(R$_{18}$R$_{19}$)-4,5-dihydro-1,2,4-oxadiazol-3-yl, especially where $R_{12}$ is hydrogen and $R_{18}$ and $R_{19}$ is each hydrogen or $C_{1-10}$ alkyl or together are oxo or sulfur.

Preferred substituents for use in $R_3$ when the aryl or heteroaryl group Q is disubstituted include those hereinbefore listed for use when Q is mono-substituted and, as further substituent(s), halogen and $C_{1-10}$ alkyl. When $R_3$ is phenyl substituted with two or three substituents, the alkyl moieties preferably have from one to three carbons, more preferably one. Preferred ring positions for two substituents are the 3- and 4-positions and, for three substituents, the 3-, 4- and 5-positions. The substituent at the 3- and 5-positions is preferably $C_{1-2}$ alkyl, such as methyl, or halogen, such as bromo, fluoro or chloro, while the substituent at the 4-position is preferably hydroxyl.

More preferably, for $R_3$ substituents wherein $Y_1$ is (CR$_{10}$R$_{20}$)$_n$$Y_2$, n is 0 or 1 and $Y_2$ is —OH, —S(O)$_m$'R$_{11}$, especially where $R_{11}$ is $C_{1-10}$ alkyl; —SR$_8$, especially where $R_8$ is $C_{1-10}$ alkyl; —NR$_8$R$_9$, especially where $R_8$ and $R_9$ is hydrogen, alkyl, aryl alkyl, or aryl or $R_8$ and $R_9$ together with the nitrogen to which they are attached form a pyrrolidinyl, piperidinyl or morpholinyl ring, more preferably the $R_8$ and $R_9$ terms in the NR$_8$R$_9$ moiety are hydrogen, methyl or benzyl; —CO$_2$R$_8$, especially where $R_8$ is hydrogen or $C_{1-10}$ alkyl; —S(O)$_m$'NR$_8$R$_9$, especially Where $R_8$ and $R_9$ is each hydrogen or $C_{1-10}$ alkyl; —NR$_{10}$S(O)$_m$R$_{11}$, especially where $R_{10}$ is hydrogen and $R_{11}$ is $C_{1-10}$ alkyl or 5-(R$_{18}$)-1,2,4-oxadizaol-3-yl and 4-(R$_{12}$)-5-(R$_{18}$R$_{19}$)-4,5-dihydro-1,2,4-oxadiazol-3-yl, especially where $R_{12}$ is hydrogen and $R_{18}$ and $R_{19}$ is hydrogen or $C_{1-10}$ alkyl or together are oxo.

Most preferably, $Y_1$ is methylthio, ethylthio, methylsulfinyl, ethylsulfinyl, methylsulfonyl, N,N-dimethylaminomethyl, N-benzyl-N-methylaminomethyl, N-morpholinomethyl, methanesulfonamido, sulphonamidomethyl, 5-methyl-4,5-dihydro-1,2,4-oxadiazol-3-yl or 5,5-dimethyl-4,5-dihydro-1,2,4-oxadiazol-3-yl.

In all instances herein where there is an alkenyl or alkynyl moiety as a substituent group, such as in $R_5$, $R_8$, $R_9$, or $R_{11}$ the unsaturated linkage, i.e., the vinylene or acetylene linkage is preferably not directly attached to the nitrogen, oxygen or sulfur moieties, for instance in $Y_2$ as C(Z)NR$_8$OR$_9$, NR$_{10}$C(Z)NR$_8$R$_9$, or OR$_8$.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)m alkyl, wherein m is 0, 1 or 2, such as methyl thio, methylsulfinyl or methyl sulfonyl; amino, mono & di-substituted amino, such as in the NR$_7$R$_{17}$ group; or where the R$_7$R$_{17}$ may together with the nitrogen to which they are attached cyclize to form a 5 to 7 membered ring which optionally includes an additional heteroatom selected from O/N/S; $C_{1-10}$ alkyl, cycloalkyl, or cycloalkyl alkyl group, such as methyl, ethyl, propyl, isopropyl, t-butyl, etc. or cyclopropyl methyl; halosubstituted $C_{1-10}$ alkyl, such CF$_3$; an optionally substituted aryl, such as phenyl, or an optionally substituted arylalkyl, such as benzyl or phenethyl, wherein these aryl moieties may also be substituted one to two times by halogen, hydroxy, hydroxy substituted alkyl, $C_{1-10}$ alkoxy, S(O)$_m$ alkyl, amino, mono & di-substituted amino, such as in the NR$_7$R$_{17}$ group, $C_{1-10}$ alkyl, or CF$_3$.

When $R_3$ includes a $X_a$—P(Z)($X_b$R$_{13}$)$_2$ group linked either directly to the imidazole ring or indirectly via an aryl or heteroaryl group, $X_a$ is suitably oxygen or $C_{1-4}$ alkylene, optionally interupted by oxygen, for instance —CH$_2$OCH$_2$— and Z and $X_b$ is each oxygen, such that the preferred groups include —OP(O)(OR$_{13}$)$_2$ and —CH$_2$OCH$_2$—P(O)(OR$_{13}$)$_2$.

Preferred substitutions for $R_4$ when it is a 4-phenyl, 4-naphth-1-yl or 5-naphth-2-yl moiety are one or two substituents each independently selected from halogen, —SR$_5$, —SOR$_5$, —OR$_{36}$, or —(CR$_{10}$R$_{20}$)$_m$NR$_{10}$R$_{20}$, and for other positions of substitution on these rings preferred substitution is halogen, —S(O)$_m$R$_8$, —OR$_8$, —(CR$_{10}$R$_{20}$)$_m$NR$_{16}$R$_{26}$, —NR$_{10}$C(Z)R$_8$ and —NR$_{10}$S(O)$_m$R$_{11}$. More preferred substituents for the 4-position in phenyl and naphth-1-yl and on the 5-position in naphth-2-yl include halogen, especially fluoro and chloro, and —SR$_5$ and —SOR$_5$ wherein $R_5$ is preferably a $C_{1-2}$ alkyl, more preferably methyl; of which fluoro is especially preferred. Preferred substituents for the 3-position in phenyl and naphth-1-yl include: halogen, especially chloro; —OR$_8$, especially $C_{1-4}$ alkoxy; amino; —NR$_{10}$C(Z)R$_8$, especially —NHCO($C_{1-10}$ alkyl); and —NR$_{10}$S(O)$_m$R$_{11}$, especially —NHSO$_2$($C_{1-10}$ alkyl). Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido.

A preferred grouping of formula (I) are those compounds wherein $R_2$ is an optionally substituted $C_{1-10}$ alkyl, optionally substituted $C_{3-7}$cycloalkyl, or an optionally substituted $C_{3-7}$cycloalkyl $C_{1-10}$ alkyl, an optionally substituted aryl, an optionally substituted heterocyclic alkyl, an optionally substituted heterocyclic, optionally substituted heteroaryl or heteroarylalkyl, (CR$_{10}$R$_{20}$)$_n$'OR$_{13}$, (CR$_{10}$R$_{20}$)$_n$'S(O)$_m$R$_{25}$, (CR$_{10}$R$_{20}$)$_n$'NR$_8$R$_9$, (CR$_{10}$R$_{20}$)$_n$'C(Z)OR$_{13}$, (CR$_{10}$R$_{20}$)$_n$'NHS(O)$_2$R$_{25}$, (CR$_{10}$R$_{20}$)$_n$'C(Z)R$_{13}$, or (CR$_{10}$R$_{20}$)$_n$'C(=NOR$_{21}$)R$_{13}$; and $R_1$, $R_3$, and $R_4$ are as defined for Formula (I).

More preferred are those compounds wherein $R_2$ is a $C_{1-4}$ alkyl (branched and unbranched), such as isopropyl, butyl, t-butyl, n-propyl, a methylthio propyl, a methylsulfinyl propyl, an amino propyl, N-methyl-N-benzylamino propyl group, (phenylmethyl)amino-1-propyl, diethylamino propyl, cyclopropyl methyl, morpholinyl butyl, morpholinyl propyl, morpholinyl ethyl, 1-Formyl-4-piperidinyl, 1-benzyl- 4-piperidinyl, 1-methyl-4-piperidinyl, 1-ethoxycarbonyl-4-piperidinyl, phenyl substituted by halogen, thioalkyl or sulfinyl alkyl such as a methylthio, methylsulfinyl or methylsulfonyl moiety; and $R_1$, $R_3$, and $R_4$ are as defined for Formula (I).

Further preferred compounds of Formula (I) are those wherein $R_1$ is an optionally substituted 4-pyridyl or pyrimidinyl; and more preferably R₄ is a 2-methyl-4-pyridyl or 2-amino-pyrimidinyl.

Suitable pharmaceutically acceptable salts are well known to those skilled in the art and include basic salts of inorganic and organic acids, such as hydrochloric acid, hydrobromic acid, sulphuric acid, phosphoric acids methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be formed with a pharmaceutically acceptable cation, for instance, if a substituent $Y_1$ in $R_3$ comprises a carboxy group. Suitable pharmaceutically acceptable cations are well known to those skilled in the art and include alkaline, alkaline earth, ammonium and quarternary ammonium cations.

The following terms, as used herein, refer to:

"halo"—all halogens, that is chloro, fluoro, bromo and iodo;

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

"aryl"—phenyl and naphthyl;

"heteroaryl" (on its own or in any combination, such as "heteroaryloxy")—a 5–10 membered aromatic ring system in which one or more rings contain one or more heteroatoms selected from the group consisting of N, O or S, such as, but not limited, to pyrrole, quinoline, isoquinoline, pyridine, pyrimidine, oxazole, thiazole, thiadiazole, triazole, imidazole, or benzimidazole;

"heterocyclic" (on its own or in any combination, such as "heterocyclylalkyl")—a saturated or wholly or partially unsaturated 4–10 membered ring system in which one or more rings contain one or more heteroatoms selected from the group consisting of N, O, or S; such as; but not limited to, pyrrolidine, piperidine, piperazine, morpholine, imidazolidine or pyrazolidine;

"aroyl"—a C(O)Ar, wherein Ar is as phenyl, naphthyl, or aryl alkyl derivative such as defined above, such group include but are note limited to benzyl and phenethyl;

"alkanoyl"—a C(O)$C_{1-10}$alkyl wherein the alkyl is as defined above;

"sulfinyl"—the oxide S(O) of the corresponding sulfide, while the term "thio" refers to the sulfide;

The term "aralkyl" or "heteroarylalkyl" or "heterocyclicalkyl" is used herein to mean an aryl, heteroaryl or heterocyclic moiety as respectively defined above said group connected to $C_{1-6}$ alkyl group as also defined above unless otherwise indicated.

The compounds of the present invention may contain one or more asymmetric carbon atoms and may exist in racemic and optically active forms. All of these compounds are included within the scope of the present invention.

For the purposes herein of nomenclature, the compounds of formula (I) are named by their position corresponding to:

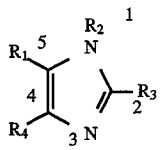

Exemplified compounds of formula (I) include:

2-(4-Cyanophenyl)-4-(4-fluorophenyl)-5-(4-pyridyl)-1H-imidazole

1-Methyl-2-(4-methoxyphenyl)-4-phenyl-5-(4-pyridyl)-imidazole 2-(4-Cyanophenyl)-1-methyl-4-phenyl-5(4-pyridyl)imidazole 2-(4-Aminomethylphenyl)-1-methyl-4-phenyl-5-(4-pyridyl)-imidazole 4-[1-Methyl-4-phenyl-5(4-pyridyl)-imidazol-2-yl]benzoic acid, sodium salt 2-(4-Acetamidomethyphenyl)-1-methyl-4-phenyl-5-(4-pyridyl)imidazole Methyl-4-[1-methyl-4-phenyl-5-(4-pyridyl)-imidazol-2-yl]benzoate 4-(4-Fluorophenyl)-N-1-hydroxy-2-(4-hydroxyphenyl)-5-(4-pyridyl)imidazole 4-(4-Fluorophenyl)-2-(4-hydroxyphenyl)-5-(4-pyridyl)-1H-imidazole 4-[4-(4-Fluorophenyl)-5-(4-pyridyl)-1H-imidazol-2-yl] benzoic acid 2-(4-Cyanophenyl)-4-(4-fluorophenyl)-1-N-hydroxy-5-(4-pyridyl)imidazole 2-(4-Aminomethylphenyl)-4-(4-fluorophenyl)-5-(4-pyridyl)-1H-imidazole 2-(4-Cyanophenyl)-4-(4-fluorophenyl)-N-1-hydroxy-5-(4-quinolyl)imidazole 2-(4-Cyanophenyl)-4-(4-fluorophenyl)-5-(4-quinolyl)-1H-imidazole 2-(3,5-Dibromo-4-hydroxyphenyl)-4-(4-fluorophenyl)-5-(4-pyridyl)-1H-imidazole Ethyl 4-[4-(4-Fluorophenyl)-5-(4-pyridyl)]-1H-imidazol-2-yl]-benzoate 2-[3,5-Dimethyl-4-hydroxy(phenyl)]-4-(4-fluorophenyl)-5-(4-pyridyl)-1H-imidazole 4-(4-Fluorophenyl-2-(2-hydroxyphenyl)-5-(4-pyridyl)-1H-imidazole 4-(4-Fluorophenyl)-2-(4-methylthiophenyl)-5-(4-pyridyl)-1H-imidazole Methyl 4-[4-(4-fluorophenyl)-5-(4-pyridyl)-1H-imidazol-2-yl]-benzoate 4-(4-Fluorophenyl)-2-(4-methylsulfonylphenyl)-5-(4-pyridyl)-1H-imidazole 4-(4-Fluorophenyl)-2-(4-methylsulfinylphenyl)-5-(4-pyridyl)-1H-imidazole N,N-Dimethyl-4-[4-(4-fluorophenyl-5-(4-pyridyl)-1H-imidazol-2-yl]-benzamide 2-[(4-N,N-Dimethyl)aminomethylphenyl]-4-(4-fluorophenyl)-5-(4-pyridyl)-1H-imidazole 2-[4-(Dimethylamino)phenyl]-4-(4-fluorophenyl)-5-(4-pyridyl)-1H-imidazole 4-(4-Fluorophenyl)-2-phenyl-5-(4-pyridyl)-1H-imidazole 2-[4-(3-Dimethylaminopropoxy)phenyl]-4-(4-fluorophenyl)-5-(4-pyridyl)-1H-imidazole 4-(4-Fluorophenyl)-2-(4-nitrophenyl)-5-(4-pyridyl)-1H-imidazole N,N-Dimethyl-4-[2-(4-fluorophenyl)-5-(4-pyridyl)-1H-imidazol-2-yl]benzoyloxyacetamide 2-(4-Aminophenyl)-4-(4-fluorophenyl)-5-(4-pyridyl)-1H-imidazole 4-(4-Fluorophenyl)-2-(4-methanesulfonamidophenyl)-5-(4-pyridyl)-1H-imidazole 4-[4-(4-Fluorophenyl)-5-(4-pyridyl)-1H-imidazol-2-yl]phenyl-sulfonamide N'-Cyano-N-4-[4-(fluorophenyl)-5-(4-pyridyl)-1H-imidazol-2-yl]benzylguanidine 2-[4-(Methanesulfonamido)methylphenyl]-4-(4-fluorophenyl)-5-(4-pyridyl)-1H-imidazole 4-(4-Fluorophenyl)-2-(4-methoxyphenyl)-5-(4-pyridyl)-1H-imidazole 2-(4-Amino-3-iodophenyl)-4-(4-fluorophenyl)-5-(4-pyridyl)-1H-imidazole N-Benzyl-N-methyl-4-[4-(4-fluorophenyl-5-(4-pyridyl)-1H-imidazol-2-yl]benzamide 2-[4-(N-Benzyl-N-methyl)aminomethylphenyl]-4-(4-fluorophenyl)-5-(4-pyridyl)-1H-imidazole 4-(4-Fluorophenyl)-N-1-hydroxy-2-(4-methylthiophenyl)-5-(4-quinolyl)imidazole 4-(4-Fluorophenyl)-2-(4-methylthiophenyl)-5-(4-quinolyl)-1H-imidazole 4-(4-Fluorophenyl)-2-(4-methylsulfinylphenyl)-5-(4-quinolyl)-1H-imidazole 4-(3-Chlorophenyl)-2-(4-methylsulfinylphenyl)-5-(4-pyridyl)-1H-imidazole 4-(3-Chlorophenyl)-N-1-hydroxy-2-(4-methylthiophenyl)-5-(4-pyridyl)-1H-imidazole 4-(3-Chlorophenyl)-2-(4-methylthiophenyl)-5-(4-pyridyl)-1H-imidazole 4-(4-Fluorophenyl)-2-(4-formamidomethylphenyl)-5-(4-pyridyl)-1H-imidazole 4-[4-(4-Fluorophenyl)-5-(4-pyridyl)-1H-imidazol-2-yl]-benzohydroxamic acid O-Benzyl-4-[4-(4-Fluorophenyl)-5-(4-pyridyl)-1H-imidazol-2-yl]-benzohydroxamic acid 4-[4-(4-Fluorophenyl)-5-(4-pyridyl)-1H-imidazol-2-yl] benzamidoxime N''-Methyl-N'-cyano-N-[4-(4-fluorophenyl)-5-(4-pyridyl)-1H-imidazol-2-yl]benzylguanidine N-1-Hydroxy-4-(3-methoxyphenyl)-2-(4-methylthiophenyl)-5-(4-pyridyl)-1H-imidazole 4-(3-Methoxyphenyl)-2-(4-methylthiophenyl)-5-(4-pyridyl)imidazole 4-(3-Methoxyphenyl)-2-(4-methylsulfinylphenyl)-5-(4-pyridyl)-1H-imidazole Morpholino-4-[4-(4-fluorophenyl)-5-(4-pyridyl)-1H-imidazol-2-yl]benzamide 4-(4-Fluorophenyl)-5-[4-(2-methylpyridyl)]-2-(4-methylthiophenyl)-1H-imidazole 4-(4-Fluorophenyl)-5-[4-(2-methylpyridyl)]-2-(4-methylsulfinylphenyl)-1H-imidazole 4-(4-Fluorophenyl)-N-1-hydroxy-5-(4-pyrimidinyl)imidazole 4-(4-Fluorophenyl)-2-(4-methylthiophenyl)-5-(4-pyrimidinyl)-1H-imidazole 4-(4-Fluorophenyl)-2-(4-methylsulfinylphenyl)-5-(4-pyrimidinyl)-1H-imidazole 4-(4-Fluorophenyl)-2-(4-methylsulfonylphenyl)-5-(4-pyrimidinyl)-1H-imidazole 4-(4-Fluorophenyl)-2-(4-Morpholinomethylphenyl)-5-(4-pyridyl)-1H-imidazole 4-(4-Fluorophenyl)-2-(4-hydroxymethyl)-5-(4-pyridyl)-1H-imidazole 4-[4-(4-Fluorophenyl)-5-(4-pyridyl)-1H-imidazol-2-yl]-benzaldehyde 4-(2-Methoxyphenyl)-2-(4-methylsulfinylphenyl)-5-(4-pyridyl)-1H-imidazole N-1-Hydroxy-4-(2-methoxyphenyl)-2-(4-methylthiophenyl)-5-(4-pyridyl)imidazole 4-(2-Methoxyphenyl)-2-(4-methylthiophenyl)-5-(4-pyridyl)-1H-imidazole 3-[4-(4-Fluorophenyl)-5-(4-pyridyl)-1H-imidazol-2-yl] phenyl-5-methyl-4,5-dihydro-1,2,4-oxadiazole 3-[4-(4-Fluorophenyl)-5-(4-pyridyl)-1H-imidazol-2-yl] phenyl-5-methyl-1,2,4-oxadiazole 4-(3-Aminophenyl)-2-(4-methylthiophenyl)-5-(4-pyridyl)-1H-imidazole N-1-Hydroxy-2-(4-methylthiophenyl)-4-(3-nitrophenyl)-5-(4-pyridyl)imidazole 2-(4-Methylthiophenyl)-4-(3-nitrophenyl)-5-(4-pyridyl)-1H-imidazole 4-(3-Methanesulfonamidophenyl)-2-(4-methylthiophenyl)-5-(4-pyridyl)-1H-imidazole 3-[4-(4-Fluorophenyl)-5-(4-pyridyl)-1H-imidazol-2-yl] phenyl-1,2,4-oxadiazol-5-(4H)-one 4-(3-Acetamidophenyl)-2-(4-methylthiophenyl)-5-(4-pyridyl)-1H-imidazole 4-(4-Fluorophenyl)-1-N-hydroxy-5-[4-(2-methylpyridyl)]-2-(4-methylthiophenyl)imidazole 3-[4-(4-Fluorophenyl)-5-(4-pyridyl)-1H-imidazol-2-yl]-phenyl-5,5-dimethyl-4,5-dihydro-1,2,4-oxadiazole N-Hydroxy-N-1-[4-[4-(4-fluorophenyl)5-(4-pyridyl)-1H-imidazol-2-yl]phenyl]ethyl]urea N-Hydroxy-N-[4-[4-(4-fluorophenyl)-5-(4-pyridyl)-1H-imidazol-2-yl]phenyl]-methyl urea 4-(3-Methylthiophenyl)-2-(4-morpholinomethylphenyl)-5-(4-pyridyl)-1H-imidazole 4-(3-Methylsulfinylphenyl)-2-(4-morpholinomethylphenyl)-5-(4-pyridyl)-1H-imidazole 4-(3-Methanesulfonamidophenyl)-2-(4-methylsulfinylphenyl)-5-(4-pyridyl)-1H-imidazole 2-(4-Ethylthiophenyl)-4-(4-fluorophenyl)-5-(4-pyridyl)-1H-imidazole 2-(4-Ethylsulfinylphenyl)-4-(4-fluorophenyl)-5-(4-pyridyl)-1H-imidazole 4-(4-Fluorophenyl)-2-[(4-(4-methyl-1-piperzinyl)-sulfonyl-phenyl]-5-(4-pyridyl)-1H-imidazole 4-(4-Fluorophenyl)-2-[4-(N-methylmethanesulfonamido)-methylphenyl]-5-(4-pyridyl)-1H-imidazole Diethyl [1-methyl-4-phenyl-5-(4-pyridyl)-imidazol-2-yl] methoxy]methylphosphonate 4-(4-Fluorophenyl)-2-(4-methylthiophenyl)-5-(4-pyridyl)-1H-imidazole 4-(4-Fluorophenyl)-2-(3-methylthiophenyl)-5-(4-pyridyl)-1H-imidazole 4-(4-Fluorophenyl)-2-(3-methylsulfinylphenyl)-5-(4-pyridyl)-1H-imidazole 4-(4-Fluorophenyl)-2-(4-methoxyphenyl)-5-(4-pyridyl) imidazole 4-(4-Fluorophenyl)-2-(4-methylsulfinylphenyl)-1-(N-morpholinopropyl)-5-(4-pyridyl)imidazole 4-(4-Fluorophenyl)-2-(4-methylthiophenyl)-1-(N-morpholinopropyl)-5-(4-pyridyl)imidazole 4-(4-Fluorophenyl)-2-(4-methylsulfonylphenyl)-1-(N-morpholinopropyl)-5-(4-pyridyl)imidazole 4-(4-Fluorophenyl)-1-(methylthio-1-propyl)-2-([4-N-morpholinomethyl]phenyl)-5-(4-pyridyl)imidazole 4-(4-Fluorophenyl)-1-(methylsulfinyl-1-propyl)-2-([4N-morpholinomethyl]phenyl)5-(4-pyridyl)imidazole 4-(4-Fluorophenyl)-1-(methylsulfonyl-1-propyl)-2-([4-N-morpholinomethyl]phenyl)-5-(4-pyridyl)imidazole and pharmaceutically acceptable salts thereof.

Compounds of formula (I) are imidazole derivatives which may be readily prepared using procedures well-known to those skilled in the art, and described in, for instance, Comprehensive Heterocyclic Chemistry, ed Katritzky and Rees, Pergamon Press, 1984, 5, 457–497, from starting materials which are either commercially available or can be prepared from such by analogy with well-known processes. A key step in many such syntheses is the formation of the central imidazole nucleus, to give compounds of formula (I). Suitable procedures are described in inter alia U.S. Pat. Nos. 3,707,475 and 3,940,486 which are herein incorporated by reference in their entirety. These patents describe the synthesis of α-diketones and α-hydroxyketones (benzoins) and their subsequent use in preparing imidazoles and N-hydroxyl imidazoles. Thereafter, further compounds of formula (I) may be obtained by manipulating substituents in any of the groups $R_1$, $R_2$, $R_3$ and $R_4$ using conventional functional group interconversion procedures.

In particular, in a first process, compounds of formula (I) may be prepared by condensing an α-diketone of formula (II):

$R_1COCOR_4$            (II)

wherein $R_1$ and $R_4$ are as hereinbefore defined, or an equivalent thereof, with an aldehyde of the formula (III):

$R_3CHO$            (III)

wherein $R_3$ is as hereinbefore defined, or an equivalent thereof, and, if necessary, with ammonia or a source thereof, under imidazole-ring forming conditions.

Suitable equivalents of the α-diketone are well known to those skilled in the art and include the corresponding α-keto-oxime and α-dioxime. Suitable equivalents of the aldehyde of formula (III) are well known in the art and include the corresponding oxime and acetal.

Ammonia, or a source thereof, is preferably used in excess, with at least a dimolar amount being used in the case of the α-diketone and at least an equimolar amount in the case of the α-keto-oxime.

Suitable sources of ammonia include ammonium salts of organic carboxylic acids, such as an ammonium $C_{1-6}$ alkanoate, for instance ammonium acetate and ammonium formate, preferably ammonium acetate, and carboxylic amides, in particular of formic acid, such as formamide. An ammonium salt is generally used in large excess and in the presence of an acid, such as a $C_{1-6}$ carboxylic acid which acid may also be used as a solvent for the reaction. If formamide is used, this may be used in excess, as the reaction solvent. An alternative solvent such as ethanol or dimethyl sulphoxide (Lantos et al, J Het Chem, 19, 1375, 1982) may be used. An additional solvent may also be employed, for instance, dimethyl formamide may be used with formamide. The reaction is generally carried out at elevated temperatures, for instance under reflux conditions, and if desired, in a sealed vessel optionally under pressure and/or an inert gas atmosphere, for instance nitrogen.

A further suitable source of ammonia is hydroxylamine, in which case the initially formed imidazole is an N-hydroxy-N-oxide imidazole. This may then be reduced to the corresponding N-hydroxy imidazole by treating with a suitable reducing agent such as sodium borohydride, in an appropriate solvent such as methanol, following the method of Akange and Allan, Chem and Ind, 5 Jan. 1975, 38. The N-hydroxy imidazole may in turn be converted to an imidazole of formula (I) in which $R_2$ is hydrogen by treatment with a conventional deoxygenating agent such as phosphorus trichloride or a trialkylphosphite such as trimethyl- or triethyl-phosphite. N-hydroxy-N-oxide imidazoles may be readily obtained by treating an α-diketone of formula (II) with an aldehyde of formula (II) with about two equivalents of hydroxylamine or the corresponding aldoxime and about one equivalent of hydroxylamine, under proton catalysis. Alternatively, the N-oxide may be obtained by the acid catalysed condensation of the corresponding α-dioxime or α-keto-oxime with an aldoxime of the aldehyde of formula (III).

When the compound of formula (II) is an α-keto-oxime derivative, it will be appreciated that the product initially obtained will be a compound of formula (I) in which $R_2$ is hydroxyl which may be converted into a compound of formula (I) in which $R_2$ is hydrogen as described above.

It will be appreciated by those skilled in the art that in some instances, it will not be necessary to provide a separate source of ammonia as the α-diketone or aldehyde equivalent may already contain such a source. Examples of this include α-dioxime or α-keto-oxime and aldoxime.

The compounds of formula (II) may be obtained by applying well-known synthetic procedures, some of which are illustrated in schemes I and II. Although these illustrate syntheses in which $R_4$ is either 4-pyridyl or 4-quinolinyl, they may be equally applied to any of the other heteroaryl rings within the definition of $R_4$ by appropriate choice of starting material.

In Scheme I, the anion prepared from 1, by treatment with a strong base such as lithium di-iso-propylamide, is condensed with a substituted benz-aldehyde, to give, after removal of the protecting group, the diol 2. This may then be converted to the α- 3 by a Swern oxidation of which any number of potentially useful variations are known and may be used. The α-diketone 3 is then cyclised to an imidazole 4, a compound of formula (I), by heating 3 with a substituted benzaldehyde in a mixture of ammonium acetate, as the source of ammonia, and an appropriate solvent, for example acetic acid or DMSO. The imidazole 4 may then be transformed into other imidazoles 5 by appropriate functional group interconversion procedures. Scheme I also illustrates the preparation of a protected α-hydroxyketone 2a, by condensing the anion of 1 with an appropriately activated carbonyl derivative of a substituted benzamide, such as the N-methoxy-N-methylamide, to yield a protected a-hydroxyketone. This adduct 2a may then be directly converted to the imidazole 5, using a combination of a copper (II) salt, such as copper (II) acetate, as an oxidising agent and ammonium acetate as a source of ammonia. The α-hydroxyketone 2a may also be deprotected and then oxidised to give an α-diketone 3, for instance using Swern oxidation

Scheme I

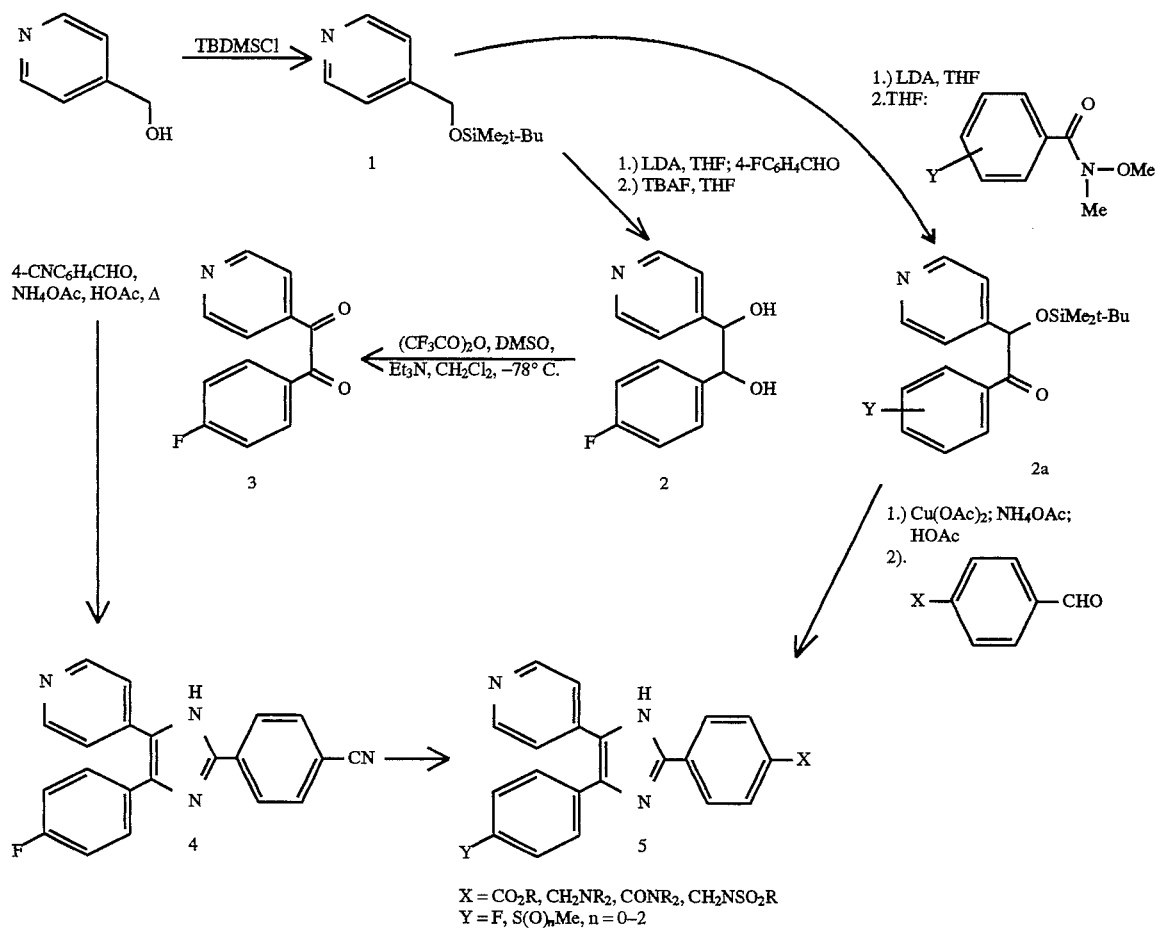

X = CO₂R, CH₂NR₂, CONR₂, CH₂NSO₂R
Y = F, S(O)ₙMe, n = 0–2

Scheme II illustrates the use of an α-keto-oxime for preparing a compound of formula (I). A heterocyclic ketone 7 is prepared by adding the anion of 4-methylquinoline (prepared by treatment thereof with an alkyl lithium, such as n-butyl lithium) to an N-alkyl-O-alkoxybenzamide. Alternatively, the anion may be condensed with a benzaldehyde, to give an alcohol which is then oxidised to the ketone 7. The α-keto-oxime 8 is then prepared from 7 using standard conditions, such as reaction with sodium nitrite, and this may then be reacted with a benzaldehyde to afford an N-hydroxyimidazole 9, a compound of formula (I) in which $R_2$ is hydroxy. This may converted to 10, a further compound of formula (I) in which $R_2$ is hydrogen, by treating it with a deoxygenating agent such as phosphorus trichloride or a trialkyl phosphite, such trimethyl or triethylphosphite. For compounds of formula (I) wherein $R_3$ is —(CR₁₀R₂₀)ₙ—P(Z)—(XₑR₁₃)₂, the reagent OHC—(CR₁₀R₂₀)ₙ—P(Z)—(XₑR₁₃)₂ may be used instead of OHC—C₆H₄—X to make the appropriately substituted compound 9.

Scheme II

-continued
Scheme II

-continued
Scheme II

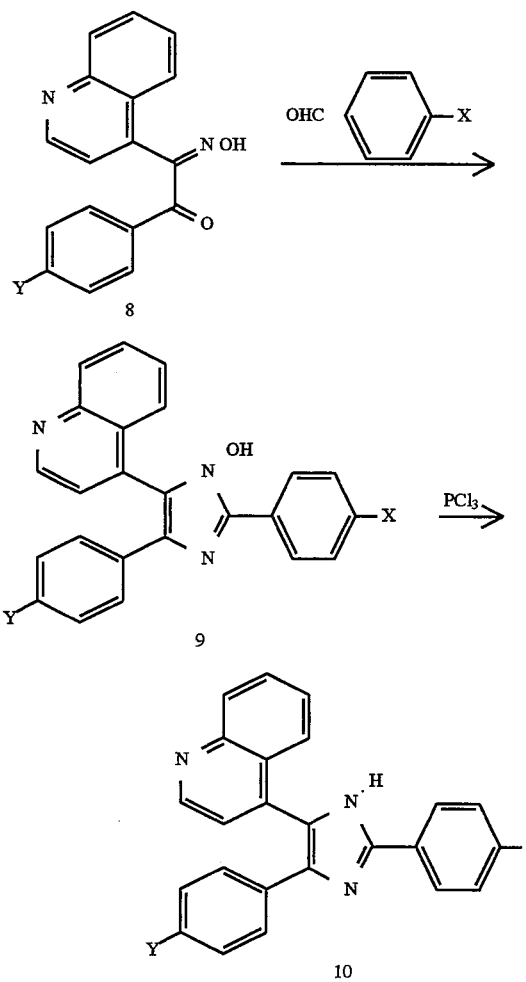

In a further process, a compound of formula (I) may be obtained by treating an α-hydroxyketone compound of formula (IIA):

R'CHOHCOR"  (IIA)

wherein one of R' and R" is $R_1$ and the other is $R_4$, a suitably protected derivative thereof or the α-hydroxy-oxime or α-haloketone derivative thereof, with an oxidising agent capable of converting said compound into the corresponding α-diketone, in the presence of an aldehyde of formula (III) or an equivalent thereof, and a source of ammonia. Suitable oxidising agents include, for example, an oxidising heavy metal salt, preferably an organic copper (II) salt, such as copper (II) acetate or copper (II) citrate. The reaction may be effected in a solvent such as acetic acid, under reflux conditions. Alternatively, a lower alkanol solvent, such as methanol or ethanol, may be used, preferably at a temperature in the region of from 30° to 100° C. (see The Chemistry of Heterocyclic Compounds, Imidazole and its derivatives, part I, ed. Weissberger, Interscience Publishers, Inc., New York, 1953, 38). This approach is also illustrated in Scheme I.

In a further process, a compound of formula (I) may be obtained by treatment with a compound of formula (XI) as described later. A compound of Formula (XI) is obtained by treating a compound (an amidine) of formula (IV):

$$R_3C(=NH)NHR_2 \qquad (IV)$$

wherein $R_2$ and $R_3$ are as hereinbefore defined, or a salt thereof, with a reactive ester of an α-hydroxyketone of formula (IIA) or the corresponding α-haloketone, in an inert solvent such as a halogenated hydrocarbon solvent, for example chloroform, at a moderately elevated temperature and, if necessary, in the presence of a suitable condensation agent such as a base. Suitable reactive esters include esters of strong organic acids such as a lower alkane sulphonic or aryl sulphonic acid, for instance, methane or p-toluene sulphonic acid. The amidine of formula (IV) is preferably used as the salt, suitably the hydrochloride salt, which may then be converted into the free amidine in situ, by employing a two phase system in which the reactive ester is in an inert organic solvent such as chloroform, and the salt is in an aqueous phase to which a solution of an aqueous base is slowly added, in dimolar amount, with vigorous stirring. Suitable amidines of formula (IV) may be obtained by standard methods, see for instance, Garigipati R, Tetrahedron Letters, 190, 31, 1989.

Compounds of Formula (IV) wherein $R_2$ is methyl, for instance may be made by the route indicated below.

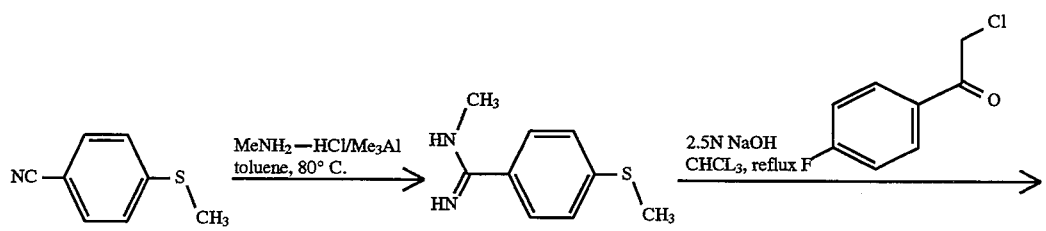

-continued

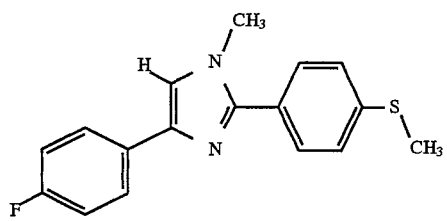

1.) EtOC=OCl, pyridine
2.) sulfur/decalin, Δ

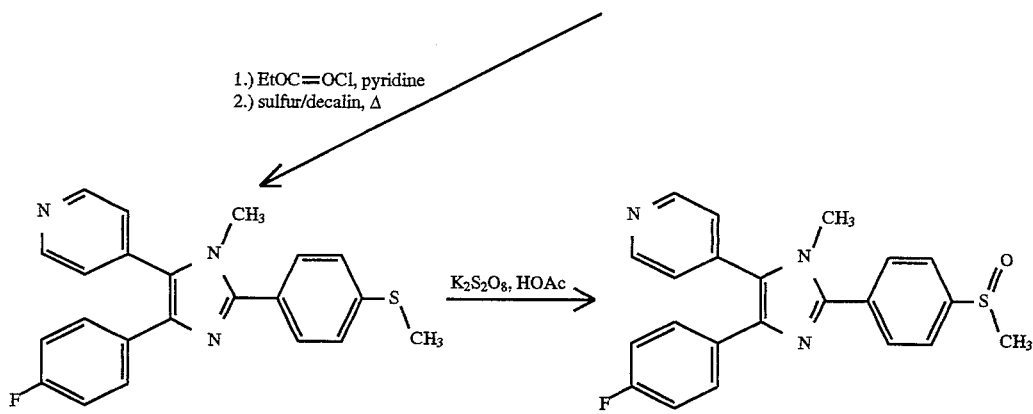

In a further process, a compound of formula (I) may be obtained by treating an iminoether of formula (V):

R₃C=NOR  (V)

wherein $R_3$ is as hereinbefore defined and R is $C_{1-10}$ alkyl, aryl or aryl $C_{1-4}$ alkyl, with an α-aminoketone of the formula (VI):

R'CHNH₂COR"  (VI)

wherein one of R' and R" is $R_1$ and the other is $R_4$ in a suitable solvent.

In a further process, N-substituted compounds of formula (I) may be prepared by treating the anion of an amide of formula (VII):

R₁CH₂NR₂COR₃  (VII)

wherein $R_1$ and $R_3$ are as hereinbefore defined and $R_2$ is as hereinbefore defined other than hydrogen, with:

(a) a nitrile of the formula (VIII):

R₄CN  (VIII)

wherein $R_4$ is as hereinbefore defined, or (b) an excess of an acyl halide, for instance an acyl chloride, of the formula (IX):

R₄COHal  (IX)

wherein $R_4$ is as hereinbefore defined and Hal is halogen, or a corresponding anhydride, to give a bis-acylated intermediate which is then treated with a source of ammonia, such as ammonium acetate.

This approach permits the regiospecific preparation of compound of formula (I) substituted at the 1-position, as illustrated in Scheme III. A primary amine RNH₂ is treated with 4-chloromethylpyridine to give 11 which is then converted to the amide 12 by standard techniques. Deprotonation of 12 with a strong amide base, such as lithium di-iso-propyl amide or sodium bis-(trimethylsilyl)amide, followed by addition of an excess of an aroyl chloride yields the bis-acylated compound 13 which is then closed to an imidazole compound of formula (I), 14, by heating in acetic acid containing ammonium acetate. Alternatively, the anion of 12 may be reacted with a substituted aryl nitrile to produce the imidazole 14 directly.

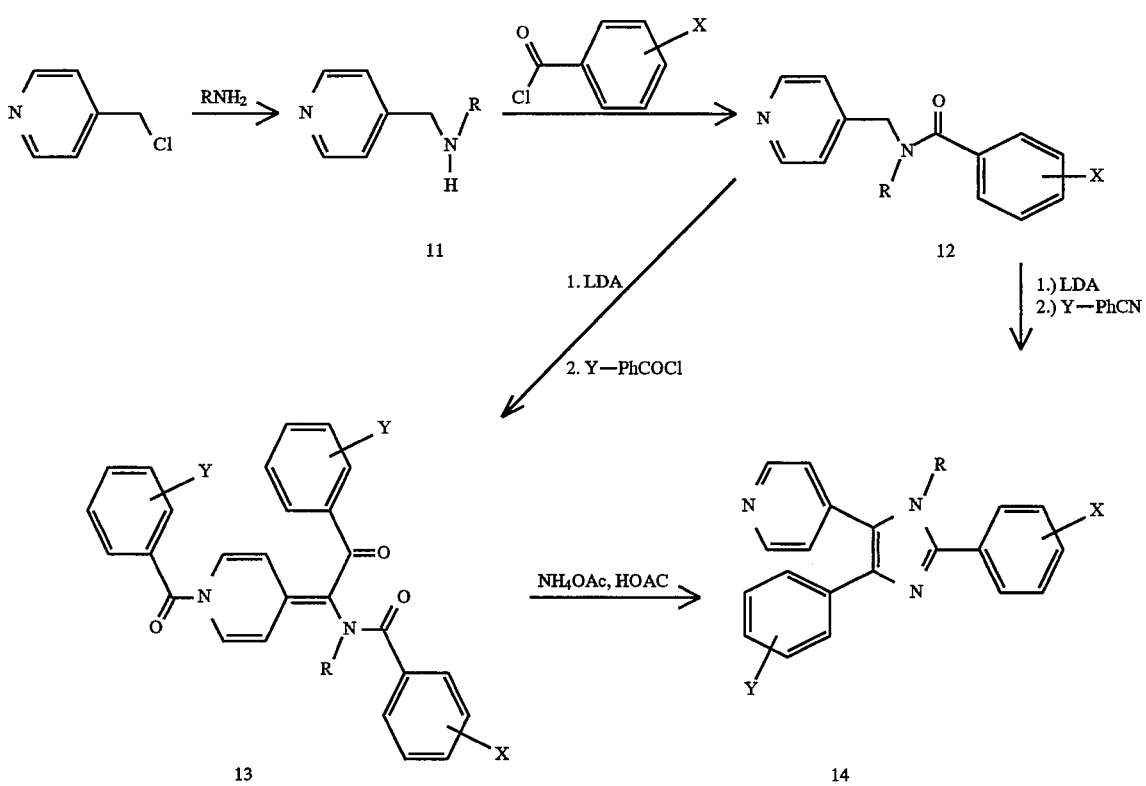

Scheme III

In a further process, compounds of formula (I) may be prepared by treating a compound of formula (X):

R'COCHR"X_cCOR_3          (X)

wherein R', R" and $R_8$ are as hereinbefore defined and $X_c$ is O or NH, with a source of ammonia, as hereinbefore described, under imidazole ring forming conditions or cyclising the corresponding Schiff's base, formed by treating the compound of formula (X) in which $X_c$ is NH With an amine $R_2NH_2$, for instance thermally or with the aid of a cyclising agent such as phosphorus oxychloride or phosphorus pentachloride (see Engel and Steglich, Liebigs Ann Chem, 1978, 1916 and Strzybny et al., J Org Chem, 1963, 28, 3381). Compounds of formula (X) may be obtained, for instance, by acylating the corresponding α-keto-oxime ($X_c$ is NH) or α-hydroxyketone ($X_c$ is O) with an acyl halide of the formula $R_3COHal$ wherein $R_3$ is as hereinbefore defined, or the corresponding anhydride, under standard acylating conditions.

In a further process, compounds of formula (I) may be prepared by coupling a suitable derivative of a compound of formula (XI):

(XI)

wherein: $T_2$ is a nitrogen protecting group or $R_2$, other than hydrogen; and $T_1$ is hydrogen, $T_3$ is Q and $T_4$ is $R_4$; $T_1$ is $R_1$, $T_3$ is hydrogen and $T_4$ is $R_4$; or $T_1$ is $R_1$, $T_3$ is Q and $T_4$ is hydrogen, in which $R_1, R_2, R_3, R_4$ and Q are as hereinbefore defined; with: (i) when $T_1$ is hydrogen, a suitable derivative of the heteroaryl ring $R_1H$, under ring coupling conditions, to effect coupling of the heteroaryl ring $R_1$ to the imidazole nucleus at position 5; (ii) when $T_3$ is hydrogen, a suitable derivative of the aryl or heteroaryl ring QH, under ring coupling conditions, to effect coupling of the ring Q to the imidazole nucleus at position 2; or (iii) when $T_4$ is hydrogen, a suitable derivative of the aryl ring $R_4H$, under ring coupling conditions, to effect coupling of the aryl ring $R_4$ to the imidazole nucleus at position 4.

Such aryl/heteroaryl coupling reactions are well known to those skilled in the art. In general, an organometallic synthetic equivalent of an anion of one component is coupled with a reactive derivative of the second component, in the presence of a suitable catalyst. The anion equivalent may be formed from either the imidazole of formula (XI), in which case the aryl/heteroaryl compound provides the reactive derivative, or the aryl/heteroaryl compound in which case the imidazole provides the reactive derivative. Accordingly, suitable derivatives of the compound of formula (IX) or the aryl/heteroaryl rings include organometallic derivatives such as organomagnesium, organozinc, organostannane and boronic acid derivatives and suitable reactive derivatives include the the bromo, iodo, fluorosulfonate and trifluoromethanesulphonate derivatives. Suitable procedures are described in WO 91/19497, the disclosure of which is herewith incorporated.

Suitable organomagnesinm and organozinc derivatives of a compound of formula (XI) may be reacted with a halogen, fluorosulfonate or triflate derivative of the heteroaryl or aryl ring, in the presence of a ring coupling catalyst, such as a palladium (O) or palladium (II) catalyst, following the procedure of Kumada et al., Tetrahedron Letters, 22, 5319 (1981). Suitable such catalysts include tetrakis- (triphenylphosphine)palladium and $PdCl_2[1,4$-bis-(diphenylphosphino)-butane], optionally in the presence of lithium chloride and a base, such as triethylamine. In addition, a nickel (II) catalyst, such as $Ni(II)Cl_2(1,2$-biphenylphosphino)ethane, may also be used for coupling an aryl ring, following the procedure of Pridgen, J. Org. Chem, 1982, 47, 4319. Suitable reaction solvents include hexamethylphosphoramide. When the heteroaryl ring is 4-pyridyl, suitable derivatives include 4-bromo- and 4-iodo-pyridine and the fluorosulfonate and triflate esters of 4-hydroxy pyridine. Similarly, suitable derivatives for when the aryl ring is phenyl include the bromo, fluorosulfonate, triflate and, preferably, the iodo-derivatives. Suitable organomagnesium and organozinc derivatives may be obtained by treating a compound of formula (XI) or the bromo derivative thereof with an alkyllithium compound to yield the corresponding lithium reagent by deprotonation or transmetallation, respectively. This lithium intermediate may then be treated with an excess of a magnesium halide or zinc halide to yield the corresponding organometallic reagent.

A trialkyltin derivative of the compound of formula (XI) may be treated with a bromide, fluorosulfonate, triflate, or, preferably, iodide derivative of an aryl or heteroaryl ring compound, in an inert solvent such as tetrahydrofuran, preferably containing 10% hexamethylphosphoramide, in the presence of a suitable coupling catalyst, such as a palladium (0) catalyst, for instance tetrakis-(triphenylphosphine)palladium, by the method described in by Stille, J. Amer. Chem. Soc., 1987, 109, 5478, U.S. Pat. Nos. 4,719,218 and 5,002,942; or by using a palladium (II) catalyst in the presence of lithium chloride optionally with an added base such as triethylamine, in an inert solvent such as dimethyl formamide. Trialkyltin derivatives may be conveniently obtained by metallation of the corres-ponding compound of formula (XI) with a lithiating agent, such as s-butyl-lithium or n-butyllithium, in an ethereal solvent, such as tetrahydrofuran, or treatment of the bromo derivative of the corresponding compound of formula (XI) with an alkyl lithium, followed, in each case, by treatment with a trialkyltin halide. Alternatively, the bromo- derivative of a compound of formula (XI) may be treated with a suitable heteroaryl or aryl trialkyl tin compound in the presence of a catalyst such as tetrakis-(triphenyl-phosphine)palladium, under conditions similar to those described above.

Boronic acid derivatives are also useful. Hence, a suitable derivative of a compound of formula (XI), such as the bromo, iodo, triflate or fluorosulphonate derivative, may be reacted with a heteroaryl- or aryl-boronic acid, in the presence of a palladium catalyst such as tetrakis-(triphenylphosphine)-palladium or $PdCl_2[1,4$-bis-(diphenylphosphino)-butane] in the presence of a base such as sodium bicarbonate, under reflux conditions, in a solvent such as dimethoxyethane (see Fischer and Haviniga, Rec. Trav. Chim. Pays Bas, 84, 439, 1965, Suieckus, V., Tetrahedron Lett., 29, 2135, 1988 and Terashimia, M., Chem. Pharm. Bull., 11,4755, 1985). Non-aqueous conditions, for instance, a solvent such as DMF, at a temperature of about 100° C., in the presence of a Pd(II) catalyst may also be employed (see Thompson W. J. et al,. J. Org. Chem, 49, 5237, 1984). Suitable boronic acid derivatives may be prepared by treating the magnesium or lithium derivative with a trialkylborate ester, such as triethyl, tri-iso-propyl or tributylborate, according to standard procedures.

In such coupling reactions, it will be readily appreciated that due regard must be exercised with respect to functional groups present in the compounds of formula (XI). Thus, in general, amino and sulfur substituents should be non-oxidised or protected and the N-1 nitrogen of a compound of formula (XI) be protected, if an NH compound is finally required. Nitro, bromo, iodo and hydroxyl groups should preferably be avoided in compounds of formula (XI) in which $T_1$ is hydrogen.

Compounds of formula (XI) are imidazoles and may be obtained by any of the procedures herein before described for preparing compounds of formula (I). In particular, an a-halo-ketone $R_4COCH_2Hal$ (for compounds of formula (XI) in which $T_1$ is hydrogen) or $R_1COCH_2Hal$ (for compounds of formula (XI) in which $T_4$ is hydrogen) may be reacted with an amidine of formula (IV) or a salt thereof, in an inert solvent such as a halogenated hydrocarbon solvent, for instance chloroform, at a moderately elevated temperature, and, if necessary, in the presence of a suitable condensation agent such as a base. The preparation of suitable α-halo-ketones is described in WO 91/19497. For a compound of formula (XI) in which $T_3$ is hydrogen, an α-diketone of formula (II) may be condensed with a formaldehyde or an equivalent thereof, in the presence of a source of ammonia. Suitable bromo derivatives of the compound of formula (XI) may be obtained by brominating the corresponding compound of formula (XI) under standard brominating conditions, for instance bromine in a solvent such as dichloromethane or THF.

Compounds of formula (I) may also be prepared by a process which comprises reacting a compound of formula (XI), wherein $T_1$ is hydrogen, with an N-acyl heteroaryl salt, according to the method disclosed in U.S. Pat. Nos. 4,803, 279, 4,719,218 and 5,002,942, to give an intermediate in which the heteroaryl ring is attached to the imidazole nucleus and is present as a 1,4-dihydro derivative thereof, which intermediate may then be subjected to oxidative-deacylation conditions. The heteroaryl salt, for instance a pyridinium salt, may be either preformed or, more preferably, prepared in situ by adding a substituted carbonyl halide (such as an acyl halide, an aroyl halide, an arylalkyl haloformate ester, or, preferably, an alkyl haloformate ester, such as acetyl bromide, benzoylchloride, benzyl chloroformate, or, preferably, ethyl chloroformate) to a solution of the compound of formula (XI) in the heteroaryl compound $R_1H$ or in an inert solvent such as methylene chloride to which the heteroaryl compound has been added. Suitable deacylating and oxidising conditions are described in U.S. Pat. Nos. 4,803,279, 4,719,218 and 5,002,942, which references are hereby incorporated in their entirety. Suitable oxidising systems include sulfur in an inert solvent or solvent mixture, such as decalin, decalin and diglyme, p-cymene, xylene or mesitylene, under reflux conditions, or, preferably, potassium t-butoxide in t-butanol with dry air or oxygen.

Once the imidazole nucleus has been established, further compounds of formula (I) which may be prepared by applying standard techniques for functional group interconversion, for instance: $-C(O)NR_8R_9$ from $-CO_2CH_3$ by heating with or without catalytic metal cyanide, e.g. NaCN, and $HNR_8R_9$ in $CH_3OH$; $-OC(O)R_8$ from $-OH$ with e.g., $ClC(O)R_8$ in pyridine; $-NR_{10}-C(S)NR_8R_9$ from $-NHR_{10}$ with an alkylisothiocyante or thiocyanic acid; $NR_6C(O)OR_6$ from $-NHR_6$ with the alkyl chloroformate; $-NR_{10}C(O)NR_8R_9$ from $-NHR_{10}$ by treatment with an isocyanate, e.g. $HN=C=O$ or $R_{10}N=C=O$; $-NR_{10}-C(O)R_8$ from $-NHR_{10}$ by treatment with $ClC(O)$ $R_8$ in pyridine; $-C(=NR_{10})NR_8R_9$ from $-C(NR_8R_9)SR_8$ with $H_3NR8^+OAc^-$ by heating in alcohol; $-C(NR_8R_9)SR_8$ from $-C(S)NR_8R_9$ with $R_6$-I in an inert solvent, e.g.

acetone; —C(S)NR₈R₉ (where R₈ or R₉ is not hydrogen) from —C(S)NH₂ with HNR₈R₉, —C(=NCN)—NR₈R₉ from —C(=NR₈R₉)—SR₈ with NH₂CN by heating in anhydrous alcohol, alternatively from —C(=NH)—NR₈R₉ by treatment with BrCN and NaOEt in EtOH; —NR₁₀—C(=NCN)SR₈ from —NHR₁₀ by treatment with (R₈S)₂C=NCN; —NR₁₀SO₂R₈ from —NHR₁₀ by treatment with ClSO₂R₈ by heating in pyridine; —NR₁₀C(S)R₈ from —NR₁₀C(O)R₈ by treatment with Lawesson's reagent [2,4-bis(4-methoxyphenyl)-1,3,2,4-dithiadiphosphetane-2,4-disulfide]; —NR₁₀SO₂CF₃ from —NHR₆ with triflic anhydride and base; —NR₁₀C(O)—C(O)—OR₈ from —NHR₁₀ with, e.g. methyloxalyl chloride and a base such as triethylamine; —NR₁₀C(O)—C(O)—NR₈R₉ from —NR₁₀C(O)—C(O)—OR₈ with HNR₈R₉; and 1-(NR₁₀)-2-imidazolyl from —C(=NH)NHR₁₀ by heating with 2-chloroacetaldehyde in chloroform (wherein R₆, R₈, R₉ and R₁₀ are as hereinbefore defined).

Compounds of formula (I) in which R₂ is hydrogen may be readily converted into further compounds of formula (I) in which R₂ is other than hydrogen, for instance alkyl, by conventional procedures such as alkylation or acylation followed by reduction. Such methods are in general relatively inefficient as they lack regiospecificty and the desired N-1 product has to be separated from the mixture of N-1 and N-3 products, for instance by chromatography or fractional crystallisation.

Compounds of Formula (I) wherein R₂ is methyl and R₁ is 4-pyridyl or 4-(2-amino)pyrimidinyl for example may be made by the route indicated below.

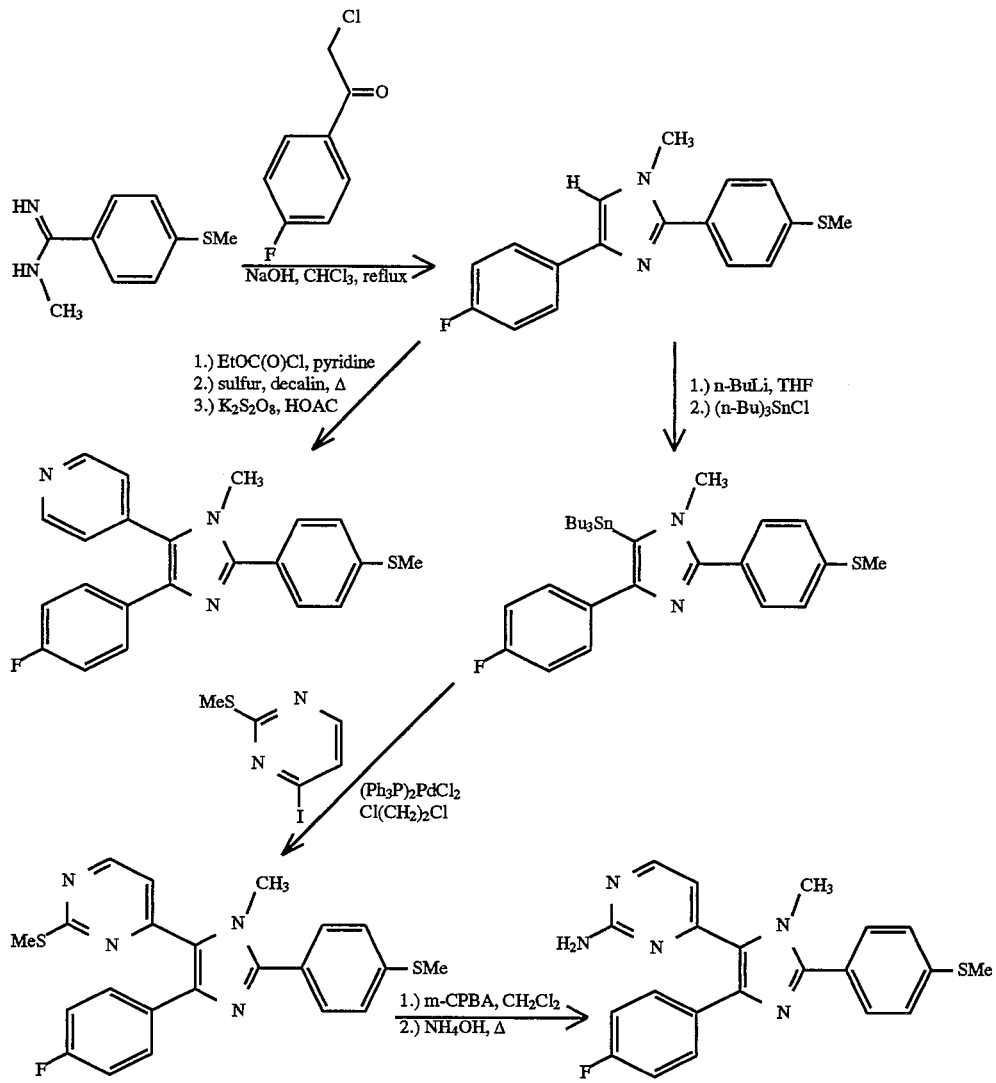

Suitable protecting groups for use with hydroxyl groups and the imidazole nitrogen are well known in the art and described in many references, for instance, Protecting Groups in Organic Synthesis, Greene T. W., Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, (CR₁₀R₂₀)n. Suitable examples of imidazole nitrogen protecting groups include tetrahydropyranyl.

It should be noted that the compounds of Formula (I), where R₄ may be an alkylsulfinyl, arylsulfinyl, alkylsulfonyl, or arylsulfonyl are prodrugs which are reductively converted in vivo to the corresponding alkylthio or arylthio form.

Pharmaceutically acid addition salts of compounds of formula (I) may be obtained in known manner, for example by treatment thereof with an appropriate amount of acid in the presence of a suitable solvent.

The invention will now be described by reference to the following examples which are merely illustrative and are not to be construed as a limitation of the scope of the present invention.

SYNTHETIC EXAMPLES

Example 1

2-(4-Cyanophenyl)-4-(4-fluorophenyl)-5-(4-pyridyl)-1H-imidazole

To a solution of 2-(4-cyanophenyl)-4-(4-fluorophenyl)-N-1-hydroxy-5-(4-pyridyl)-imidazole (4.5 g, 13.2 mmol) [See Ex. 10 below] in DMF (50 mL) was added triethyl phosphite (3.4 mL, 20 mmol), and the resulting mixture was heated at 100° C. for 2 h. After cooling, the mixture was poured into $H_2O$, and the solid which formed was collected by filtration, washed with $H_2O$ and dried in vacuo to afford the title compound (4.0 g, 89%). Recrystallization from $CH_2Cl_2$/MeOH gave white solid with amp of 268°–269° C.

Example 2

1-Methyl-2-(4-methoxyphenyl)-4-phenyl-5-(4-pyridyl)-imidazole (a) N-Methyl-N-(4-picolyl)amine To 4-picolyl chloride, hydrochloride (10 g, 0.06 mol) was added methylamine (50 mL of 40% aqueous solution, 0.58 mol), and the resulting purple solution was stirred at rt for 30 min, then poured into $H_2O$. The mixture was extracted with $CH_2Cl_2$ (6×), and the combined organic extracts were evaporated. The residue was filtered under reduced pressure through a silica gel column, eluting with a solvent gradient of 0–10% MeOH/$CHCl_3$ to provide the title compound as a light yellow oil (4.8 g, 66%): $^1$H NMR ($CDCl_3$): d 8.50 (dd, 2H); 7.20 (dd, 2H); 3.70 (s, 2H); 2.40 (s, 3H); 1.70 (br, 1H).

(b) 4-Methoxy-N-methyl-N-(4-picolyl)benzamide—To a solution of N-methyl-N-(4-picolyl)amine (0.40 g, 3.3 mmol) and triethylamine (1.5 mL, 10.8 mmol) in $CH_2Cl_2$ (15 mL) was added 4-methoxybenzoyl chloride (1.2 g, 7.3 mmol). The resulting mixture was stirred at rt for 15 min, and then partitioned between 2.5N NaOH and $Et_2O$. The organic extract was washed with saturated aqueous NaCl and dried ($MgSO_4$). The solvent was removed in vacuo, and the residue was purified by flash chromatography, eluting with a solvent gradient of 2–4% MeOH/$CHCl_3$. The material that was isolated was triturated with $Et_2O$ to provide the title compound as a light yellow solid (0.18 g, 21%): $^1$H NMR (CDCl3): d 8.60 (d, 2H); 7.43 (br d, 2H); 7.20 (br s, 2H); 6.90 (br d, 2H); 4.66 (br s, 2H); 3.80 (s, 3H); 3.00 (s, 3H).

(c) 1-Methyl-2-(4-methoxyphenyl)-4-phenyl-5-(4-pyridyl)-imidazole—To a solution of diisopropylamine (0.16 mL, 1.1 mmol) in THF at –78° C. was added n-butyllithium (0.38 mL of 2.5M solution, 0.95 mmol). To the resulting mixture was added a solution of 4-methoxy-N-methyl-N-(4-picolyl)benzamide (0.16 g, 0.62 mmol) in THF. The resulting dark red solution was warmed to –40° C. and stirred for 15 min, at which time benzonitrile (0.13 mL, 1.2 mmol) was added. The mixture to warmed to rt and stirred for 10 h. Aqueous $NH_4Cl$ (0.5 mL) was added, and the mixture was concentrated under reduced pressure. The residue was purified by flash chromatography, eluting with a solvent gradient of 2–4% MeOH/$CHCl_3$. The material which was isolated was triturated with $Et_2O$ and recrystallized from EtOAc to provide the title compound as an off-white solid (35 mg, 17%): mp 193°–194° C.

Example 3

2-(4-Cyanophenyl)-1-methyl-4-phenyl-5(4-pyridyl) imidazole (a) 4-Cyano-N-methyl-N-(4-picolyl)benzamide The title compound was prepared using the same procedure as described in Example 2, step (b) except using 4-cyanobenzoyl chloride: $^1$H NMR ($CDCl_3$): d 8.49 (dd, 2H); 7.86–7.04 (m, 6H); 4.70 and 4.43 (two br s, 2H); 3.08 and 2.89 (two br s, 3H).

(b) 4-Cyano-N-[N"-a-dibenzoyl-1,4-dihydropyridyl-methylenyl]-N-methylbenzamide—To a solution of diisopropylamine (2.8 mL, 20 mmol) in THF at –78° C. was added n-butyllithium (6.7 mL of 2.5M solution, 17 mmol). To the resulting mixture was added a solution of 4-cyano-N-methyl-N-(4-picolyl)benzamide (3.5 g, 14 mmol) in THF. The resulting dark purple solution was stirred at –78° C. for 10 min, at which time benzoyl chloride (4.1 mL, 35 mmol) was added. The mixture was warmed to room temperature over 30 min, then poured into aqueous $NH_4Cl$. The mixture was extracted with $Et_2O$, and the organic extract was evaporated under reduced pressure. The residue was triturated with $Et_2O$ to provide an orange solid which was washed sparingly with acetone and copiously with $Et_2O$. The title compound was obtained as a bright yellow solid (1.6 g, 25%): $^1$H NMR ($CDCl_3$): d 7.81–7.09 (m, 16H); 6.49 (m, 2H); 3.32 (s, 3H).

(c) 2-(4-Cyanophenyl)-1-methyl-4-phenyl-5-(4-pyridyl) imidazole—To a solution of 4-cyano-N-[N"-a-dibenzoyl-1,4-dihydropyridylmethylenyl]-N-methylbenzamide (1.5 g, 3.3 mmol) in acetic acid (50 mL) was added ammonium acetate (1.5 g, 19.5 mmol). The resulting mixture was heated at reflux for 18 h, then allowed to cool and was concentrated. The residue was suspended in $CH_2Cl_2$ and filtered. The filtrate was evaporated and the residue was triturated with MeOH to afford the title compound as a whim crystalline solid (0.72 g, 64%): mp 176°–177° C.

Example 4

2-(4-Aminomethylphenyl)-1-methyl-4-phenyl-5-(4-pyridyl)-imidazole (a) To a solution of 2-(4-cyanophenyl)-1-methyl-4-phenyl-5-(4-pyridyl)imidazole (0.20 g, 0.6 mmol) [See Ex. 3 above] in THF (10 mL) was added $LiAlH_4$ (0.60 mL of 1.0M solution in THF, 0.6 mmol), and the resulting mixture was stirred at rt for 1 h. The mixture was then poured into 2.5N NaOH and extracted with $Et_2O$. The organic extract was evaporated, and the residue was purified by flash chromatography, eluting first with a solvent gradient of 0–10% MeOH/$CHCl_3$, followed by 1:10:90 $NH_4OH$/MeOH/$CHCl_3$. Trituration with ether afforded the title compound as a white solid (66 mg, 32%): CIMS ($NH_3$, m/z): 341 ($M^+$+H).

Example 5

4-[1-Methyl-4-phenyl-5(4-pyridyl)-imidazol-2-yl]benzoic acid, sodium salt

A mixture of 2-(4-cyanophenyl)-1-methyl-4-phenyl5(4-pyridyl)-imidazole (0.10 g, 0.3 mmol) [See Ex. 3 above] in 6N HCl (3 mL) was heated at reflux for 24 h, then allowed to cool The pH was adjusted to 7, and the solid which formed was collected by filtration and washed successively with $H_2O$, acetone and $Et_2O$ to provide the title compound as a white solid (25 mg, 23%): CIMS ($NH_3$, m/z): 356 ($M^+$+H).

Example 6

2-(4-Acetamidomethyphenyl)-1-methyl-4-phenyl-5-(4-pyridyl)imidazole

To a solution of 2-(4-aminomethylphenyl)-1-methyl-4-phenyl-5-(4-pyridyl)imidazole (30 mg, 0.09 mmol) [See Ex. 4 above] in pyridine (3 mL) was added acetic anhydride (0.30 mL, 3.18 mmol). The resulting solution was stirred at rt for 30 min, then concentrated under reduced pressure. The residue was purified by flash chromatography, eluting with a solvent gradient of 0–2% MeOH/CHCl$_3$. The isolated material was triturated with Et$_2$O to provide an off-white solid (10 mg, 28%) which was recrystallized from EtOAc to provide the title compound: mp 210°–211° C.

Example 7

Methyl-4-[1-methyl-4-phenyl-5-(4-pyridyl)-imidazol-2-yl]benzoate

To a suspension of 4-[1-methyl-4-phenyl-5-(4pyridyl)-imidazol-2-yl]benzoic acid, sodium salt (20 mg, 0.06 mmol) [See Ex. 5 above] in CH$_2$Cl$_2$ (2 mL) was added triethylamine (24 mL, 0.17 mmol), followed by thionyl chloride (10 mL, 0.14 mmol). The reaction mixture was stirred at rt for 30 min, at which time MeOH (0.5 mL) was added. The mixture was stirred at rt for an additional 2 h and concentrated under reduced pressure. The residue was purified by flash chromatography, eluting with a solvent gradient of 0–1% MeOH/CHCl$_3$ and recrystallized from EtOAc to afford the title compound as an off-white crystalline solid (1.6 mg, 8%): mp 208°–209° C.

Example 8(a)

(a)-4-(4-Fluorophenyl)-N-1-hydroxy-2-(4-hydroxyphenyl)-5-(4-pyridyl)imidazole

The title compound was prepared using the same procedure as described in Example 10, step (d) except using 4-hydroxy-benzaldehyde.

Example 8(b)

(b) 4-(4-Fluorophenyl)-2-(4-hydroxyphenyl)-5-(4-pyridyl)-1H-imidazole

The title compound was prepared using the same procedure as described in Example 1, except using 4-(4-fluorophenyl)-N-1-hydroxy-2-(4-hydroxyphenyl)-5-(4-pyridyl)imidazole (see Ex. 8a): mp 214°–215° C.

Example 9

4-[4-(4-Fluorophenyl)-5-(4-pyridyl)-1H-imidazol-2-yl]benzoic acid

A solution containing 2-(4-cyanophenyl)-4-(4-fluorophenyl)-5-(4-pyridyl)-1H-imidazole (9.6 g, 28 mmol) [See Ex. 1 above] in concentrated HCl (100 mL) was heated at reflux for 18 h. After cooling, the pH was adjusted to neutral by the addition of 50% aqueous NaOH. The solid which formed was collected by filtration and washed successively with H$_2$O, acetone and Et$_2$O. A portion of the solid (5 g) was dissolved in MeOH and filtered under reduced pressure through a pad of silica gel, eluting with a solvent gradient of 4–10 % MeOH/CHCl$_3$, followed by 2:20:80 H$_2$O/MeOH/CHCl$_3$. The title compound was isolated as a yellow solid, which was re-crystallized from MeOH/CH$_2$Cl$_2$ (1.2 g, 30% adjusted yield): mp 289°–290° C.

Example 10

2-(4-Cyanophenyl)-4-(4-fluorophenyl)-1-N-hydroxy-5-(4-pyridyl)imidazole (a) 4-Fluoro-N-methoxy-N-methylbenzamide—To a mixture containing methoxymethylamine hydrochloride (44 g, 0.45 mol) and triethylamine (138 mL, 0.99 mol) in CH$_2$Cl$_2$ (500 mL) at 0° C. was added over 30 min, 4-fluorobenzoyl chloride (50 mL, 0.41 mol). The result-ing mixture was allowed to warm to rt and stirring was continued for 30 min, at which time the mixture was poured into H$_2$O and extracted with Et$_2$O. The organic extract was washed with saturated aqueous NaCl and dried (MgSO$_4$). Removal of the solvent in vacuo afforded the title compound (80 g, 100%), which was used without further purification: $^1$H NMR (CDCl$_3$): d 7.72 (dd, 2H); 7.06 (apparent t, 2H); 3.52 (s, 3H); 3.43 (s, 3H).

(b) 4-Fluoro-2-(4-pyridyl)acetophenone—A solution of lithium diisopropylamide was prepared at –78° C. in the usual manner from diisopropylamine (21 ml, 0.15 mol) and n-butyllithium (54 mL of 2.5M solution in hexanes, 0.135 mol), and to this was added at –78° C., 4-picoline (10 g, 0.108 mol). After stirring an additional 15 min at –78° C., 4-fluoro-N-methoxy-N-methylbenzamide (20 g, 0.109 mol) was added, and the mixture was allowed to slowly warm to rt. The reaction mixture was poured into saturated aqueous NaCl and extracted with 4:1 THF/CH$_2$Cl$_2$, and the organic extract was dried (MgSO$_4$). The solvent was removed in vacuo, and to the oily brown residue was added Et$_2$O. The title compound was obtained as a brown solid (16.8 g, 72%) which was recrystallized from Et$_2$O/Hex: $^1$H NMR (CDCl$_3$): d 8.55 (d, 2H); 8.03 (dd, 2H); 7.16 (m, 4H); 4.24 (s, 2H).

(c) 4-Fluoro-2-hydroxyimino-2-(4-pyridyl)acetophenone—The title compound was prepared using the same procedure (U.S. Pat. No. 3,940,486) employed to prepare 2-hydroxyimino-2-(4-pyridyl)acetophenone, except using 4-fluoro-2-(4-pyridyl)-acetophenone.

(d) 2-(4-Cyanophenyl)-4-(4-fluorophenyl)-N-1-hydroxy-5-(4-pyridyl)imidazole

The title compound was prepared using the same procedure (U.S. Pat. No. 3,940,486) employed to prepare 2-(t-butyl)-4-(phenyl)-N-1-hydroxy-5-(4-pyridyl)imidazole, except using 4-fluoro-2-hydroxyimino-2-(4-pyridyl)acetophenone and 4-cyanobenzaldehyde: $^1$H NMR (CDCl$_3$): d 8.27 (d, 2H); 7,94 (d, 2H); 7.72 (d, 2H); 7.35 (d, 2H); 7.30 (dd, 2H); 6.96 (t, 2H).

Example 11

2-(4-Aminomethylphenyl)-4-(4-fluorophenyl)-5-(4-pyridyl)-1H-imidazole

To a solution of 2-(4-cyanophenyl)-4-(4-fluorophenyl)-5-(4-pyridyl)-1H-imidazole. (2.5 g, 7.3 mmol) [See Ex. 1 above] in THF (50 mL) was added LiAlH$_4$ (7.3 mL of 1M solution in THF, 7.3 mmol), and the resulting mixture was heated at reflux for 2 h, at which time tlc analysis indicated that the reaction was incomplete. Additional LiAlH$_4$ (4.0 mL; 4.0 mmol) was added and heating was continued for 30 min. The mixture was allowed to cool, then poured into 2.5N NaOH and extracted with THF. The organic extract was washed with saturated aqueous NaCl and concentrated under reduced pressure. The residue was purified by flash chromatography, eluting with 9:1 CHCl$_3$/MeOH, followed by 90:10:1 CHCl$_3$/MeOH/NH$_3$. The material that was isolated was triturated with Et$_2$O to afford the title compound (1.5 g, 60%): mp 214°–215° C.

Example 12(a)

2-(4-Cyanophenyl)-4-(4-fluorophenyl)-N-1-hydroxy-5-(4-quinolyl)imidazole (a) 4-Fluoro-2-(4-quinolyl)acetophenone—The title compound was prepared using the same procedure as described in Example 10, step (b) except using 4-methylquinoline: $^1$H NMR (CDCl$_3$): d 8.87 (d, 1H); 8.13 (m, 3H); 7.86 (d, 1H); 7.73 (apparent br t, 1H); 7.56 (apparent br t, 1H); 7.28 (d, 1H); 7.20 (t, 2H); 4.71 (s, 2H).

(b) 4-Fluoro-2-hydroxyimino-2-(4-quinolyl)acetophenone—The title compound was prepared using the same procedure as described in Example 10, step (c) except using 4-fluoro-2-(4-quinolyl)acetophenone: $^1$H NMR (DMSO-d$_6$): d 9.00 (d, 1H); 8.15 (m, 3H); 7.78 (m, 1H); 7.61 (m, 2H); 7.50 (d, 1H); 7.42 (t, 2H).

(c) 2-(4-Cyanophenyl)-4-(4-fluorophenyl)-N-1-hydroxy-5-(4-quinolyl)imidazole

The title compound was prepared using the same procedure as described in Example 10, step (d) except using 4-fluoro-2-hydroxyimino-2-(4-quinolyl)acetophenone and 4-cyanobenzaldehyde: $^1$H NMR (CDCl$_3$): d 8.30 (d, 2H); 7.80 (d, 1H); 7.70 (two overlapping d, 3H); 7.46 (m, 2H); 7.36 (m, 1H); 7.11 (m, 2H); 7.0 (m, 1H); 6.75 (t, 2H).

Example 12(b)

2-(4-Cyanophenyl)-4-(4-fluorophenyl)-5-(4-quinolyl)-1H-imidazole

The title compound was prepared using the same procedure as described in Example 1, except using 2-(4-cyanophenyl)-4-(4-fluoro-phenyl)-N-1-hydroxy-5-(4-quinolyl)imidazole [see Ex. 12a]: mp 294°–295° C.

Example 13

2-(3,5-Dibromo-4-hydroxyphenyl)-4-(4-fluorophenyl)-5-(4-pyridyl)-1H-imidazole (a) 1-(4-fluorophenyl)-2-(4-pyridyl)-ethanediol To a stirring solution of 2.0 g (11.2 mmol) 4-(t-butyldimethyl-silyloxy)methyl pyridine in 8 ml of THF at −20° C. was added 14.7 mmol of lithium di-iso-propyl amide in THF. Thirty minutes later 4-fluoro-benzaldehyde (1.66 g, 13.4 mmol) was added at which point the solution was allowed to warm slowly to rt. The reaction was quenched with NH$_4$Cl and extracted with ether to afford the crude protected diol which following concentration was dissolved in THF and treated with 17 ml of a 1 molar solution of tetrabutylammonium fluoride in THF overnight. Standard aqueous workup afforded the crude diol which was further purified by column chromatography (hex/EtOAc) to yield 1.6 g (62%) of the titled material.

(b) 1-(4-fluorophenyl)-2-(4-pyridyl)ethanedione Oxidation of 1-(4-fluorophenyl)-2-(4-pyridyl)ethanediol according to the oxalyl chloride method of Swern [J. Org. Chem., 44, p 4148, 1979)] gave the titled dione following extractive workup and recrystallization from hexanes m.p. 85°–86.5° C.

(c) 2-(3,5-Dibromo-4-hydroxyphenyl)-4-(4-fluorophenyl)-5-(4-pyridyl)-1H-imidazole To a solution of 1-(4-fluorophenyl)-2-(4-pyridyl)ethanedione (0.25 g, 1.1 mmol) and 3,5-dibromo-4-hydroxy-benzaldehyde (0.37 g, 1.3 mmol) in glacial acetic acid (5 mL) was added ammonium acetate (0.50 g, 6.5 mmol), and the resulting mixture was heated at reflux for 18 h. After cooling, the mixture was poured into H$_2$O, and the pH was adjusted to neutral by the addition of 2.5N NaOH. The solid which formed was collected by filtration, washed with H$_2$O, dried in vacuo and purified by flash chromatography, eluting with a solvent gradient of 2–4% MeOH/CHCl$_3$. The title compound was obtained as a tan solid (15 mg, 3%): ESMS (m/z): 488 (M$^+$+H).

Example 14

Ethyl 4-[4-(4-Fluorophenyl)-5-(4-pyridyl)]-1H-imidazol-2-yl]-benzoate

A solution of 4-[4-(4-fluorophenyl)-5-(4-pyridyl)-1H-imidazol-2-yl]-benzoic acid (30 mg, 0.08 mmol) See Ex. 9 above] in 20% ethanolic HCl (5 mL) was heated at reflux for 24 h, cooled to rt and neutralized with 50% NaOH. The residue was collected and purified by flash chromatography eluting with a solvent gradient of 4–10% MeOH/CHCl$_3$. Trituration with Et$_2$O afforded the title compound as a white solid (3.2 g 66%). $^1$H NMR (CDCl$_3$/MeOH-d$_4$): d 8.45 (d, 2H); 8.12 (m, 4H); 7.52 (m, 4H); 7.15 (t, 2H); 4.42 (q, 2H); 1.43 (t, 3H).

Example 15

2-[3,5-Dimethyl-4-hydroxy(phenyl)]-4-(4-fluorophenyl)-5-(4-pyridyl)-1H-imidazole The title compound was prepared using the same procedure as described in Example 13, except using 3,5-dimethyl-4-hydroxybenzaldehyde: ESMS (m/z): 360 (M$^+$+H).

Example 16

4-(4-Fluorophenyl)-2-(2-hydroxyphenyl)-5-(4-pyridyl)-1H-imidazole

The title compound was prepared using the same procedure as described in Example 13, except using salicylaldehyde: ESMS (m/z): 332 (M$^+$+H).

Example 17

4-(4-Fluorophenyl)-2-(4-methylthiophenyl)-5-(4-pyridyl)-1H-imidazole

The title compound was prepared using the same procedure as described in Example 13, except using 4-(methylthio)-benzaldehyde: ESMS (m/z): 362 (M$^+$+H).

Example 18

Methyl 4-[4-(4-fluorophenyl)-5-(4-pyridyl)-1H-imidazol-2-yl]-benzoate

A mixture containing 4-[4-(4-fluorophenyl)-5-(4-pyridyl)-1H-imidazol-2-yl]benzoic acid, sodium salt (0.20 g, 0.5 mmol) [See Ex. 9 above] and concentrated HCl (10 drops) in MeOH (5 mL) was heated at reflux for 8 h. After cooling, the pH was adjusted to neutral by the addition of 2.5N NaOH, and the solid which formed was collected by filtration, washed with H$_2$O and dried in vacuo. The title compound was obtained as a yellow solid (0.14 g, 76%) and was recrystallized from EtOAc/CH$_2$Cl$_2$:

$^1$H NMR (CDCl$_3$/MeOH-d$_4$): d 8.36 (d, 2H); 8.03 (m, 4H); 7.60–7.30 (m, 4H); 707 (t, 2H); 3.84 (s,3H).

Example 19

4-(4-Fluorophenyl)-2-(4-methylsulfonylphenyl)-5-(4-pyridyl)-1H-imidazole

To a solution of 4-(4-fluorophenyl)-2-(4-methylsulfinylphenyl)-5-(4-pyridyl)-1H-imidazole (3.7 g, 9.8 mmol) [See Ex. 20 below] in 1:10 3N HCl/H$_2$O (88 mL) was added a solution of KMnO$_4$ (1.5 g, 9.8 mmol) in H$_2$O (15 mL). After stirring at rt for 1 h, additional KMnO$_4$ (0.15 g, 0.9 mmol) was added, and stirring was continued for 15 min. The mixture was then poured into saturated aqueous Na$_2$SO$_3$ (200 mL), and the pH was adjusted to slightly acidic by the addition of 3N HCl, then to neutral by the addition of 2.5N NaOH. The solid which formed was collected by filtration, washed successively with H$_2$O and MeOH and recrystallized three times from MeOH to afford the title compound (0.63 g, 16%): mp 148°–149° C.

Example 20

4-(4-Fluorophenyl)-2-(4-methylsulfinylphenyl)-5-(4-pyridyl)-1H-imidazole

To a solution of 4-(4-fluorophenyl)-2-(4-methylthiophenyl)-5-(4-pyridyl)-1H-imidazole (0.80 g, 2.2 mmol) [See Ex. 17 above] in glacial acetic acid (15 mL) was added a solution of K$_2$S$_2$O$_8$ (0.72 g, 2.6 mmol) in H$_2$O (20 mL). Additional glacial acetic acid (15 mL) was added to ensure homogeneity, and the resulting solution was stirred at rt for 18 h. The mixture was then poured in to H$_2$O, and the pH was adjusted to neutral by the addition of conc. NH$_4$OH. The solid which formed was collected by filtration to afford the title com-pound (0.65 g, 78%) as a tan solid, which was recrystallized from MeOH: mp 250°–252° C.

Example 21

N,N-Dimethyl-4-[4-(4-fluorophenyl)-5-(4-pyridyl)-1H-imidazol-2-yl]-benzamide

To dimethylamino(methyl)aluminum chloride (0.60 mL of 0.67M solution in toluene, 0.40 mmol) was added a solution of methyl 4-[4-(4-fluorophenyl)-5-(4-pyridyl)-1H-imidazol-2-yl]-benzoate (50 mg, 0.13 mmol) [See Ex. 18 above] in 1,2-dichloroethane (5 mL). The resulting mixture was heated at reflux for 4 h, then allowed to cool and was poured into 2.5N NaOH. The mixture was extracted with EtOAc, and the organic extract was washed with saturated aqueous NaCl and dried (MgSO$_4$). The solvent was removed in vacuo, and the residue was purified by flash chromatography, eluting with a solvent gradient of 2–4% MeOH/CHCl$_3$ to afford the title compound (25 mg, 50%) as a white solid: CIMS (NH$_3$, m/z ): 387 (M$^+$+H).

Example 22

2-[(4-N,N-Dimethyl)aminomethylphenyl]-4-(4-fluorophenyl)-5-(4-pyridyl)-1H-imidazole The title compound was prepared using the same procedure as described in Example 11, except using N,N-dimethyl-4-[4-(4-fluorophenyl)-5-(4-pyridyl)-1H-imidazol-2-yl]benzamide: CIMS (NH$_3$, m/z): 373 (M$^+$+H).

Example 23

2-[4-(Dimethylamino)phenyl]-4-(4-fluorophenyl)-5-(4-pyridyl)-1H-imidazole

The title compound was prepared using the same procedure as described in Example 13, except using 4-(N,N-dimethylamino)benzaldehyde: ESMS (m/z): 359 (M$^+$+H).

Example 24

4-(4-Fluorophenyl)-2-phenyl-5-(4-pyridyl)-1H-imidazole

The title compound was prepared using the same procedure as described in Example 13, except using benzaldehyde: ESMS (m/z): 316 (M$^+$+H).

Example 25

2-[4-(3-Dimethylaminopropoxy)phenyl]-4-(4-fluorophenyl)-5-(4-pyridyl)-1H-imidazole The title compound was prepared using the same procedure as described in Example 13, except using 4-(3-dimethylamino-propoxy)benzaldehyde: ESMS (m/z): 417 (M$^+$+H).

Example 26

4-(4-Fluorophenyl)-2-(4-nitrophenyl)-5-(4-pyridyl)-1H-imidazole

The title compound was prepared using the same procedure as described in Example 13, except using 4-nitrobenzaldehyde: ESMS (m/z): 359 (M$^+$+H).

Example 27

N,N-Dimethyl-4-[2-(4-fluorophenyl)-5-(4-pyridyl)-1H-imidazol-2-yl]benzoyl-oxyacetamide a) Methyl benzylglycolate—To a solution containing methyl glycolate (2.5 mL, 32 mmol) and trifluoromethylsulfonic acid (150 mL) in CH$_2$Cl$_2$ (10 mL) was added benzyl 2,2,2-trichloro-acetimidate (7.0 mL, 37 mmol). After stirring for several min, the mixture was poured into aqueous NaHCO$_3$ and extracted with Et$_2$O. The organic extract was washed with saturated aqueous NaCl, dried (MgSO$_4$) and concentrated under reduced pressure. The residue was purified by flash chromatography, eluting with a solvent gradient of 9–17% EtOAC/Hex to afford the title compound: $^1$H NMR (CDCl$_3$): d 7.34 (m, 5H); 4.62 (s, 2H); 4.11 (s, 2H); 3.78 (s, 3H).

(b) Benzyl-N,N-dimethylglycolamide—To dimethylamino(methyl)aluminum chloride [prepared from dimethylamine hydrochloride (3.4 g, 42 mmoL) and trimethyl aluminum (21 mL of 2M solution, 42 mmol)] in toluene (40 mL) was added methyl benzylglycolate (3.0 g, 17 mmol). After stirring at rt for 1.5 h, the mixture was poured into 3N HCl and extracted with Et$_2$O. The organic extract was washed with saturated aqueous NaCl, dried (MgSO$_4$) and concentrated under reduced pressure. The residue was purified by flash chromatography, eluting with a solvent gradient of 9–50% EtOAc/Hex. The title compound was obtained as a colorless oil (1.2 g, 37%): $^1$H NMR (CDCl$_3$): d 7.4–7.1 (m, 5H); 4.61 (s, 2H); 4.18 (s, 2H); 2.98 (s, 3H); 2.95 (s, 3H).

(c) N,N-Dimethylglycolamide—To a solution of benzyl-N,N-dimethylglycolamide (0.28 g, 1.5 mmol) in MeOH (5 mL) was added 10% palladium on activated carbon (0.15 g), and the resulting mixture was stirred under an atmosphere of H$_2$. After 1 h, the mixture was filtered through a pad of Celite, and the filtrate was concentrated under reduced pressure to afford the title compound which was used without further purification: $^1$H NMR (CDCl$_3$): d 4.13 (s, 2H); 3.01 (s, 3H); 2.89 (s, 3H).

(d) N,N-Dimethyl-4-[4-(4-fluorophenyl)-5-(4-pyridyl)-1H-imidazol-2-yl]-benzoyl-oxyacetamide—To a solution of 4-[4-(4-fluorophenyl)-5-(4-pyridyl)-1H-imidazol-2-yl] benzoic acid (0.15 g, 0.42 mmol) [See Ex. 9 above] in DMF(10 ml) was added carbonyldiimidazole (0.34 g, 2.1 mmol). After stirring for 18 h at rt, N,N-dimethylglycolamide (0.43 g, 4.2 mmol) was added and stirring was continued for an additional 3h at rt. The reaction mixture was poured into H$_2$O, extracted with EtOAc and evaporated. The residue was purified by flash chromatography eluting with a solvent gradient of 2% MeOH/CHCl$_3$ to afford the title compound: CIMS (NH$_3$, m/z): 445 (M$^+$+H).

Example 28

2-(4-Aminophenyl)-4-(4-fluorophenyl)-5-(4-pyridyl)-1H-imidazole

A mixture containing 4-(4-fluorophenyl)-2-(4-nitrophenyl)-5-(4-pyridyl)-1H-imidazole (2.0 g, 5.6 mmol) [See Ex. 26 above] and 10% palladium on activated carbon (0.4 g) was stirred under an atmosphere of $H_2$ for 4 h, then was filtered through a pad of Celite. The filtrate was concentrated under reduced pressure, and the residue was purified by flash chromatography, eluting with a solvent gradient of 1–10% MeOH/CHCl$_3$. The title compound was obtained as a light orange solid (0.50 g, 27%): $^1$H NMR (DMSO-d$_6$): d 8.40 (d, 2H); 7.73 (d, 2H); 7.57 (m, 2H); 7.35 (m, 4H); 6.62 (t, 2H).

Example 29

4-(4-Fluorophenyl)-2-(4-methanesulfonamidophenyl)-5-(4-pyridyl)-1H-imidazole

To a suspension of 2-(4-aminophenyl)-4-(4-fluorophenyl)-5-(4-pyridyl)-1H-imidazole (80 mg, 0.24 mmol) [See Ex. 28 above] and triethylamine (0.12 mL, 0.86 mmol) in CH$_2$Cl$_2$ (5 mL) was added methanesulfonyl chloride (55 mL, 0.72 mmol). After stirring at rt for 1 h, the mixture was poured into aqueous NaHCO$_3$ and extracted with EtOAc. The organic extract was washed with saturated aqueous NaCl, dried (MgSO$_4$) and concentrated under reduced pressure. The residue was purified by flash chromatography, eluting with a solvent gradient of 2–10%. MeOH/CHCl$_3$ to afford the title compound as a tan solid (35 mg, 36%): ESMS (m/z): 409 (M$^+$+H).

Example 30

4-[4-(4-Fluorophenyl)-5-(4-pyridyl)-1H-imidazol-2-yl]phenyl-sulfonamide (a) Ethyl 4-sulfonamidobenzoate—A solution of 4-carboxybenzenesulfonamide (5.0 g, 0.025 mol) in 20% ethanolic HCl (20 mL) was heated at reflux for 18 h, then allowed to cool and was concentrated under reduced pressure to afford the title compound: $^1$H NMR (CDCl$_3$): d 8.20 (apparent d, 2H); 8.00 (apparent d, 2H); 4.88 (br s, 2H); 4.43 (q, 2H); 1.43 (t, 3H).

(b) N-Methoxy-N-methyl-4-sulfonamidobenzamide—To a solution of methoxymethylamino(methyl)aluminum chloride [prepared from methoxymethylamine hydrochloride (4.8 g, 50 mmoL) and trimethyl aluminum (25 mL of 2M solution, 50 mmol)] in toluene (50 mL) at 0° C. was added ethyl 4-sulfonamidobenzoate (3.8 g, 17 mmol). The mixture was allowed to warm to rt and stir for 3 h, then was poured into a slurry of silica gel (50 g) in CHCl$_3$ (200 mL). The mixture was filtered, and the filtrate was concentrated under reduced pressure. The residue was poured into H$_2$O, and the solid which formed was collected by filtration, washed with H$_2$O and dried in vacuo to afford the title compound (1.7 g, 42%): $^1$H NMR (CDCl$_3$/MeOH-d$_4$): d 7.86 (d, 2H); 7.66 (d, 2H); 3.43 (s, 3H); 3.29 (s, 3H (c) 4-Formylbenzenesulfonamide—To a solution of N-methoxy-N-methyl-4-sulfonamidobenzamide (1.0 g, 4.1 mmol) in THF (25 mL) at –78° C. was added LiAlH$_4$ (6.1 mL of 1M solution in THF, 6.1 mmol). After stirring at –78° C. for 30 min, the mixture was poured into a slurry of silica gel (50 g) in CHCl$_3$ (200 mL). The mixture was faltered and the filtrate was concentrated under reduced pressure. The residue was purified by flash chromatography, eluting with a solvent gradient of 2–10% MeOH/CHCl$_3$. The title compound was obtained as a white solid (0.12 g, 16%): $^1$H NMR (CDCl$_3$/MeOH-d$_4$): d 10.3 (s, 1H); 8.02 (d, 2H); 7.95 (d, 2H).

(d) 4-[4-(4-Fluorophenyl)-5-(4-pyridyl)-1H-imidazol-2yl]sulfonamide

The title compound was prepared using the same procedure as described in Example 13, except using 4-formylbenzene-sulfonamide: ESMS (m/z): 395 (M$^+$+H).

Example 31

N'-Cyano-N-4-[4-(fluorophenyl)-5-(4-pyridyl)-1H-imidazol-2-yl]benzylguanidine

To a suspension of 2-(4-aminomethylphenyl)-4-(4-fluorophenyl)-5-(4-pyridyl)-1H-imidazole (0.10 g, 0.29 mmol) [See Ex. 11 above] in CH$_3$CN was added diphenyl cyanocarbonimidate (83 mg, 0.35 mmol). After stirring at rt for 18 h, the solid which formed was collected by filtration and washed with CH$_3$CN. The solid was dissolved in MeOH saturated with NH$_3$ and stirred for 72 h. The mixture was concentrated under reduced pressure, and the residue was purified by flash chromatography, eluting with a solvent gradient of 4–10% MeOH/CHCl$_3$. The title compound was isolated as a pale yellow solid (22 mg, 18%): mp 280°–281° C.

Example 32

2-[4-(Methanesulfonamido)methylphenyl]-4-(4-fluorophenyl)-5-(4-pyridyl)-1H-imidazole The title compound was prepared using the same procedure as described in Example 29, except using 2-(4-aminomethylphenyl)-4-(4-fluorophenyl)-5-(4-pyridyl)-1H-imidazole [See Ex. 11 above]: ESMS (m/z): 423 (M$^+$+H).

Example 33

4-(4-Fluorophenyl)-2-(4-methoxyphenyl)-5-(4-pyridyl)-1H-imidazole (a) 1-Cyano-1-(4-pyridyl)methyl 4-methoxybenzoate The title compound was prepared using the same procedure Lantos, I. et al. (J. Med. Chem. 1984, 27, 72–75) employed to prepare 1-cyano-1(4-pyridyl)-methyl benzoate, except using 4-methoxybenzoyl chloride: $^1$H NMR (CDCl$_3$): d 8.81 (d, 2H); 8.10 (d, 2H); 7.57 (d, 2H); 7.01 (d, 2H); 6.74 (s, 1H); 3.93 (s, 3H).

(b) 1-(4-Fluorophenyl)-2-(4-pyridyl)-2-oxoethyl 4-methoxybenzoate and 2-(4-fluorophenyl)-1-(4-pyridyl)-2-oxoethyl 4-methoxybenzoate—The title compounds were prepared using the same procedure Lantos et al. (J. Med. Chem. 1984, 27, 72–75) used to prepare 1-(4-Fluorophenyl)-2-(4-pyridyl)-2-oxoethyl benzoate and 2-(4-fluorophenyl)-1-(4-pyridyl)-2-oxoethyl benzoate, except using 1-Cyano-1-(4-pyridyl)methyl 4-methoxybenzoate: $^1$H NMR (faster eluting isomer, CDCl$_3$): d 8.78 (d, 2H); 8.03 (br d, 2H); 7.73 (d, 2H); 7.53 (dd, 2H); 7.10 (apparent t, 2H); 6.93 (overlapping s and d, 3H); 3.85 (s, 3H); $^1$H NMR (slower eluting isomer, CDCl$_3$): d 8.66 (d, 2H); 8.04 (m, 4H); 7.46 (d, 2H); 7.15 (apparent t, 2H); 6.95 (overlapping s and d, 3H); 3.87 (s, 3H).

(c) 4-(4-Fluorophenyl)-2-(4-methoxyphenyl)-5-(4-pyridyl)-1H-imidazole—To a solution containing a mixture of 1-(4-fluorophenyl)-2-(4-pyridyl)-2-oxoethyl 4-methoxybenzoate and 2-(4-fluorophenyl)-1-(4-pyridyl)-2-oxoethyl-4-methoxybenzoate (0.35 g, 0.96 mmol) in glacial acetic acid (7.5 mL) was added ammonium acetate (0.35 g, 4.5 mmol). The resulting mixture was heated at reflux for 18 h, then allowed to cool. The mixture was concentrated under reduced pressure, and the residue was purified by flash chromatography, eluting with a solvent gradient of 33–60% EtOAc/Hex. The material which was isolated was recrystallized from MeOH/CH$_2$Cl$_2$ to provide the title compound (65 mg, 20%) as an off-white solid: mp 264°–265° C.

Example 34

2-(4-Amino-3-iodophenyl)-4-(4-fluorophenyl)-5-(4-pyridyl)-1H-imidazole

To a solution of 2-(4-aminophenyl)-4-(4-fluorophenyl)-5-(4-pyridyl)-1H-imidazole (50 mg, 0.15 mmol) [See Ex. 28 above] in glacial acetic acid (5 mL) was added a solution of ICl (24 mg, 0.15 mmol) in glacial acetic acid (1.5 mL). The resulting mixture was stirred at rt for 1 h, then poured into saturated aqueous Na$_2$S$_2$O$_5$. The pH was adjusted to neutral by the addition of 2.5N NaOH and extracted with EtOAc. The organic extract was concentrated under reduced pressure, and the residue was purified by flash chromatography, eluting with a solvent gradient of 2–10% MeOH/CHCl$_3$. The material that was isolated was recrystallized from Et$_2$O/Hex to afford the title compound: $^1$H NMR (CDCl$_3$): d 8.42 (d, 2H); 8.18 (d, 1H); 7.68 (dd, 2H); 7.42 (m, 4H); 7.09 (t, 2H); 6.77 (d, 1H).

Example 35

N-Benzyl-N-methyl-4-[4-(4-fluorophenyl-5-(4-pyridyl)-1H-imidazol-2-yl]benzamide

The title compound was prepared using the same procedure as described in Exp. 21, except using benzylmethylaminodimethyl aluminium and methyl 4-[4-(4-fluorophenyl)-5-(4-pyridyl)-1H-imidazol-2-yl]-benzoate [See Ex. 18 above]: mp 233°–234° C.

Example 36

2-[4-(N-Benzyl-N-methyl)aminomethylphenyl]-4-(4-fluorophenyl)-5-(4-pyridyl)-1H-imidazole The the compound was prepared using the same procedure as described in Example 11, except using N-benzyl-N-methyl-4-[4-(4-fluorophenyl)-5-(4-pyridyl)-1H-imidazol-2-yl]benzamide [See Ex. 35 above]: ESMS (m/z): 449 (M$^+$+H).

Example 37(a)

4-(4-Fluorophenyl)-N-1-hydroxy-2-(4-methylthiophenyl)-5-(4-quinolyl)imidazole (a) 4-Fluoro-2-(4-quinolyl)acetophenone The title compound was prepared using the same procedure as described in Example 10, step (b) except using 4-methylquinoline: $^1$H NMR (CDCl$_3$): d 8.87 (d, 1H); 8.10 (m, 3H); 7.88 (d, 1H); 7.74 (br t, 1H); 7.57 (br t, 1H); 7.20 (m, 3H); 4.73 (s, 2H).

(b) 4-Fluoro-2-hydroxyimino-2-(4-quinolyl) acetophenone—The title compound was prepared using the same procedure as described in Example 10, step (c) except using 4-fluoro-2-(4-quinolyl)acetophenone.

(c) 4-(4-1-Fluorophenyl)-N-1-hydroxy-2-(4-methylthiophenyl)-5-($_4$-quinolyl)imidazole—The title compound was prepared using the same procedure as described in Example 10, step (d) except using 4-fluoro-2-hydroxyimino-2-(4-quinolyl)acetophenone and 4-(methylthio)benzaldehyde: $^1$H NMR (CDCl$_3$): d 8.03 (m, 1H); 7.80 (br d, 2H); 7.52 (d, 1H); 7.40–7.10 (m, 5H); 6.81 (br m, 3H); 6.61 (apparent t, 2H), 2.48 (s, 3H).

Example 37(b)

4-(4-Fluorophenyl)-2-(4-methylthiophenyl)-5-(4-quinolyl)-1H-imidazole

The title compound was prepared using the same procedure as described in Example 1, except using 4-(4-fluorophenyl)-N-1-hydroxy-2-(4-methylthiophenyl)-5-(4-quinolyl)imidazole: ESMS (m/z): 412 (M$^+$+H).

Example 38

4-(4-Fluorophenyl)-2-(4-methylsulfinylphenyl)-5-(4-quinolyl)-1H-imidazole

The title compound was prepared using the same procedure as described in Example 20, except using 4-(4-fluorophenyl)-2-(4-methylthiophenyl)-5-(4-quinolyl)-1H-imidazole: ESMS (m/z): 428 (M$^+$+H).

Example 39

4-(3-Chlorophenyl)-2-(4-methylsulfinylphenyl)-5-(4-pyridyl)- 1H-imidazole

The title compound was prepared using the same procedure as described in Example 20, except using 4-(3-chlorophenyl)-2-(4-methylthiophenyl)-5-(4-pyridyl)-1H-imidazole [See Ex. 40 below]: ESMS (m/z): 394 (M$^+$+H).

Example 40(a)

4-(3-Chlorophenyl)-N-1-hydroxy-2-(4-methylthio-phenyl)-5-(4-pyridyl)-1H-imidazole (a) 3-Chloro-N-methoxy-N-methylbenzamide—The title compound was prepared using the same procedure as described in Example 10(a) except using 3-chlorobenzoyl chloride: $^1$H NMR (CDCl$_3$): d 7.69 (br s; 1H); 7.58 (br d, 1H); 7.42 (br d, 1H); 7.31 (dd, 1H); 3.55 (s, 3H); 3.34 (s, 3H).

(b) 3-Chloro-2-(4-pyridyl)acetophenone—The title compound was prepared using the same procedure as described in Example 10, step (b) except using 4-picoline and 3-chloro-N-methoxy-N-methylbenzamide: $^1$H NMR (CDCl$_3$): d 8.60 (d, 2H); 8.00 (br s, 1H); 7.89 (br d, 1H); 7.60 (br d, 1H); 7.45 (t, 1H); 7.21 (d, 2H); 4.27 (s, 2H).

(c) 3-Chloro-2-hydroxyimino-2-(4-pyridyl) acetophenone—The title compound was prepared using the same procedure as described in Example 10, step (c) except using 3-chloro-2-(4-pyridyl)acetophenone.

(d) 4-(3-Chlorophenyl)-N-1-hydroxy-2-(4-methylthiophenyl)-5-(4-pyridyl)-1H-imidazole—The title compound was prepared using the same procedure as described in Example 10, step (d) except using 3-chloro-2-hydroxyimino-2-(4-pyridyl)acetophenone and 4-methylthiobenzaldehyde:

$^1$H NMR (CDCl$_3$): d 8.04 (d, 2H); 7.70 (d, 2H); 7.21–6.91 (m, 8H); 2.47 (s, 3H).

Example 40(b)

4-(3-Chlorophenyl)-2-(4-methylthiophenyl)-5-(4-pyridyl)-1H-imidazole

The title compound was prepared using the same procedure as described in Example 1, except using 4-(3-chlorophenyl)-N-1-hydroxy2-(4-methylthiophenyl)-5-(4-pyridyl)imidazole: ESMS (m/z): 378 (M$^+$+H).

Example 41

4-(4-Fluorophenyl)-2-(4-formamidomethylphenyl)-5-(4-pyridyl)-1H-imidazole -

Formic acid (10 ml) was added to acetic anhydride (20 mL) and the mixture was heated to 50° C. for 15 min. 2-(4-Aminomethyl-phenyl)-4-(4-fluorophenyl)-5-4-pyridyl) imidazole (0.25 g, 0.73 mmol) [See Ex. 11] was added and the reaction mixture was heated to 50° C. for 2 h. The solvent was evaporated and the residue was purified by flash chromatography, eluting with a solvent gradient of 4–10% MeOH/CHCl$_3$. The title compound was isolated as a tan solid (0.15 g, 55%): ESMS (m/z): 373 (M$^+$+H).

Example 42

4-[4-(4-Fluorophenyl)-5-(4-pyridyl)-1H-imidazol-2-yl]-benzohydroxamic acid

To a solution of O-benzyl-4-[4-(4-fluorophenyl)-5-(4-pyridyl)-1H-imazol-2-yl]benzohydroxamic acid (0.10 g, 0.22 mmol) [See Ex. 43 below] in ethanol (10 mL) was added 10 % palladium on carbon. After stirring under an atmosphere of H$_2$ for 18 h, the reaction mixture was filtered through celite and the solids were washed with ethanol. The combined filtrates were evaporated and the residue was recrystallized from 2-propanol to afford the title compound (0.040 g, 50%): ESMS (m/z): 375 (M$^+$+H).

Example 43

O-Benzyl-4-[4-(4-Fluorophenyl)-5-(4-pyridyl)-1H-imidazol-2-yl]-benzohydroxamic acid To a stirred suspension of O-benzyl-hydroxylamine hydrochloride (1.2 g, 7.8 mmol) in toluene (20 mL) at 0° C. was added trimethylaluminum (2.0M in toluene, 3.9 mL, 7.8 mmol). The reaction mixture was warmed to rt and stirring was continued at this temperature for 1 h. Ethyl 4-[4-(4-fluorophenyl)-5-(4-pyridyl)-1H-imidazol-2-yl]benzoate (1.0 g, 2.6 mmol) [See Ex. 14 above] was added and the reaction mixture was heated at reflux for 3 h. After cooling, the reaction was poured into 10% MeOH/CHCl$_3$ containing silica gel. The solids were removed by filtration and washed with 10% MeOH/CHCl$_3$. The combined washings were evaporated and the residue was purified by flash chromatography eluting with a solvent gradient of 1–10% MeOH/CHCl$_3$. Trituration with ether afforded the title compound as a white solid (0.25 g, 21%): $^1$HNMR (CDCl$_3$/MeOH-d$_4$): d 8.16 (d, :2H); 7.77 (d, 2H); 7.53 (d, 2H); 7.23 (m, 5H); 7.10 (m, 4H); 6.88 (t, 2H).

Example 44

4-[4-(4-Fluorophenyl)-5-(4-pyridyl)-1H-imidazol-2-yl] benzamidoxime

To a mixture of 2-(4-cyanophenyl)-4-(4-fluorophenyl)-5-(4-pyridyl)-1H-imidazole (3.0 g, 8.7 mmol) [See Ex. 1 above] and K$_2$CO$_3$ (2.4 g, 17 mmol) in EtOH (120 mL) and H$_2$O (6 mL) was added hydroxylamine hydrochloride (1.2 g, 17 mmol). After heating at reflux for 24 h, the reaction mixture was poured into H$_2$O. The precipitate was collected, washed with H$_2$O and air-dried. The crude product was dissolved in acetone, silica gel was added and the solvent was evaporated. The impregnated silica gel was added to the top of a flash column and the column was eluted with a solvent gradient of 2–10% MeOH/CHCl$_3$ to afford the title compound as a white solid (3.0 g, 91%): ESMS (m/z): 374 (M$^+$+H).

Example 45

N''-Methyl-N'-cyano-N-[4-(4-fluorophenyl)-5-(4-pyridyl)-1H-imidazol-2-yl]-benzylguanidine To a suspension of 2-(4-aminomethylphenyl)-4-(4-fluorophenyl)-5-(4-pyridyl)-1H-imidazole (2.5 g, 7.3 mmol) [See Ex. 11 above] in CH$_3$CN (250 mL) was added diphenyl cyanocarbonimidate (8.8 g, 7.3 mmol). After stirring at rt for 18 h, the solid which formed was collected by filtration and washed with CH$_3$CN (2.1 g, 59%). Without further purification, this material was added to methanol (100 mL) saturated with methylamine. The flask was stoppered and the reaction was stirred for 18 h at rt. The solvent and excess methylamine were evaporated and the residue was triturated with ether to give a brown solid which was further purified by flash chromatography eluting with a solvent gradient of 4–10% MeOH/CHCl$_3$ to afford the title compound as a tan solid (0.33 g, 78%): CIMS (NH3, m/z): 426 (M$^+$+H).

Example 46(a)

N-1-Hydroxy-4-(3-methoxyphenyl)-2-(4-methylthiophenyl)-5-(4-pyridyl)-1H-imidazole (a) 3-Methoxy-N-methoxy-N-methylbenzamide—The title compound was prepared using the same procedure as described in Example 10, step (a) except using m-anisoyl chloride: $^1$H NMR (CDCl$_3$): d 7.27 (m, 3H); 7.01 (m, 1H); 3.82 (s, 3H); 3.57 (s, 3H); 3.36 (s, 3H).

(b) 3-Methoxy-2-(4-pyridyl)acetophenone—The title compound was prepared using the same procedure as described in Example 10, step (b) except using 3-methoxy-N-methoxy-N-methylbenzamide: ESMS (m/z): 228.2 (M$^+$+H).

(c) 2-Hydroxyimino-3-methoxy-2-(4-pyridyl) acetophenone—The title compound was prepared using the same procedure as described in Example 10, step (c) except using 3-methoxy-2-(4-pyridyl)acetophenone.

(d) N-1-Hydroxy-4-(3-methoxyphenyl)-2-(4-methylthiophenyl)-5-(4-pyridyl)-1H-imidazole—The title compound was prepared using the same procedure as described in Example 10, step (d) except using 2-hydroxyimino-3-methoxy-2-(4-pyridyl)acetophenone and 4-(methylthio)-benzaldehyde: ESMS(m/z): 390 (M$^+$+H).

Example 46(b)

4-(3-Methoxyphenyl)-2-(4-methylthiophenyl)-5-(4-pyridyl) imidazole

The title compound was prepared using the same procedure as described in Example 1, except using N-1 -hydroxy-4-(3-methoxy-phenyl)-2-(4-methylthiophenyl)-5-(4-pyridyl)imidazole: mp 215.0°–216.0° C.

Example 47

4-(3-Methoxyphenyl)-2-(4-methylsulfinylphenyl)-5-(4-pyridyl)-1H-imidazole

The title compound was prepared using the same procedure as described in Example 38, except using 4-(3-methoxyphenyl)-2-(4-methylthiophenyl)-5-(4-pyridyl)-1H-imidazole [See Example 46 above]: mp 167°–168.5° C.

Example 48

Morpholino-4-[4-(4-fluorophenyl)-5-(4-pyridyl)-1H-imidazol-2-yl]benzamide

The title compound was prepared using the same procedure as described in Example 21 except using dimethylamino-(morpholino)aluminum chloride and ethyl 4-[4-(4-fluorophenyl)-5-(4-pyridyl)-1H-imidazol-2-yl]-benzoate [See Ex. 14 above]: ESMS (m/z): 429 (M⁺+H).

Example 49

4-(4-Fluorophenyl)-5-[4-(2-methylpyridyl)]-2-(4-methylthiophenyl)-1H-imidazole

The title compound was prepared using the same procedure as described in Example 13, except using 4-(4-fluorophenyl)-1-hydroxy-5-[4-(2-methylpyridyl)]-2-(4-methylthiophenyl)-imidazole [See Ex. 66 below]: ESMS (m/z): 376.2 (M⁺+H).

Example 50

4-(4-Fluorophenyl)-5-[4-(2-methylpyridyl)]-2-(4-methylsulfinylphenyl)-1H-imidazole The title compound was prepared using the same procedure as described in Example 20 except using 4-(4-fluorophenyl)-5-[4-(2-methylpyridyl)]-2-(4-methylthiophenyl)-1H-imidazole [See Ex. 49 above]: ESMS (m/z): 392.2 (M⁺+H).

Example 51(a)

4-(4-Fluorophenyl)-N-1-hydroxy-5-(4-pyrimidinyl)-imidazole (a) 4-Fluoro-2-(4-pyrimidinyl)acetophenone—The title compound was prepared using the same procedure as described in Example 10, step (b) except using 4-methylpyrimidine.

(b) 4-Fluoro-2-hydroxyimino-2-(4-pyrimidinyl)acetophenone—The title compound was prepared using the same procedure described in Example 10, step (c) except using 4-fluoro-2-(4-pyrimidinyl)acetophenone.

(c) 4-(4-Fluorophenyl)-N-1-hydroxy-5-(4-pyrimidinyl)imidazole—The title compound was prepared using the same procedure described in Example 10, step (d) except using 4-fluorophenyl-2-hydroxyimino-2-(4-pyrimidinyl) acetophenone.

Example 51(b)

4-(4-Fluorophenyl)-2-(4-methylthiophenyl)-5-(4-pyrimidinyl)-1H-imidazole

The title compound was prepared using the same procedure as described in Example 1, except using 4-(4-fluorophenyl)-N-1-hydroxy-5-(4-pyrimidinyl)imidazole: CIMS (NH₃, m/z): 3.63 (M⁺+H).

Example 52

4-(4-Fluorophenyl)-2-(4-methylsulfinylphenyl)-5-(4-pyrimidinyl)-1H-imidazole

The title compound was prepared using the same procedure described in Example 20, except using 4-(4-fluorophenyl)-2-(4-methylthio)phenyl)-5-(4-pyrimidinyl)-1H-imidazole: CIMS (NH₃, m/z): 379 (M⁺+H).

Example 53

4-(4-Fluorophenyl)-2-(4-methylsulfonylphenyl)-5-(4-pyrimidinyl)-1H-imidazole

To a solution of 4-(4-fluorophenyl)-2-(4-methylthiophenyl)-5-(4-pyrimidinyl)-1H-imidazole (0.10 g, 0.28 mmol) [See Ex. 51 above] was added 3-chloroperbenzoic acid (50%, 0.15 g, 0.42 mmol). After stirring at rt for 72 h, the solvent was evaporated and the residue was partitioned between EtOAc and 2.5N NaOH. The organic phase was washed with brine, dried (MgSO4) and evaporated. The residue was triturated with EtOAc to afford the title compound as a white solid (0.50 g, 46%). CIMS (NH₃, m/z): 395 (M⁺+H).

Example 54

4-(4-Fluorophenyl)-2-(4-Morpholinomethylphenyl)-5-(4-pyridyl)-1H-imidazole

The title compound was prepared using the same procedure as described in Example 11 except using morpholino-4-[4-(4-fluorophenyl)-5-(4-pyridyl)-1H-imidazol-2-yl]benzamide: mp 242°–243° C.

Example 55

4-(4-Fluorophenyl)-2-(4-hydroxymethyl)-5-(4-pyridyl)-1H-imidazole

To a suspension of ethyl 4-[4-(4-fluorophenyl)-5-(4-pyridyl)-1H-imidazol-2-yl]benzoate (1.0 g, 2.6 mmol) [See Ex. 14 above] in THF (25 mL) was added LiAlH₄ (1M in THF, 7.8 mL, 7.8 mmol). After stirring at rt for 0.5 h, the reaction mixture was poured into 2.5N NaOH and extracted three:times with 2:1 EtOAc/CH₂Cl₂. The combined extracts were washed with brine, dried (MgSO₄) and evaporated to afford the title compound as a white solid (0.50 g, 54%).

Example 56

4-[4-(4-Fluorophenyl)-5-(4-pyridyl)-1H-imidazol-2-yl]-benzaldehyde

To a suspension of 4-(4-fluorophenyl)-2-(4-hydroxymethyl)-5-(4-pyridyl)-1H-imidazole (0.40 g, 1.2 mmol) [See Ex. 55 above] in CH₂Cl₂ (40 mL) was added pyridinium chlorochromate (0.30 g, 1.4 mmol) at rt. The reaction mixture was stirred at this temperature for 2 h, filtered through a pad of silica gel eluting with 2% MeOH/CHCl₃ and the filtrate evaporate. The residue was purified by flash chromatography eluting with 4% MeOH/CHCl₃ followed by recrystallization from CH₂Cl₂/MeOH to afford the title compound as a white solid (0.30 g, 7.3%).

Example 57

4-(2-Methoxyphenyl)-2-(4-methylsulfinylphenyl)-5-(4-pyridyl)-1H-imidazole

The title compound was prepared using the same procedure as described in Example 20 except using 4-(2-methoxyphenyl)-2-(4-methylthiophenyl)-5-(4-pyridyl)-1H-imidazole [See Ex. 58 below]: CIMS (NH₃, m/z): 390 (M⁺+H).

Example 58(a)

N-1-Hydroxy-4-(2-methoxyphenyl)-2-(4-methylthiophenyl)-5-(4-pyridyl)imidazole (a) 2-Methoxy-N-methoxy-N-methylbenzamide—The title compound was prepared using the same procedure as described in Example 10, step (a) except using o-anisoyl chloride: ¹H NMR (CDCl₃): d 7.36 (m,3H); 6.98 (dd, 1H); 3.84 (s, 3H); 3.56(br s, 3H); 3.32(br s, 3H).

(b) 2-Methoxy-2-(4-pyridyl)acetophenone—The title compound was prepared using the same procedure as described in Example 10, step (b) except using 2-methoxy-N-methoxy-N-methylbenzamide.

(c) 2-Hydroxyimino-2-methoxy-2-(4-pyridyl) acetophenone—The title compound was prepared using the same procedure as described in Example 10, step (c) except using 2-methoxy-2-(4-pyridyl)acetophenone.

(d) N-1-Hydroxy-4-(2-methoxyphenyl)-2-(4-methylthiophenyl)-5-(4-pyridyl)imidazole—The title compound was prepared using the same procedure as described in Example 10, step (d) except using 2-hydroxyimino-2-methoxy-2-(4-pyridyl)acetophenone and 4-(methylthio) benzaldehyde: ESMS (m/z): 390.0 (M$^+$+H).

Example 58(b)

4-(2-Methoxyphenyl)-2-(4-methylthiophenyl)-5-(4-pyridyl)-1H-imidazole

The title compound was prepared using the same procedure as described in Example 1, except using N-1-hydroxy-4-(2-methoxyphenyl)-2-(4-methylthiophenyl)-5-(4-pyridyl) imidazole: CIMS (NH$_3$, m/z): 374.2 (M$^+$+H).

Example 59

3-[4-(4-Fluorophenyl)-5-(4-pyridyl)-1H-imidazol-2-yl] phenyl-5-methyl-4,5-dihydro-1,2,4-oxadiazole A solution of 4-[4-(4-Fluorophenyl)-5-(4-pyridyl)-1H-imidazol-2-yl]benzamide oxime (0.50 g, 1.3 mmol) [See Ex. 44 above] and acetaldehyde (25 mL) in ethanol (100 mL) and H$_2$O (100 mL) was stirred at rt for seven days. The solvent was evaporated and the residue was purified by flash chromatography eluting with a solvent gradient of 2–4% CHCl$_3$/MeOH. Recrystallization from EtOAc afforded the title compound as a yellow solid (0.11 g, 21%): CIMS (NH$_3$, m/z): 400 (M$^+$+H).

Example 60

3-[4-(4-Fluorophenyl)-5-(4-pyridyl)-1H-imidazol-2-yl] phenyl-5-methyl-1,2,4-oxadiazole To a solution of 4-[4-(4-fluorophenyl)-5-(4-pyridyl)-1H-imidazol-2-yl]benzamide oxime (0.10 g, 0.27 mmol) [See Ex. 44 above] in pyridine (10 mL) was added acetic anhydride (1.0 mL) at rt. After stirring at this temperature for 18 h, the reaction mixture was poured into H$_2$O, and the precipitate collected, washed with H$_2$O and dried in vacuo. Without further purification, the crude o-acylamidoxime was dissolved in acetic acid (5 ml) and heated at reflux for 3 h. The solvent was evaporated, H$_2$O was added and the mixture was neutralized with aqueous NaHCO$_3$. The precipitate was collected, washed With H$_2$O, air-dried and purified by flash chromatography eluting with 4% MeOH/CHCl$_3$. Trituration with ether afforded the title compound as a white solid (0.030 g, 28%): CIMS (NH$_3$, m/z): 398 (M$^+$+H).

Example 61

4-(3-Aminophenyl)-2-(4-methylthiophenyl)-5-(4-pyridyl)-1H-imidazole

A solution of 0.161 g (0.41 mmol) of 2-(4-methylthiophenyl)-4-(3-nitrophenyl)-5-(4-pyridyl)-1H-imidazole [See Ex. 62 below] in 3.4 mL of HOAc-H$_2$O (1:1) was treated with 1.81 mL (2.87 mmol) of 20% aqueous titanium (III) chloride in one single portion. The mixture was stirred at rt for 20 min, then made basic with 10% NaOH. The aqueous mixture was extracted with 95:5 CH$_2$Cl$_2$/MeOH. The organic extracts were washed with H$_2$O and saturated NaCl. Evaporation of solvent in vacuo afforded a yellow solid which was filtered through a plug of silica gel, eluting with 90:10 CHCl$_3$/MeOH. The title compound was isolated as a pale yellow solid (0.129 g, 78%): CIMS (NH$_3$, m/z): 359.1 (M$^+$+H).

Example 62(a)

N-1-Hydroxy-2-(4-methylthiophenyl)-4-(3-nitrophenyl)-5-(4-pyridyl)imidazole a) 1-(3-Nitrophenyl)-2-(4-pyridyl)ethanol—The title compound was prepared using the same procedure as described in Example 10, step (b) except using 3-nitrobenzaldehyde: $^1$H NMR (CDCl$_3$): d 8.41 (d, 2H); 8.23 (s, 1H); 8.15 (d, 1H); 7.67 (d, 1H); 7.54 (t, 1H); 7.19 (d, 2H); 5.05 (t, 1H); 4.4 (s, 2H).

(b) 1-(3-Nitrophenyl)-2-(4-pyridyl)acetophenone—To a solution of 1.0 mL (14.3 mmol) of DMSO in 55 mL of dry CH$_2$Cl$_2$ was added 1.82 mL (12.9 mmol) of trifluoroacetic anhydride at −78° C. The mixture was stirred for 30 min, then a solution of 1-(3-nitrophenyl)-2-(4-pyridyl)ethanol (1.09 g, 4.46 mmol) in DMSO/CH$_2$Cl$_2$ (3/11 mL) was added dropwise. The mixture was stirred at −78° C. for 2 h, then 4.1 mL (29.4 mmol) of triethylamine was added dropwise. The ice bath was removed and the mixture was warmed to room temperature. The mixture was poured into saturated NH$_4$Cl and extracted with CH$_2$Cl$_2$. The organic extracts were washed with saturated NH$_4$Cl and saturated NaCl, then dried over MgSO$_4$. Removal of the solvent in vacuo afforded a red oil which was purified by flash chromatography, eluting with a gradient of 0–3% MeOH/CHCl$_3$. The title compound was isolated as an orange oil (0.65 g, 60%): $^1$H NMR (CDCl$_3$): d 8.83 (s, 1H); 8.60 (d, 2H); 8.46 (d, 1H); 8.32 (d, 1H); 7.72 (t, 1H); 7.23 (d, 2H); 4.38 (s, 2H).

(c) 2-Hydroxyimino-1-(3-nitrophenyl)-2-(4-pyridyl) acetophenone The title compound was prepared using the same procedure as described in Example 10, step (c) except using 1-(3-nitrophenyl)-2-(4-pyridyl)acetophenone.

(d) N-1-Hydroxy-2-(4-methylthiophenyl)-4-(3-nitrophenyl)-5-(4-pyridyl)imidazole—The title compound was prepared using the same procedure as described in Example 10, Step (d) except using 2-hydroxyimino-1-(3-nitrophenyl)-2-(4-pyridyl)acetophenone and 4-(methylthio) benzaldehyde: $^1$H NMR (CDCl$_3$/MeOH-d$_4$): d 8.55 (d, 2H); 8.43 (m, 1H); 8.15 (dd, 1H); 8.06 (d, 2H); 7.78 (d, 1H); 7.51 (m, 1H); 7.45 (d, 2H); 7.32 (m, 2H); 2.57 (s, 3H).

Example 62(b)

2-(4-Methylthiophenyl)-4-(3-nitrophenyl)-5-(4-pyridyl)-1H-imidazole

The title compound was prepared using the same procedure as described in Example 1, except using N-1-hydroxy-2-(4-methylthiophenyl)-4-(3-nitrophenyl)-5-(4-pyridyl)-imidazole: CIMS (NH$_3$, m/z): 389.1 (M$^+$+H)

Example 63

4-(3-Methanesulfonamidophenyl)-2-(4-methylthiophenyl)-5-(4-pyridyl)- 1H-imidazole The title compound was prepared using the same procedure as described in Example 29, except using 4-(3-aminophenyl)-2-(4-methylthiophenyl)-5-(4-pyridyl)-1H-imidazole [See Ex. 61 above]: ESMS (m/z): 437.0 (M$^+$+H).

Example 64

3-[4-(4-Fluorophenyl)-5-(4-pyridyl)-1H-imidazol-2-yl] phenyl-1,2,4-oxadiazol-5(4H)-one To a mixture of 4-[4-(4-fluorophenyl)-5-(4-pyridyl)-1H-imidazol-2-yl]benzamide oxime (0.25 g, 0.67 mmol) [See Ex. 44 above] in CH$_2$Cl$_2$ (5.0 mL) and Et$_3$N (0.19 mL, 1.3 mmol) was added ethyl chloroformate (0.076 mL, 0.80 mmol) at rt. After 0.5 h at this temperature, the reaction mixture was poured into H$_2$O, extracted four times with CH$_2$Cl$_2$ and once with 10% MeOH/CH$_2$Cl$_2$. The organic extracts were combined and evaporated. The residue was purified by flash chromatography eluting with a solvent gradient of 2–4% MeOH/CHCl$_3$. Trituration with ether afforded a white solid (0.22 g, 73%). A portion of this compound (0.10 g, 0.22 mmol) was dissolved in HOAc (2.5 mL) and heated to reflux for 18 h. The reaction mixture was poured into H$_2$O, neutralized with concentrated NH$_4$OH, extracted with EtOAc and evaporated. The residue was triturated sparingly with cold EtOAc to afford the title compound as a yellow solid (0.020 g, 23%): CIMS (NH$_3$, m/z): 400 (M$^+$+H).

Example 65

4-(3-Acetamidophenyl)-2-(4-methylthiophenyl)-5-(4-pyridyl)-1H-imidazole

The title compound was prepared using the same procedure as described in Example 6, except using 4-(3-aminophenyl)-2-(4-methylthiophenyl)-5-(4-pyridyl)-1H-imidazole [See Ex. 61 above]: ESMS (m/z): 401 (M$^+$+H).

Example 66

4-(4-Fluorophenyl)-1-N-hydroxy-5-[4-(2-methylpyridyl)]-2-(4-methylthiophenyl)imidazole (a) 2-Methyl isonicotinic acid—The title compound was prepared using the same procedure as described in *Liebigs Ann. Chem.*, 1958, 613, 153: ESMS (m/z): 138.0 (M$^+$+H).

(b) Methyl 2-methylisonicotinate—To an ice-cooled suspension of 1.32 g (9.62 mmol) of 2-methylisonicotinic acid in 20 mL of MeOH was added 1.47 mL (20.2 mmol) of thionyl chloride. The ice-bath was removed and the reaction was stirred at rt. After 22 h, the MeOH was evaporated and the residue was taken up in H$_2$O. The aqueous mixture was neutralized with saturated NaHCO$_3$, then extracted with Et$_2$O. The organic extracts were washed with saturated NaCl, dried over MgSO$_4$, then filtered through a bed of celite. Eva-poration of solvent in vacuo afforded the tire compound as a yellow liquid (0.89 g, 61%): $^1$H NMR (CDCl$_3$): d 8.66 (d, 1H); 7.72 (s, 1H); 7.64 (d, 1H); 3.98 (s, 3H); 2.64 (s, 3H).

(c) Methyl 4-fluorophenylacetate—The title compound was prepared using the same procedure as described in Example 66, step (b) except using 4-fluorophenylacetic acid: $^1$H NMR (CDCl$_3$): d 7.25 (dd, 2H); 7.02 (t, 2H); 3.71 (s, 3H); 3.61 (s, 2H).

(d) 2-(4-Fluorophenyl)-1-[2-methyl-(4-pyridyl)]ethanone—To a freshly prepared solution of NaOMe (3.0M in MeOH) was added a solution of methyl 2-methylisonicotinate (6.81 g, 45.1 mmol) in MeOH (10 mL). This was followed by the dropwise addition of a solution of methyl 4-fluorophenylacetate (8.34 g, 49.6 mmol) in MeOH (10 mL). The MeOH was distilled off while heating the reaction mixture at 95° C. After 17.5 h, the solid residue was cooled. Concentrated HCl (15 mL) was added, and the mixture was heated at reflux. After 4 h, the mixture was cooled then diluted with H$_2$O. The aqueous mixture was washed with Et$_2$O, adjusted to pH 5 with 1N NaOH, then adjusted to pH 8 with saturated NaHCO$_3$. The alkaline aqueous was extracted with EtOAc. The EtOAc extracts were washed with saturated NaCl, then dried over Na$_2$SO$_4$. Evaporation of solvent in vacuo afforded a red oil which was purified by column chromatography, eluting with a gradient of 0–3% MeOH/CHCl$_3$. The title compound was isolated as a red oil (1.5 g, 15%).

(e) 2-(4-Fluorophenyl)-2-hydroxyimino-1-[2-methyl-(4-pyridyl)]ethanone

The title compound was prepared using the same procedure as described in Example 10, step (c) except using 2-(4-fluorophenyl)-1-[2-methyl-(4-pyridyl)]ethanone: ESMS (m/z): 259 (M$^+$+H).

(f) 4-(4-Fluorophenyl)-1-hydroxy-5-[4-(2-methylpyridyl)]-2-(4-methylthio-phenyl)imidazole—The title compound was prepared using the same procedure as described in Example 10, step (d) except using 2-(4-fluorophenyl)-2-hydroxyimino-1-[2-methyl-(4-pyridyl)]ethanone and 4-(methylthio)benzaldehyde: ESMS (m/z): 392 (M$^+$+H).

Example 67

3-[4-(4-Fluorophenyl)-5-(4-pyridyl)-1H-imidazol-2-yl]-phenyl-5,5-dimethyl-4,5-dihydro-1,2,4-oxadiazole To a solution of 4-[4-(4-fluorophenyl)-5-(4-pyridyl)-1H-imidazol-2-yl]benzamide oxime (0.25 g; 0.67 mmol) [See EX. 44 above] in acetone (10 mL) was added pyridinium trifluoroacetate (0.39 g, 2.0 mmol). After heating at reflux for 18 h, the reaction mixture was poured into saturated aqueous NaHCO$_3$, extracted with EtOAc and the organic phase was evaporated. The residue was purified by flash chromatography eluting with a solvent gradient of 2–10% MeOH/CHCl$_3$ to afford the title compound as a white solid (0.1.2 g, 43%): CIMS (NH$_3$, m/z): 414 (M$^+$+H).

Example 68

N-Hydroxy-N-1-[4-[4-(4-fluorophenyl)-5-(4-pyridyl)-1H-imidazol-2-yl]phenyl]ethyl]urea (a) a-Methyl-4-[4-(4-fluorophenyl)-5-(4-pyridyl)-1H-imidazol-2-yl]benzyl alcohol To a mixture of 2-(4-cyanophenyl)-4-(4-fluorophenyl)-5-(4-pyridyl)-1H-imidazole (1.0 g, 2.9 mmol) [See Ex. 1 above] was added MeMgBr (3M in Et$_2$O, 4.0 mL, 12 mmol) at rt. The reaction mixture was heated at reflux for 1 h, poured into saturated aqueous NH$_4$Cl, extracted with THF and the organic phase was evaporated. The residue was dissolved in MeOH (20 mL) and NaBH$_4$ (1.0 g, 26 mmol) was added. After 0.5 h at rt, the solvent was evaporated and the residue was purified by flash chromatography eluting with a solvent gradient of 1–10% MeOH/CHCl$_3$ to afford the title compound as a white solid (0.26 g, 25%): $^1$H NMR (CDCl$_3$/MeOH-d$_4$): d 8.37 (d, 2H); 7.79 (d, 2H); 7.4–7.2 (m, 6H); 6.99 (t, 3H); 4.76 (q, 1H); 1.35 (d, 3H).

(b) N-Hydroxy-N-[1-[4-[4-(4-fluorophenyl)-5-(4-pyridyl)-1H-imidazol-2-yl]phenyl]ethyl]urea—To a mixture of a-Methyl-4-[4-(4-fluorophenyl)-5-(4-pyridyl)-imidazol-2-yl]benzyl alcohol (0.25 g, 0.70 mmol), P(Ph)$_3$ (0.46 g, 1.75 mmol) and N,O-bis(benzyloxycarbonyl) hydroxylamine (0.48 g, 1.75 mmol) in THF (15 mL) was added DEAD (0.28 mL, 1.75 mmol) at rt. The reaction mixture was stirred at this temperature for 3 h and the solvent evaporated. The residue was partially purified by flash chromatography eluting with 1% MeOH/CHCl$_3$. Methanol (25 mL) was added to this material and the mixture was cooled to −78° C. Ammonia was bubbled in at this temperature for 15 min. The reaction mixture was warmed slowly to rt, stoppered and stirred at rt for 2 days. The solvent was evaporated and the residue was purified by flash chromatography eluting with a solvent gradient of 1–10% MeOH/CHCl$_3$. The title compound was obtained as an off-white solid (0.43 g, 14%): FABMS (m/z): 418 (M$^+$+H).

Example 69

N-Hydroxy-N-[4-[4-(4-fluorophenyl)-5-(4-pyridyl)-1H-imidazol-2-yl]phenyl]methyl urea The title compound was obtained using the same procedure described in Example 68, except using 4-(4-fluorophenyl)-2-(4-hydroxymethyl)-5-(4-pyridyl)-1H-imidazole: FABMS (m/z): 418 (M$^+$+H).

Example 70

4-(3-Methylthiophenyl)-2-(4-morpholinomethylphenyl)-5-(4-pyridyl)-1H-imidazole (a) 3-Methylthiobenzaldehyde—The title compound was prepared using the same procedure as described by Campbell, J. R. in *J. Org. Chem.* 1962, 27, 2207: $^1$H NMR (CDCl$_3$): d 9.95 (s, 1H); 7.72 (s, 1H); 7.61 (d, 1H); 7.45 (m, 2H ); 2.53 (s, 3H ).

(b) 1-(3-Methylthiophenyl)-2-(4-pyridyl)ethanol—The title compound was prepared using the same procedure as described in Example 10, step (b) except using 3-(methylthio)benzaldehyde: $^1$H NMR (CDCl$_3$): d 8.33 (d, 2H); 7.0–7.5 (m, 6H), 4.87 (m, 1H); 2.96 (m, 2H); 2.45 (s, 3H).

(c) 1-(3-Methylthiophenyl)-2-(4-pyridyl)ethanedione—To a solution of 1-(3-methylthiophenyl)-2-(4-pyridyl) ethanol (2.5 g, 10.2 mmol) in CH$_2$Cl$_2$ (150 mL) was added a mixture of celite (4.4 g) and pyridinium dichromate (4.4 g, 20.4 mmol). After stirring for 12 h, the mixture was filtered through celite. The solvent was removed in vacuo, and the residue was purified by flash chromatography, eluting with a solvent gradient of 40–50% EtOAc/Hex to provide the title compound (144 mg, 5.5%): $^1$H NMR (CDCl$_3$): d 8.88 (br d, 2H); 7.85 (s, 1H); 7.78 (d, 2H); 7.67(d, 1H); 7.56 (d, 1H); 7.44 (t, 1H); 2.55 (s, 3H).

(d) 4-Morpholinomethylbenzaldehyde diethyl acetal—The title compound was prepared using the same procedure as described by Borch, R. F., Bernstein, M. D., and Durst, H. D. in *J. Am. Chem. Soc.*, 1971, 93, 2897 except using the diethyl acetal: $^1$H NMR (CDCl$_3$): d 7.41 (d, 2H); 7.32 (d, 2H,); 5.48 (s, 1H); 3.3–3.8 (m, 10H); 2.43(br s, 4H); 1.25 (t, 6H).

(e) 4-(3-Methylthiophenyl)2-(4-morpholinomethylphenyl)-5-(4-pyridyl)-1H-imidazole—The title compound was prepared using the same procedure as described in Example 13 except using 1-(3-methylthiophenyl)-2-(4-pyridyl)-ethanedione and 4-morpholinomethylbenzaldehyde diethyl acetal: $^1$H NMR (CDCl$_3$): d 8.47 (d, 2H); 8.02 (d, 2H); 7.3–7.9 (m; 8H); 3.72 (t, 4H); 3.54 (s, 2H); 2.44(br s, 4H); 2.38 (s, 3H).

Example 71

4-(3-Methylsulfinylphenyl)-2-(4-morpholinomethylphenyl)-5-(4-pyridyl)-1H-imidazole The title compound was prepared using the same procedure as described for Example 20, except using 4-(3-methylthiophenyl)2-(4-morpholinomethyl-phenyl)-5-(4-pyridyl)-1H-imidazole [See Ex. 70 above]: $^1$H NMR (CDCl$_3$): d 8.38 (d, 2H); 7.92 (d, 2H); 7.1–7.6 (m, 8H); 3.76 (t; 4H); 3.59, (s, 2H); 2.73 (s, 3H,); 2.52 (br s, 4H).

Example 72

4-(3-Methanesulfonamidophenyl)-2-(4-methylsulfinylphenyl)-5-(4-pyridyl)-1H-imidazole The title compound was prepared using the same procedure as described in Example 20, except using 4-(3-methanesulfonamido-phenyl)-2(4-methylthiophenyl)-5-(4-pyridyl)-1H-imidazole [See Ex. 63 above]: CIMS (NH$_3$, m/z): 453.3 (M$^+$+H).

Example 73

2-(4-Ethylthiophenyl)-4-(4-fluorophenyl)-5-(4-pyridyl)-1H-imidazole

The title compound was prepared using the same procedure as described in Example 13, except using 4-ethylthiobenzaldehyde: mp 203°–205° C.

Example 74

2-(4-Ethylsulfinylphenyl)-4-(4-fluorophenyl)-5-(4-pyridyl)-1H-imidazole

The title compound was prepared using the same procedure as described in Example 20, except using 2-(4-ethylthiophenyl)-4-(4-fluorophenyl)-5-(4-pyridyl)-1H-imidazole [See Ex. 73 above]: mp 240° C.

Example 75

4-(4-Fluorophenyl)-2-[(4-(4-methyl-1-piperzinyl)-sulfonyl-phenyl]-5-(4-pyridyl)-1H-imidazole (a) Ethyl [4-(4-methyl piperazinyl) sulfonamido] benzoate—A mixture of 4-chlorosulfonyl benzoic acid (5.0 g,22.67 mmol), N-methyl piperazine (25 mL) and MeOH (5 mL) was stirred for 18 h and ether (200 mL) was added to the mixture. The crystalline solid precipitate was filtered and washed with ether (200 mL). The solid was suspended in 20% ethanolic HCl and the mixture was heated at reflux until a homogeneous solution was attained (about 2 h). The solution was cooled to rt, concentrated, and the residue was partitioned between sat. NaHCO$_3$ and EtOAc. The organic extract was dried and concentrated to yield the title compound (5.8 g 80%).

(b) 4-(4-Methyl piperazinyl) sulfonamido benzyl alcohol—The title compound was prepared using the same procedure as described in Example 78, step (b) except using ethyl [4-(4-methyl piperazinyl) sulfonamido]benzoate.

(c) 4-(4-Methyl piperazinyl) sulfonamido benzaldehyde—To a solution of oxalyl chloride (1.06 mL, 12.1 mmol) in CH$_2$Cl$_2$ (20 mL) was added DMSO (1.8 mL, 25.4 mmol.) at –60° C. and the mixture was stirred for 25 min. A solution of 4-(4-methyl piperazinyl) sulfonamido benzyl alcohol (3.0 g, 10.5 mmol) in CH$_2$Cl$_2$ (25 mL) and DMSO (5 mL) was added and the mixture was stirred for 1.5 h at –60° C. Triethylamine (7.4 mL) was added and the mixture was partitioned between brine and EtOAc. The organic extract was concentrated, then purified by flash chromatography to yield the title compound (1.0 g, 33%).

(d) 4-(4-Fluorophenyl)-2-[4-(4-methyl piperazinyl) sulfonamido phenyl]-5-(4-pyridyl)-1H-imidazole—The title compound was prepared using the same procedure as described in Example 13, except using 4-(4-methyl piperazinyl) sulfonamido benzaldehyde: mp 74°–76° C.

Example 76

4-(4-Fluorophenyl)-2-[4-(N-methylmethanesulfonamido)-methylphenyl]-5-(4-pyridyl)-1H-imidazole (a) Methyl 4-[(methanesulfonamido)methyl]benzoate—To a suspension of 4-(aminomethyl)benzoic acid (10 g, 66 mmol) in MeOH (100 mL) at 0° C. was added SOCl$_2$ (5.3 mL, 73 mmol) dropwise. The ice bath was removed and the reaction stirred at rt overnight. After heating the reaction at reflux for 4 h, the solvent was evaporated. The residue was suspended in CH$_2$Cl$_2$ (100 mL) at 0° C. and triethylamine (25 mL) was added, followed by the dropwise addition of methanesulfonyl chloride (7.75 mL, 100 mmol). The reaction was stirred at rt for 1 h, poured into ice H$_2$O, extracted with CH$_2$Cl$_2$, dried over anhydrous Na$_2$SO$_4$, filtered and evaporated. The crude product was flash chromatographed on silica gel eluting with 1% MeOH/CHCl$_3$. The title compound was isolated as a white solid (11.8 g, 74%): $^1$H NMR (CDCl$_3$): d 8.03 (d, 2H); 7.42 (d, 2H); 4.9 (br t, 1H); 4.38 (d, 2H); 3.92 (s, 3H); 2.89 (s, 3H).

(b) Methyl 4-[(N-Methylmethanesulfonamido)methyl]benzoate—To a mixture of methyl 4-[(methanesulfonamido)methyl]benzoate (5 g, 20.6 mmol) in MeOH (100 mL) at rt was added K$_2$CO$_3$ (2.9 g, 21 mmol). Methyl iodide (7 ml, 16 g, 112 mmol) was added and the mixture stirred overnight. The reaction was filtered and the solid washed with CHCl$_3$/MeOH. The combined filtrates were evaporated and the residue was purified by flash chromatographyon eluting with 0–5% MeOH/CHCl$_3$. The title compound was isolated as a white solid (4.9 g, 94%): $^1$H (CDCl$_3$): d 8.08 (d, 2H); 7.48 (d,2H); 4.41 (s, 1H); 3.97 (s, 3H); 3.91 (s, 3H); 2.83 (s, 3H).

(c) 4-[(N-Methylmethanesulfonamido)methyl]benzyl alcohol—The title compound was prepared using the same procedure as described in Example 78, step (b) except using methyl 4-[(N-methylmethane-sulfonamido)methyl]benzoate: $^1$H NMR (CDCl$_3$): d 7.34 (m 4H); 4.68 (s,2H); 4.29 (s, 2H); 2.83 (s, 3H); 2.74 (s, 3H).

(d) 4-[(N-Methylmethanesulfonamido)methyl]benzaldehyde—The title compound was prepared using the same procedure as described in Example 78, step (c) except using 4-[(N-methylmethanesulfonamido)-methyl]benzyl alcohol: $^1$H NMR (CDCl$_3$): d 10.02 (s, 1H); 7.9 (d, 2H); 7.54 (d,2H); 4.4 (s, 2H); 2.9 (s, 3H); 2.81 (s, 3H).

(e) 4-(4-Fluorophenyl)-2-[4-(N-methylmethanesulfonamido)-methylphenyl]-5-(4-pyridyl)-1H-imidazole—The title compound was prepared using the same procedure as described in Example 13, except using 4-[(N-methylmethane-sulfonamido)methyl]-benzaldehyde: mp 222°–224° C.

Example 77

Diethyl [1-methyl-4-phenyl-5-(4-pyridyl)-imidazol-2-yl]methoxy]methylphosphonate (a) N-Methyl-N-[4-picolyl]formamide—To a solution of 4-picolyl chloride.HCl (15 g, 91.4 mmol) and N-methylformamide (53.4 mL, 914 mmol) in 300 mL of THF was added 80% NaH in mineral oil (5.48 g, 183 mmol). After stirring at rt for 18 h the mixture was quenched with ice water and partitioned between CH$_2$Cl$_2$ and H$_2$O. The organic extract was washed with aqueous NaCl and dried over MgSO$_4$. The solvent was removed in vacuo, and the residue was purified by flash chromatography, eluting with 50:1 CH$_2$Cl$_2$/MeOH. The title compound was obtained as a pale yellow oil (10.5 g, 76%): ESMS (m/z): 151 (M$^+$+H).

(b) 1-Methyl-4-phenyl-5-[4-pyridyl]imidazole—To a solution of di-iso-propyl-amine (11.2 mL, 79.9 mmol) in 150 mL of THF at –78° C. was added n-butyllithium (31.9 mL of 2.5M solution, 79.9 mmol). To the resulting mixture was added a solution of N-methyl-N-[4-picolyl]formamide (10 g, 66.5 mmol) in THF. The resulting orange-brown solution was stirred at –78° C. for 20 min, at which time benzonitrile (13.6 mL, 133 mmol) was added. The resulting dark brown mixture was allowed to warm to rt and stirred for 1 h, heated to reflux for 4 h, and then cooled to rt and partitioned between CH$_2$Cl$_2$ and H$_2$O. The organic extract was washed with aqueous NaCl and dried (MgSO$_4$). The solvent was removed in vacuo, and the residue was purified by flash chromatography, eluting with 50:1 CH$_2$Cl$_2$/MeOH. The title compound was obtained as a light tan solid (5.83 g, 37%): mp 158°–159° C.

(c) 2-Formyl-1-methyl-4-phenyl-5-[4-pyridyl]imidazole—To a solution of 1-methyl-4-phenyl-5-[4-pyridinyl]imidazole (0.275 g, 1.17 mmol) in THF at –78° C. was added n-butyllithium (0.56 mL of 2.5M solution, 1.40 mmol). The resulting red-orange solution was allowed to stir at –78° C. for 0.5 h when DMF (0.18 mL, 2.34 mmol) was added. The mixture was allowed to warm to rt and stir for 4 h, then quenched with ice water and partitioned between CH$_2$Cl$_2$ and H$_2$O. The organic extract was washed with aqueous NaCl and dried (MgSO$_4$). The solvent was removed in vacuo and the residue was purified by flash chromatography eluting with 50:1 CH$_2$Cl$_2$/MeOH. The title compound was obtained as a white solid (0.187 g, 61%): mp 167°–168° C.

(d) 2-Hydroxymethyl-1-methyl-4-phenyl-5-(4-pyridyl)imidazole—To a solution of 2-formyl-1-methyl-4-phenyl-5-[4-pyridyl]imidazole (0.830 g, 3.15 mmol) in MeOH at 0° C. was added NaBH$_4$ (0.143 g, 3.78 mmol). The mixture was stirred at rt for 0.5 h when the solvent was evaporated in vacuo and the residue was partitioned between CH$_2$Cl$_2$ and H$_2$O. The organic extract was washed with. aqueous NaCl and dried (MgSO$_4$). The solvent was removed in vacuo and the residue was purified by flash chromatography eluting with 25:1. CH$_2$Cl$_2$/MeOH. The title compound was obtained as a white solid (0.608 g, 73%): mp 236°–238° C.

(e) Diethyl [1-methyl-4-phenyl-5-(4-pyridyl)-imidazol-2-yl]methoxy]-methyl-phosphonate—To a suspension of 80% NaH in mineral oil (0.013 g, 0.452 mmol) in DMF at 0° C. was added 1-methyl-2-hydroxymethyl-4-phenyl-5-[4-pyridinyl]imidazole (0.100 g, 0.377 mmol) in DMF. The resulting bright yellow solution was stirred at 0° C. for 0.5 h when diethyl chloromethylphosphonate (0.070 mL, 0.452 mmol) dissolved in 0.079 mL of HMPA was added. The resulting mixture was stirred at 0° C. for 15 min and then warmed to rt. After 5 h, the solution was partitioned between CH$_2$Cl$_2$ and H$_2$O. The organic extract was washed with aqueous NaCl and dried (MgSO$_4$). The solvent was removed in vacuo, and the residue was purified by flash chromatography, eluting with 50:1 CH$_2$Cl$_2$/MeOH. The title compound was obtained as a light amber oil (0.088 g, 56%): ESMS (m/z): 416 (M$^+$+H).

Example 78

4-(4-Fluorophenyl)-2-[4-(methanesulfonamido)-methylphenyl]-5-(4-pyridyl)-1H-imidazole (a) Methyl 4-[(methanesulfonamido)methyl]-benzoate—The title compound was prepared using the same procedure as described in Example 76, step (a).

(b) 4-[(Methanesulfonamido)methyl]benzyl alcohol—To a mixture of methyl 4-[(methanesulfonamido)methyl]benzoate (3.6 g, 15 mmol) in THF (150 mL) was added LiAlH$_4$ (1M in THF, 30 mL, 30 mmol). The reaction mixture was stirred at rt for 1 h and poured into 10% MeOH/CHCl$_3$ containing silica gel. The solids were removed by filtration, washed with 10% MeOH/CHCl$_3$ and the combined washings were evaporated to yield the title compound as a white solid (2.6 g, 80%).

(c) 4-[(Methanesulfonamido)methyl]benzaldehyde—To a solution of 4-[(methanesulfonamido)methyl]benzyl alcohol (1.0 g, 4.6 mmol) in CH$_2$Cl$_2$ (25 mL) was added pyridinium chlorochromate (1.5 g, 7.0 mmol). The reaction mixture was stirred for 1 h at rt and poured through a pad of silica gel eluting with 2% MeOH/CHCl₃. The title compound was isolated as a tan solid (1.0 g, 100%): ¹H NMR (CDCl3): d 10.03 (s,1H); 7.88 (d, 2H); 7.57 (d, 2H); 4.79 (br s, 1H); 4.43 (d, 2H); 2.93 (s, 3H).

(d) 4-(4-Fluorophenyl)-2-[4-(methanesulfonamido) methylphenyl]-5-(4-pyridyl)-1H-imidazole—The title compound [also prepared in Example 32] was prepared using the same procedure as described in Example 13, except using 4-[(methanesulfonamido)methyl]benzaldehyde.

Example 79

4-(4-Fluorophenyl)-2-(4-methylthiophenyl)-5-(4-pyridyl)-1H-imidazole (a) 1-(t-Butyldimethylsilyloxy)-2-(4-fluorophenyl)-1-(4-pyridyl)ethanone—To a −20° C. solution of diisopropylamine (64.4 mL, 0.46 mol) and THF (120 mL) was added 207.8 mL (0.52 mol, 2.5M solution in hexanes) of n-butyllithium dropwise over 15 min. The temperature was lowered to −15° C. and the mixture was stirred for 0.5 hr. The solution was cooled to −20° C. and 98.14 g (0.44 mol) of 4-(t-butyldimethylsilyloxy)methyl pyridine was added dropwise over 20 min. After stirring at −20° C. for 45 min, a solution of 4-fluoro-N-methoxy-N-methylbenzamide (84.5 g, 0.46 mol) [See Ex. 10, step (a)] in THF (90 mL) was added dropwise over 0.5 hr. Once the addition was complete, the ice bath was removed and the reaction mixture was warmed to 0° C. for 1 hr, then stirred at rt for 1.5 hr. The mixture was poured into a solution of NH₄Cl (98 g) and H₂O (500 mL), then extracted with EtOAc (3×250 mL). The EtOAc extracts were washed with H₂O and saturated NaCl, then dried over MgSO₄. Evaporation of the solvent in vacuo afforded the title compound as an amber oil (114.2 g, 75%).

(b) 4-(4-Fluorophenyl)-2-(4-methylthiophenyl)-5-(4-pyridyl)-1H-imidazole—To a solution of 1-(t-butyldimethylsilyloxy)-2-(4-fluorophenyl)-1-(4-pyridyl) ethanone (6.3 g, 18.3 mmol) in glacial acetic acid (125 mL) was added anhydrous copper (II) acetate (6.6 g, 36.5mmol), ammonium acetate (14 g, 183 mmol) and 4-(methylthio) benzaldehyde (3.5 g, 22.9 mmol) and the mixture was heated at reflux. After 1 hr, the reaction was cooled then poured into a mixture of conc. NH₄OH (175 mL), ice (100 mL) and EtOAc (100 mL). The resulting mixture was stirred for 15 min, then the layers were separated. The aqueous layer was extracted with EtOAc (2×50 mL). The combined EtOAc extracts were washed with saturated NaCl and dried over MgSO₄. Evaporation of solvent in vacuo gave an oil which was taken up in acetone. 3N HCl was added dropwise to adjust the pH to 2–3, and the resulting solid was filtered. The title compound [also prepared in Ex. 17 as the free base] was isolated as the yellow hydrochloride salt (3.7 g, 51%).

Example 80

2-[4-[(N-Benzyl-N-methyl)aminomethyl]phenyl]4-(4-fluorophenyl)-5-(4-pyridyl)-1H-imidazole (a) 4-[(N-benzyl-N-methyl)aminomethyl]benzaldehyde diethylacetal—To 62.4 g (0.30 mol) of terephthalaldehyde monodiethyl acetal was added 32.1 g (0.30 mol) of benzyl amine and 500 mL toluene. The resulting solution was heated at reflux using a Dean-Stark trap. After 1 hour the solution was cooled and concentrated to give a light yellow oil (89.1 g). The oil was dissolved in 900 mL of EtOAc and 2.0 g of 5% palladium on charcoal was added. The mixture was hydrogenated on a Parr hydrogenation apparatus under 37 psi hydrogen pressure. The mixture was shaken for 1 hour at rt. The bottle was vented and 34.4 mL (0.42 mol) of 37.5% formaldehyde solution (aqueous) was added. The bottle was repressurized with 33 psi hydrogen and the mixture was shaken for 17 hours at rt. The bottle was vented and the reaction mixture was filtered and the filtrate concentrated to a nearly colorless oil (93.9 g). Vacuum distillation gave 71.4 g (76%) of 4-(N-methyl-N-benzyl) aminomethylbenzaldehyde diethylacetal: bp (30 torr) 212°–234° C.

(b) 2-[4-[(N-Benzyl-N-methyl)aminomethyl]phenyl]4-(4-fluorophenyl)-5-(4-pyridyl)-1H-imidazole—The title compound [also prepared in Ex. 36] was prepared as described in Example 13, except using 4-[(N-benzyl-N-methyl)aminomethyl]benzaldehyde diethylacetal.

Example 81

4-(4-Fluorophenyl)-2-(3-methylthiophenyl)-5-(4-pyridyl)-1H-imidazole

The title compound was prepared using the same procedure as described in Example 79(b), except using 3-(methylthio)-benzaldehyde.

Example 82

4-(4-Fluorophenyl)-2-(3-methylsulfinylphenyl)-5-(4-pyridyl)-1H-imidazole

The title compound was prepared using the same procedure as described in Example 20, except using 4-(4-Fluorophenyl)-2-(3-methylthiophenyl)-5-(4-pyridyl)-1H-imidazole.

Example 83

4-(4-Fluorophenyl)-2-(3-methylsulfonylphenyl)-5-(4-pyridyl)-1H-imidazole

The title compound was prepared using the same procedure as described in Example 79, except using 4-(4-Fluorophenyl)-2-(3-methylsulfinylphenyl)-5-(4-pyridyl)-1H-imidazole.

Example-84

4-(4-Fluorophenyl)-2-(2-methylthiophenyl)-5-(4-pyridyl)-1H-imidazole

The title compound was prepared using the same procedure as described in Example 79(b), except using 2-(methylthio)-benzaldehyde.

Example 85

4-(4-Fluorophenyl)-2-(2-methylsulfinylphenyl)-5-(4-pyridyl)-1H-imidazole

The title compound was prepared using the same procedure as described in Example 20, except using 4-(4-Fluorophenyl)-2-(2-methylthiophenyl)-5-(4-pyridyl)-1H-imidazole.

Example 86

4-(4-Fluorophenyl)-2-(2-methylsulfonylphenyl)-5-(4-pyridyl)-1H-imidazole

The title compound was prepared using the same procedure as described in Example 79, except using 4-(4-Fluorophenyl)-2-(2-methylsulfinylphenyl)-5-(4-pyridyl)-1H-imidazole.

Example 87

4-(4-Fluorophenyl)-2-(thiophen-2-yl)-5-(4-pyridyl)-1H-imidazole

The title compound was prepared using the same procedure as described in Example 79(b), except using 2-thiophene carboxaldehyde.

Example 88

4-(4-Fluorophenyl)-2-(thiophen-3-yl)-5-(4-pyridyl)-1H-imidazole

The title compound was prepared using the same procedure as described in Example 79(b), except using 3-thiophene carboxaldehyde.

Example 89

4-(naphth-1-yl)-2-(4-methylthiophenyl)-5-(4-pyridyl)-1H-imidazole

The title compound was prepared using the same procedure as described in Example 79(a), except using 1-naphth-(N-methoxy-N-methyl)amide.

Example 90

4-(naphth-2-yl)-2-(4-methylthiophenyl)-5-(4-pyridyl)-1H-imidazole

The title compound was prepared using the same procedure as described in Example 79(a), except using 2-naphth-(N-methoxy-N-methyl)amide.

Example 91

4-(naphth-1-yl)-2-(4-methylsulfinylphenyl)-5-(4-pyridyl)-1H-imidazole

The title compound was prepared using the same procedure as described in Example 20, except using 4-(naphth-1-yl)-2-(4-methylthiophenyl)-5-(4-pyridyl)-1H-imidazole.

Example 92

4-(naphth-2-yl)-2-(4-methylsulfinylphenyl)-5-(4-pyridyl)-1H-imidazole

The title compound was prepared using the same procedure as described in Example 20, except using 4-(naphth-2-yl)-2-(4-methylthiophenyl)-5-(4-pyridyl)-1H-imidazole.

Example 93

2-(4-Cyanophenyl)-4-(4-fluorophenyl)-5-(4-pyridyl)-1H-imidazole

The title compound was prepared using the same procedure as described in Example 79(b), except using 4-cyanobenzaldehyde, mp 268–269.

Example 94

2-(4-Aminomethylphenyl)-4-phenyl-5-(4-pyridyl)-imidazole

To a solution of 2-(4-cyanophenyl)-4-(4-fluorophenyl)-5-(4-pyridyl)-1H-imidazole (2.5 g, 7.3 mmol) [See Ex. 96 above] in THF (50 mL) was added LiAlH$_4$ (7.3 mL of 1M solution in THF, 7.3 mmol), and the resulting mixture was heated at reflux for 2 h, at which time tlc analysis indicated that the reaction was incomplete. Additional LiAlH$_4$ (4.0 mL, 4.0 mmol) was added and heating was continued for 30 min. The mixture was allowed to cool, then poured into 2.5N NaOH and extracted with THF. The organic extract was washed with saturated aqueous NaCl and concentrated under reduced pressure. The residue was purified by flash chromatography, eluting with 9:1 CHCl$_3$/MeOH, followed by 90:10:1 CHCl$_3$/MeOH/NH$_3$. The material that was isolated was triturated with Et$_2$O to afford the title compound (1.5 g, 60%): mp 214°–215° C.

Example 95

2-(4-Biotinamidomethylphenyl)-1-methyl-4-phenyl-5-(4-pyridyl)-imidazole

To a solution containing 2-(4-Aminomethylphenyl)-4-phenyl-5-(4-pyridyl)-imidazole (1 equivalent) in DMF was added N-hydroxysuccinimide biotin (1.2 eq). Following normal workup and chromatography the title compound was obtained: CIMS (NH$_3$, m/z): 523 (M$^+$+H).

Example 96

4-(4-Fluorophenyl)-1-methyl-2-(4-methylsulfinyl)phenyl-5-(4-pyridyl)imidazole (a) N-Methyl-4-(methylthio)phenyl benzamidine—The title compound was prepared following the procedure fo Garigipati (Tetrahedron Lett. 1990, 31(14), 1969) except using methylamine hydrochloride and 4-(methylthio)-benzonitrile.

(b) 4-(4-Fluoro)phenyl-1-methyl-2-(4-methylthio)phenylimidazole—The title compound was prepared following the procedure of Fitzi (U.S. Pat. No. 3,940,486) except using N-methyl-4-(methio)phenylbenzamidine and 2-chloro-4'-fluoroacetophenone.

(c) 4-(4-Fluoro)phenyl-1-methyl-2-(4-methylthio)phenyl-5-(4-pyridyl)imidazole—The title compound was prepared by the procedure of Lantos et al. (J. Org. Chem. 1988, 53, 4223) except using 4(4-fluoro)phenyl-1-methyl-2-(4-methylthio)phenylimidazole.

(d) 4-(4-Fluoro)phenyl-1-methyl-2-(4-methylsulfinyl)phenyl-5-(4-pyridyl)imidazole—The title compound was prepared by the same procedure as described in Example 20 except using 4-(4-fluoro)phenyl-1-methyl-2-(4-methylthio)phenyl-5-(4-pyridyl)imidazole: CIMS (NH$_3$, m/z): 392 (M$^+$+H).

Example 97

4-(4-Fluoro)phenyl-1-methyl-2-(4-methylthio)phenyl-5-[4-(2-amino)-pyrimidinyl]imidazole (a) 4-(4-Fluoro)phenyl-1-methyl-2-(4-methylthio)phenyl-5-tri-n-butylstannylimidazole—The title compound was prepared by the procedure of Bender et al. (U.S. Pat. No. 5,145,858 and U.S. Pat. No. 5,002,941) except using 4-(4-fluoro)phenyl-1-methyl-2-(4-methylthio)phenylimidazole.

(b) 4-(4-Fluoro)phenyl-1-methyl-2-(4-methylthio)phenyl-5-[4-(2-methylthio)pyrimidinyl]imidazole—A mixture of 4-(4-Fluoro)phenyl-1-methyl-2-(4-methylthio)phenyl-5-tri-n-butylstannylimidazole (0.25 g, 0.42 mmol), 4-iodo-2-methythiophenylpyrimidine (0.16 g, 0.63 mmol) [prepared by the procedure of Majeed et al. (Tetraherdon 1989, 45(4), 993)] and bis(triphenylphosphine)palladium(II) dichloride (0.30 g, 0.42 mmol) in 1,2 dichloroethane (10 mL) was heated to reflux for 24 h. The reaction mixture was cooled to ambient temperature and a solution of saturated potassium fluoride in methanol (2 mL) was added. After stirring for 1 h at ambient temperature, the mixture was poured into water and extracted twice with dichloromethane. The organic layers were combined, washed with saturated aqueous sodium chloride, dried (MgSO$_4$) and the solvent evaporated. The residue was purified by flash chromatography eluting with dichloromethane to afford the title compound as a yellow foam (0.14 g, 78%).

(c) 4-(4-Fluoro)phenyl-1-methyl-2-(4-methylsulfonyl)phenyl-5-[4-(2-methylsulfonyl)pyrimidinyl]imidazole—To a solution of 4-(4-Fluoro)phenyl-1-methyl-2-(4-methylthio)phenyl-5-[4-(2-methylthio)pyrimidinyl]imidazole (0.10 g, 0.24 mmol) in dichloromethane (10 mL) was added 80% m-chloroperbenzoic acid (0.25 g, 1.2 mmol). After stirring at ambient temperature for 18 h, the reaction mixture was poured into saturated aqueous sodium carbonate and the layers were separated. The organic phase was washed with saturated aqueous sodium chloride, dried (MgSO$_4$) and evaporated. The residue was purified by flash chromatography eluting successively with dichloromethane and 1% methanol in dichloromethane to afford the title compound as a yellow foam (0.11 g, 94%).

(d) 4-(4-Fluoro)phenyl-1-methyl-2-(4-methio)phenyl-5-[4-(2-amino)pyrimidinyl]imidazole—4-(4-Fluoro)phenyl-1-methyl-2-(4-methylsulfonyl)phenyl-5-[4-(2-methylsulfonyl)pyrimidinyl]imidazole (0.50 g, 0.10 mmol) was added to concentrated ammonium hydroxide (2 mL) and reaction mixture was heated to 150° C. in a sealed vessel. After cooling to ambient temperature, the reaction mixture was diluted with water and extracted twice with dichloromethane and once with 4% methanol in dichloromethane. The organic layers were combined and the solvent evaporated. The residue was purified by flash chromatography eluting successively with 2%, 4% and 10% methanol in dichloromethane followed by trituration with ether to afford the title compound as a white solid (0.017 g, 39%): CIMS (NH$_3$, m/z): 424 (M$^+$+H).

The following compounds may be made by analagous methods to those described above:

Example 98

4-(4-Fluorophenyl)-2-(4-methylsulfinylphenyl)-1-(N-morpholinopropyl)-5-(4-pyridyl)imidazole;

Example 99

4-(4-Fluorophenyl)-2-(4-methylthiophenyl)-1-(N-morphlinopropyl)-5-(4-pyridyl)imidazole;

Example 100

4-(4-Fluorophenyl)-2-(4-methylsulfinylphenyl)-1-(N-morpholinopropyl)-5-(4-pyridyl)imidazole;

Example 101

4-(4-Fluorophenyl)-1-(methylthio-1-propyl)-2-([4-N-morpholinomethyl]phenyl)-5-(4-pyridyl)imidazole;

Example 102

4-(4-Fluorophenyl)-1-(methylsulfinyl-1-propyl)-2-([4-N-morpholinomethyl]phenyl)-5-(4-pyridyl)imidazole;

Example 103

4-(4-Fluorophenyl)-1-(methylsulfonyl-1-propyl)-2-([4-N-morpholinomethyl]phenyl)-5-(4-pyridyl)imidazole.

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

Compounds of formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interferring amount of a compound of formula (I) or a pharmaceutically acceptable salt thereof.

In particular, compounds of formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of formula (I) or a pharmaceutically acceptable salt thereof.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of formula (I) or a pharmaceutically acceptable salt thereof Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal, preferably a human, afflicted with a human immunodeficiency virus (HIV) which comprises administering to such mammal an effective TNF inhibiting amount of a compound of formula (I) or a pharmaceutically acceptable salt thereof.

Compounds of formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, the lentivirus infections such as equine infectious anaemia virus, caprine arthritis virus, visna virus, or the maedi virus, or the retroviruses, such as feline immunodeficiency virus (FIV), bovine immunodeficiency virus, or canine immunodeficiency virus.

The compounds of formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis; pain and other conditions associated with inflammation.

Compounds of formula (I) have also been shown to inhibit the production of IL-8 (Interleukin-8, NAP). Accordingly, in a further aspect, this invention relates to a method of inhibiting the production of IL-8 in a mammal in need thereof which comprise administering to said mammal an effective amount of a compound of formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of formula (I) are administered in an amount sufficient to inhibit cytokine, in particular IL-1, IL-8 or TNF, production such that it is regulated down to normal levels, or in some case to subnormal levels, so as to ameliorate or prevent the disease state. Abnormal levels of IL-1, IL-8 or TNF, for instance in the context of the present invention, constitute: (i) levels of free (not cell bound) IL-1, IL-8 or TNF greater than or equal to 1 picogram per ml; (ii) any cell associated IL-1, IL-8 or TNF; or (iii) the presence of IL-1, IL-8 or TNF mRNA above basal levels in cells or tissues in which IL-1, IL-8 or TNF, respectively, is produced.

The discovery that the compounds of formula (I) are inhibitors of cytokines, specifically IL-1, IL-8 and TNF is based upon the effects of the compounds of formulas (I) on the production of the IL-1, IL-8 and TNF in in vitro assays which are described herein.

As used herein, the term "inhibiting the production of IL-1 (IL-8 or TNF)" refers to:

a) a decrease of excessive in vivo levels of the cytokine (IL-1, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-8 or TNF) in a human to normal or sub-normal levels;

c) a down regulation, by inhibition of the direct synthesis of the cytokine (IL-1, IL8 or TNF) as a postranslational event; or d) a down regulation, at the translational level, of excessive in vivo levels of the cytokine (IL1, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphoctye cells. Examples of cytokines include, but are not limited to, Interleukin-1(IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppresive amount" refers to an effective amount of a compound of formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in freely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of formula (I) or a pharmaceutically acceptable salt thereof given per day for a defined number of days, can be ascertained by those skilled in the art using conventional course of treatment determination tests.

BIOLOGICAL EXAMPLES

Several compounds of Formula (I) were shown in a 10 to 14 day dose ranging toxicity study, in rats, and confirmed in part in mice, to have exhibited spontaneous lesions and demonstrated dose related cardiotoxicity at extremely high levels. This result has not been confirmed in compounds which do not have $R_1$ as an unsubstituted 4-pyridyl, $R_2$ as hydrogen and $R_3$ as a substituted phenyl. It is however, preferred, that the compounds of formula (I) do not posses $R_2$ as hydrogen, when $R_1$ is an unsubstituted 4-pyridyl, and $R_3$ is a substituted phenyl. The compounds exhibiting the above toxicity are:

4-(4-Fluorophenyl)-2-(4-methylsulfinylphenyl)-5-(4-pyridyl)-1H-imidazole 2-(4-Ethylsulfinylphenyl)-4-(4-fluorophenyl)-5-(4-pyridyl)-1H-imidazole 4-(4-Fluorophenyl)-2-(4-Morpholinomethylphenyl)-5-(4-pyridyl)-1H-imidazole 2-[4-(N-Benzyl-N-methyl)aminomethylphenyl]-4-(4-fluorophenyl)-5-(4-pyridyl)-1H-imidazole The cytokine-inhibiting effects of compounds of the present invention were determined by the following in vitro assays:

Interleukin-1 (IL-1)

Human peripheral blood monocytes were isolated and purified from either fresh blood preparations from volunteer donors, or from blood bank buffy coats, according to the procedure of Colotta et al, J Immunol, 132, 936 (1984). These monocytes (1×10⁶) were plated in 24-well plates at a concentration of 1-2 million/ml per well. The cells were allowed to adhere for 2 hours, after which time non-adherent cells were removed by gentle washing. Test compounds were then added to the cells for 1 h before the addition of lipopolysaccharide (50 ng/ml), and the cultures were incubated at 37° C. for an additional 24 h. At the end of this period, culture supernatants were removed and clarified of cells and all debris. Culture supernatants were then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. ImmunoTherapy, 6 (1), 1-12 (1990) (ELISA assay). Compounds of formula (I) were shown to be inhibitors of in vitro IL-1 produced by human monocytes.

Tumor Necrosis Factor (TNF)

Human peripheral blood monocytes were isolated and purified from either blood bank buffy coats or plateletpheresis residues, according to the procedure of Colotta, R. et al., J Immunol, 132(2), 936 (1984). The monocytes were plated at a density of 1×10⁶ cells/ml medium/well in 24-well multi-dishes. The cells were allowed to adhere for 1 hour after which time the supernatant was aspirated and fresh medium (1 ml, RPMI-1640, Whitaker Biomedical Products, Whitaker, Calif.) containing 1% fetal calf serum plus penicillin and streptomycin (10 units/ml) added. The cells were incubated for 45 minutes in the presence or absence of a test compound at 1 nM-10 mM dose ranges (compounds were solubilized in dimethyl sulfoxide/ethanol, such that the final solvent concen-tration in the culture medium was 0.5% dimethyl sulfoxide/0.5% ethanol). Bacterial lipopolysaccharide (*E. coli* 055:B5 [LPS] from Sigma Chemicals Co.) was then added (100 ng/ml in 10 ml phosphate buffered saline) and cultures incubated for 16–18 hours at 37° C. in a 5% $CO_2$ incubator. At the end of the incubation period, culture supernatants were removed from the cells, centrifuged at 3000 rpm to remove cell debris. The supernatant was then assayed for TNF activity using either a radioimmuno or an ELISA assay, as described in WO 92/10190 and by Becker et al., J Immunol, 1991, 147, 4307. Compounds of formula (I) were shown to be inhibitors of in vitro TNF production.

IL-1 and TNF inhibitory activity does not seem to correlate with the property of the compounds of Formula (I) in mediating arachidonic acid metabolism inhibition, further the ability to inhibit production of prostaglandin and/or leukotriene synthesis, by nonsteroidal anti-inflammatory drugs with potent cyclooxygenase and/or lipoxygenase inhibitory activity does not mean that the compound will necessarily also inhibit TNF or IL-1 production, at non-toxic doses.

Interleukin-8 (IL-8)

Primary human umbilical cord endothelial cells (HUVEC) (Cell Systems, Kirland, Wash.) were maintained in culture medium supplemented with 15% fetal bovine serum and 1% CS-HBGF consisting of aFGF and heparin. The cells were then diluted 20-fold before being plated (250 µl) into gelating coated 96-well plates. Prior to use, culture medium was replaced with fresh medium (200 µl). Buffer or test compound (25 µl, at concentrations between 1 and 10 µM) was then added to each well in quadruplicate wells and the plates incubated for 6 h in a humidified incubator at 37° C. in an atmosphere of 5% $CO_2$. At the end of the incubation period, supernatant was removed and assayed for IL-8 concentration using an IL-8 ELISA kit obtained from R&D Systems (Minneapolis, Minn.). All data were presented as mean value (ng/ml) of multiple samples based on the standard curve. $IC_{50}$'s where appropriate were generated by non-linear regression analysis. The compounds of formula (I), examples 5, 8b and 9, demonstrated a dose dependent reduction in the production of IL-8(a 50–65% inhibition of IL-8).

Cytokine Specific Binding Protein Assay (CSBP)

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible binding assay was developed using soluble cystosolic fraction from THP.1 cells and a radiolabeled compound. For instance, a suitable radiolabeled compound of the CSAID™ class is 4-(Fluorophenyl)-2-(4-hydroxyphenyl-3,5-$t_2$)-5-(4-pyridyl)imidazole. In brief, the THP.1 cytosol was routinely prepared from cell lysate obtained by nitrogen cavitation followed by a 10K×g low speed and a 100K×g high speed centrifugation, the supernatant of which was designated as the cytosolic fraction. THP.1 cytosol was incubated with appropriately diluted radioligand at room temperature for a pre-determined time to allow the binding to achieve equilibrium. The sample was added to a G-10 column and eluted with 20 mm TRN, 50 mMb-mercaptoethanol, $NaN_3$. The fraction encompassing the void volume was collected and the radioactivity was assessed by liquid scintillation counting. This was determined to reflect bound radioligand since the radioactive signal was abrogated by the presence of excess cold ligand in the incubation mixture or when there was no cytosolic fraction present. Compounds of Formula (I) at various doses were added to the binding assay to achieve inhibition of binding of the radiolabel. $IC_{50}$s as well as Ki values were determined by regression analysis and scatchard plot analysis respectively. There is generally excellent correlation between the $IC_{50}$ of compounds tested in both the binding assay and the bioassay and can be used interchangeably in many cases.

Patent application U.S. Ser. No. 08/123,175 Lee et al., filed September 1993 whose disclosure is incorporated by reference herein in its entirely describes the above noted method for screening drugs to identify compounds which interact with and bind to the CSBP. However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the creening protocol. Regardless of the form of the binding protein, a plurality of compounds are contacted with the binding protein under conditions sufficient to form a compound/binding protein complex and compound capable of forming, enhancing or interfering with said complexes are detected.

More specifically, the Binding Assay is performed as follows:

MATERIALS:

Incubation buffer: 20 mM Tris, 1 mM $MgCl_2$, 20 mM Hepes, 0.02% $NaN_3$, store at 4° C. Elution buffer: 20 mM Tris, 50 mM 2-mercaptoethanol, $NaN_3$, store at 4° C.

G-10 Sephadex: add 100 g Sephadex G-10 (Pharmacia, Uppsala, Sweden) to 400 mL dd $H_2O$ and allow to swell at room temperature for 2 hours. Decant fines and wash 3 times. Add $NaN_3$ and qs with dd $H_2O$ to 500 mLs and store at 4° C.

Assemble Columns: Straw column, filter frit and tip (Kontes, SP 420160-000, 420162-002). Lowsorb tubes (Nunc) used in binding reaction. THP.1 cytosol spun at 15000 rpm for 5 min to clarify. THP.1 cytosol prepared by hypnotic treatment of cells and lysis by decompression in nitrogen. Nuclei and membrane fragments removed by differential centrifugation (10,000 g for 1 hour and 100,000 g for 1 hour).

Compounds: Non-radioactive Compound I with corresponding EtOH control (dilutions made in incubation buffer) and $^3$H-Compound I (dilutions in incubation buffer)

METHOD:

A. Column Preparation
1. Begin 30 min before anticipated elution of reaction mixture.
2. Add 3 mL of G-10 slurry to column for bed vol of 1.5 ml.
3. Rinse with 7 mL elution buffer (fill to top of column)
4. Cut columns down to size.

B. Sample Incubation
1. 15 min incubation at 4° C.
2. Binding reaction mixture; 100 μL cytosol, 10 μL cold Compound I or EtOH control, 10 μL $^3$H-Compound I (molar concentration depends on nature of study).
3. "Free" control=100 μL incubation buffer in lieu of cytosol preparation.

C. Sample Elution
1. Elute at 4° C.
2. Add total reaction volume to G-10 column.
3. Add 400 μL elution buffer to column and discard eluate.
4. Add 500 μL elution buffer to column, collecting eluted volume in 20 ml scintillation vial.
5. Add 15 mL Ready Safe scintillation fluid.
6. Vortex and count in liquid scintillation counter for 5 minutes.

Include a "total input counts control" (10 μL of labeled ligand).

D. Data Analysis
1. Plot DPMS as output in graphic form and analyze by regression analysis and "Lundon ligand binding" software for the determination of IC50 and Kd/Ki respectively.
2. Rank order the IC50s of the tested compounds in the bioassay and compare to that generated by the binding assay and establish a correlation curve.

The binding assay was further validated by the following criteria:

THP.1 cytosol demonstrated saturable and specific binding of the radiolabeled compound.

Preparation of 4-(Fluorophenyl)-2-(4-hydroxyphenyl-3,5-$t_2$)-5-(4-pyridyl)imidazole, (Compound I).

A 2.9 mg (0.0059 mmol) portion of 2-(3,5-Dibromo-4-hydroxyphenyl)-4-(4-fluorophenyl)-5-(4-pyridyl)imidazole, Compound I(p), was dissolved in 0.95 mL of dry DMF and 0.05 mL of triethylamine in a 2.4 mL round bottom flask equipped with a small magnetic stirring bar. A 1.7 mg portion of 5% Pd/C (Engelhard lot 28845) was added, and the flask was attached to the stainless steel tritium manifold. The mixture was degassed through four freeze-pump-thaw cycles, then tritium gas (5.3 Ci, 0.091 mmol) was introduced. The reaction mixture was allowed to warm to room temperature and was stirred vigorously for 20 h. The mixture was frozen in liquid nitrogen, the remaining tritium gas (2.4 Ci) was removed, and the flask was removed from the manifold. The reaction mixture was transferred, using 3×1 mL of methanol as rinsings, into a 10 mL round bottom flask, and the solvents were removed by static vacuum transfer. A 1.5 mL portion of methanol was added to the residue, then removed by static vacuum transfer. The latter process was repeated. Finally, the residue was suspended in 1.5 mL of ethanol and filtered through a syringe-tip Millipore filter (0.45 micron), along with 3×ca. 1 mL ethanol rinsings. The total filtrate volume was determined to be 3.9 mL, and the total radioactivity, 94.2 mCi. Solution was determined to be 3.9 mL, and the total radioactivity, 94.2 mCi. HPLC analysis of filtrate (Partisil 5ODS-3, 4.6 mm I.D.×25 cm, 1 mL/min of 70:30:01 water/acetonitrile/trifluoroacetic acid, Radiomatic Flo-One Beta radio detector with 3 mL/min of Ecoscint-H cocktail through a 0.75 mL cell) showed the presence of Compound I ($R_t$=60 min. ca. 37% of total radioactivity), and a discrete intermediate presumed to be the monobromo derivative Compound Ia ($R_t$=11.8 min, ca. 9%).

The filtrate solution was evaporated to near dryness with a stream of nitrogen, and the residue was dissolved in about 1.2 mL of the HPLC mobile phase. The solution was separated by HPLC as shown below, and the peaks corresponding to Compounds I and Ia and SB collected separately.

| HPLC Method | |
|---|---|
| Column | Altex Ultrasphere 10 mm I.D. × 25 cm |
| Mobile Phase | 70:30:0.1 water/acetonitrile/trifluoroacetic acid |
| Flow Rate | 5 mL/min |
| UV detection | 210 nm |
| Injection Volumes | 0.05–0.4 m: |
| Retention Times | 7.8 min Compound I |
| | 24 min Compound Ia |

The pooled Compound I fractions totaled 32 mL in volume and the radioactive concentration was 1.52 mCi/mL (total 48.6 m Ci). The pooled SB Compound Ia [$^3$H] fractions (totaling 10.1 mCi) were evaporated to dryness and the residue was transferred quantitatively into a glass vial using 3.8 mL of absolute ethanol for further analysis.

An 8 mL (12.2 mCi) portion of Compound I was evaporated to dryness in vacuo at <35° C., then redissolved in 0.5 mL of mobile phase. The whole volume was injected into the HPLC system described above, and the appropriate peak was collected. Evaporation of the collected eluate in vacuo at <35° C. and transfer of the yellow residue into a vial with absolute ethanol provided a solution (3.8 mL, 2.44 mCi/mL) of Compound I. The portion of this solution used for NMR analyses was first evaporated to dryness using stream of nitrogen then taken up in $CD_3OD$.

Analysis of 4-(4-Fluorophenyl)-2-(4-hydroxyphenyl-3,5-$t_2$)-5-(4-pyridyl)imidazole, Compound I.

| Radiochemical Purity by HPLC | |
|---|---|
| Method | |
| Column | Ultrasphere Octyl, 5 mm, 4.6 mm I.D. × 25 cm, Beckman |
| Mobile Phase | 350:150:0.5 (v/v/v) water/acetonitrile/trifluoroacetic acid |
| Flow Rate | 1.0 mL/min |
| Mass detection | UV at 210 nm |
| Radioactivity detection | Ramona-D radioactivity flow detector |
| Scintillator | Tru-Count (Tru-Lab Supply Co.) |
| Flow rate | 5.0 mL/min |
| Cell volume | 0.75 mL |
| Retention time | 7.7 min |
| Result | 98.7 |
| Radioactive Concentration by Scintillation Counting | |
| Method | |
| Scintillator | Ready Safe (Beckman Instruments, Inc.) |
| Instrument | TM Analytic model 6881 |
| Efficiency | Automated DPM calculation from quench curve |
| Result | 2.44 mCi/mL |
| Specific Activity by Mass Spectrometry | |
| Method | |
| Method | CI-MS, $NH_3$ reagent gas |
| Result | 20.0 Ci/mmol |
| | $^3$H Distribution: |
| | Unlabeled 44% |
| | Single Label 43% |
| | Double Label 13% |
| $^3$H NMR[9] | |
| Method | |
| Instrument | Brunker AM 400 |
| Experiment | Proton decoupled $^3$H NMR |
| | Proton non-decoupled $^3$H NMR |
| | Proton non-decoupled $^3$H NMR |
| Peak Referencing | Solvent Peak of methanol ∂ 3.3 |
| Solvent | Methanol-$d_4$ |
| Result | Tritium is incorporated exclusively on the carbon atoms ortho to aromatic hydroxyl group |

| Analytical Summary | |
|---|---|
| Assay | Result |
| Radiochemical purity determined by HPLC | 98.7% |
| Radioactivity concentration determined by scintillation counting | 2.44 mCi/mL |
| Specific activity determined by mass spectrometry | 20.0 Ci/mmol |
| $^3$H NMR | agrees with the proposed structure |

Representative compounds of Formula (I), Examples 1 to 97, all have demonstrated a positive inhibitory activity in this binding assay.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula (I):

$$\begin{array}{c} R_1 \diagdown \diagup R_2 \\ \phantom{R} N \\ \phantom{R_4} \diagdown \phantom{N} \diagup\!\!\!\!- R_3 \\ R_4 \diagup \diagdown N \end{array} \quad (I)$$

wherein:

$R_1$ is 4-pyridyl which is optionally substituted with one or two substituents each of which is independently selected from $C_{1-4}$ alkyl, halo, $C_{1-4}$ alkoxy, $C_{1-4}$ alkylthio, $NH_2$, mono- or di-$C_{1-6}$-alkylamino or N-heterocyclyl ring selected from pyrrolidine, piperidine, piperazine, morpholine, imidazolidine, and pyrazolidine;

$R_2$ is hydrogen;

n' is an integer having a value of 1 to 10;

m is 0, or the integer 1 or 2;

$R_3$ is Q—$(Y_1)_{t'}$;

Q is an phenyl;

t is an integer of 1 to 3;

Z is oxygen or sulfur;

n is 0 or an integer from 1 to 10;

$Y_1$ is independently selected from —$(CR_{10}R_{20})_nY_2$;

$Y_2$ is OH, —$NO_2$, —$S(O)_m'R_{11}$, —$S(O)_m'OR_8$, —$S(O)_m NR_8R_9$, —$NR_8R_9$, —$O(CR_{10}R_{20})_nNR_8R_9$, —$C(O)R_8$, —$CO_2R_8$, —$CO_2(CR_{10}R_{20})_n'CONR_8R_9$, —$ZC(O)R_8$, —CN, —$C(Z)NR_8R_9$, —$NR_{10}C(Z)R_8$, —$C(Z)NR_8OR_9$, —$NR_{10}C(Z)NR_8R_9$, —$NR_{10}S(O)_mR_{11}$, —$N(OR_{21})C(Z)NR_8R_9$, —$N(OR_{21})C(Z)R_8$, —$C(=NOR_{21})R_8$, —$NR_{10}C(=NR_{15})SR_{11}$, —$NR_{10}C(=NR_{15})NR_8R_9$, —$NR_{10}C(=CR_{14}R_{24})SR_{11}$, —$NR_{10}C(=CR_{14}R_{24})NR_8R_9$, —$NR_{10}C(O)C(O)$ $NR_8R_9$, $-NR_{10}C(O)C(O)OR_{10}$, $-C(=NR_{13})NR_8R_9$, $-C(=NOR_{13})NR_8R_9$, $-C(=NR_{13})ZR_{11}$, $-OC(Z)NR_8R_9$, $-NR_{10}S(O)_mCF_3$, $-NR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; provided that $Y_1$ may also be a halogen or $C_{1-5}$ alkyl when t=2 or 3;

m' is an integer having a value of 1 or 2;

$R_4$ is phenyl, naphth-1-yl or naphth-2-yl which is optionally substituted by one or two substituents, each of which is independently selected, and which, for a 4-phenyl, 4-naphth-1-yl or 5-naphth-2-yl substituent, is halo, cyano, $-C(Z)NR_7R_{17}$, $-C(Z)OR_{23}$, $-(CR_{10}R_{20})_m'''COR_{36}$, $SR_5$, $-SOR_5$, $-OR_{36}$, halo-substituted-$C_{1-4}$ alkyl, $C_{1-4}$ alkyl, $-ZC(Z)R_{36}$, $-NR_{10}C(Z)R_{23}$, or $-(CR_{10}R_{20})_m'''NR_{10}R_{20}$ and which, for other positions of substitution, is halo, cyano, $-C(Z)NR_{16}R_{26}$, $-C(Z)OR_8$, $-(CR_{10}R_{20})_m'''COR_8$, $-S(O)_mR_8$, $-OR_8$, halo-substituted-$C_{1-4}$ alkyl, $-C_{1-4}$ alkyl, $-(CR_{10}R_{20})_m'''NR_{10}C(Z)R_8$, $-NR_{10}S(O)_m'R_{11}$, $-NR_{10}S(O)_m'NR_7R_{17}$ $-ZC(Z)R_8$ or $-(CR_{10}R_{20})_m'NR_{16}R_{26}$;

wherein m" is 0 to 5 and m'" is 0 or 1;

$R_5$ is hydrogen, $C_{1-4}$ alkyl, $C_{2-4}$ alkenyl, $C_{2-4}$ alkynyl or $NR_7R_{17}$, excluding the moieties $-SR_5$ being $-SNR_7R_{17}$ and $-SOR_5$ being $-SOH$;

$R_7$ and $R_{17}$ is each independently selected from hydrogen or $C_{1-4}$ alkyl or $R_7$ and $R_{17}$ together with the nitrogen to which they are attached form a heterocyclic ring members which ring optionally contains an additional heteroatom selected from oxygen, selected from pyrrolidine, piperidine, piperazine, morpholine, imidazolidine, and pyrazolidine;

$R_8$ is hydrogen or $R_{11}$;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, or $R_8$ and $R_9$ may together with the nitrogen to which they are attached form a heterocyclic ring selected from pyrrolidine, piperidine, piperazine, morpholine, imidazolidine, and pyrazolidine;

$R_{10}$ and $R_{20}$ is each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl;

$R_{12}$ is hydrogen, $-C(Z)R_{13}$ or optionally substituted $C_{1-4}$ alkyl, optionally substituted aryl, optionally substituted aryl$C_{1-4}$ alkyl, or $S(O)_2R_{25}$;

$R_{13}$ is hydrogen, $C_{1-10}$ alkyl, $C_{3-7}$ cycloalkyl, aryl, aryl$C_{1-10}$ alkyl;

$R_{14}$ and $R_{24}$ is each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring selected from pyrrolidine, piperidine, piperazine, morpholine, imidazolidine, and pyrazolidine;

$R_{18}$ and $R_{19}$ is each independently selected from hydrogen, $C_{1-4}$ alkyl, substituted alkyl, optionally substituted aryl, optionally substituted arylalkyl or together $R_{18}$ and $R_{19}$ denote a double bonded oxygen or sulfur; wherein the alkyl, aryl and arylalkyl groups are optionally substituted by halogen, hydroxy, hydroxy substituted $C_{1-10}$alkyl, $C_{1-10}$ alkoxy, $S(O)m$ alkyl, (wherein m is 0, 1 or 2), $NR_7R_{17}$ group, $C_{1-10}$ alkyl, cycloalkyl, cycloalkyl alkyl, halosubstituted $C_{1-10}$ alkyl, optionally substituted aryl, optionally substituted arylalkyl, wherein these aryl moieties may also be substituted one to two times by halogen, hydroxy, hydroxy substituted alkyl, $C_{1-10}$ alkoxy, $S(O)_m$ alkyl, $NR_7R_{17}$ group, $C_{1-10}$ alkyl, or $CF_3$;

$R_{21}$ is hydrogen, a pharmaceutically acceptable cation, $C_{1-10}$ alkyl, $C_{3-7}$ cycloalkyl, aryl, aryl $C_{1-4}$ alkyl, aroyl, or $C_{1-10}$ alkanoyl;

$R_{22}$ is $R_{10}$ or $C(Z)-C_{1-4}$ alkyl;

$R_{23}$ is $C_{1-4}$ alkyl, halo-substituted-$C_{1-4}$ alkyl, or $C_{3-5}$ cycloalkyl;

$R_{36}$ is hydrogen or $R_{23}$;

$R_{25}$ is $C_{1-10}$ alkyl, $C_{3-7}$ cycloalkyl;

$R_{27}$ is hydrogen, cyano, $C_{1-4}$ alkyl, $C_{3-7}$ cycloalkyl, or aryl;

or a pharmaceutically acceptable salt thereof.

2. The compound according to claim 1, wherein the $R_1$4-pyridyl moiety is substituted by alkyl, amino, or mono- or di- $C_{1-6}$ alkylamino.

3. The compound according to claim 1 wherein $Y_2$ is OH, $-S(O)_mR_{11}$, $-S(O)_mNR_8R_9$, or $-NR_8R_9$.

4. The compound according to claim 1 wherein $R_4$ is optionally substituted phenyl, naphth-1-yl or naphth-2-yl wherein the 4-phenyl, 4-naphth-1-yl or 5-naphth-2-yl moiety are substituted by one or two substituents each independently selected from halogen, $-SR_5$, $-SOR_5$, $-OR_{36}$, or $-(CR_{10}R_{20})_m'''NR_{10}R_{20}$, and for other positions of substitution on these rings the substitution is halogen, $-S(O)_mR_8$, $-OR_8$, $-(CR_{10}R_{20})_m'''NR_{16}R_{26}$, $-NR_{10}C(Z)R_8$ and $-NR_{10}S(O)_mR_{11}$.

5. The compound according to claim 4 wherein the substituent in the 4-position for phenyl and naphth-1-yl and on the 5-position in naphth-2-yl is fluoro, chloro, $-SR_5$ or $-SOR_5$; and 3-position substitution for phenyl and naphth-1-yl is fluoro, chloro, $-OR_8$, amino, $-NHCO(C_{1-10}$ alkyl); and $-NR_{10}S(O)_mR_{11}$.

6. The compound according to claim 5 wherein $R_1$ is 4-pyridyl, or 2-alkyl-4-pyridyl.

7. The compound according to claim 3 wherein the $Y_2$ group is substituted in the 4-position of the phenyl ring.

8. The compound according to claim 1 wherein $Y_2$ is methylsulfinyl, ethylsulfinyl, methylsulfonyl, N,N-dimethylaminomethyl, N-benzyl-N-methylaminomethyl, N-morpholinomethyl, methanesulfonamido, sulphonamidomethyl, 5-methyl-4,5-dihydro-1,2,4-oxadiazol-3-yl or 5,5-dimethyl-4,5-dihydro-1,2,4-oxadiazol-3-yl.

9. The compound according to claim 1 which is:

2-(4-Cyanophenyl)-4-(4-fluorophenyl)-5-(4-pyridyl)-1H-imidazole;

4-(4-Fluorophenyl)-2-(4-hydroxyphenyl)-5-(4-pyridyl)-1H-imidazole;

4-[4-(4-Fluorophenyl)-5-(4-pyridyl)-1H-imidazol-2-yl] benzoic acid;

2-(4-Aminomethylphenyl)-4-(4-fluorophenyl)-5-(4-pyridyl)-1H-imidazole;

2-(3,5-Dibromo-4-hydroxyphenyl)-4-(4-fluorophenyl)-5-(4-pyridyl)-1H-imidazole;

Ethyl 4-[4-(4-Fluorophenyl)-5-(4-pyridyl)]-1H-imidazol-2-yl]-benzoate;

2-[3,5-Dimethyl-4-hydroxy(phenyl)]-4-(4-fluorophenyl)-5-(4-pyridyl)-1H-imidazole;

4-(4-Fluorophenyl)-2-(2-hydroxyphenyl)-5-(4-pyridyl)-1H-imidazole;

Methyl 4-[4-(4-fluorophenyl)-5-(4-pyridyl)-1H-imidazol-2-yl]-benzoate;

4-(4-Fluorophenyl)-2-(4-methylsulfonylphenyl)-5-(4-pyridyl)-1H-imidazole;

4-(4-Fluorophenyl)-2-(4-methylsulfinylphenyl)-5-(4-pyridyl)-1H-imidazole;

N,N-Dimethyl-4-[4-(4-fluorophenyl-5-(4-pyridyl)-1H-imidazol-2-yl]-benzamide;

2-[(4-N,N-Dimethyl)aminomethylphenyl]-4-(4-fluorophenyl)-5-(4-pyridyl)-1H-imidazole;

2-[4-(Dimethylamino)phenyl]-4-(4-fluorophenyl)-5-(4-pyridyl)-1H-imidazole;

2-[4-(3-Dimethylaminopropoxy)phenyl]-4-(4-fluorophenyl)-5-(4-pyridyl)-1H-imidazole;

4-(4-Fluorophenyl)-2-(4-nitrophenyl)-5-(4-pyridyl)-1H-imidazole;

N,N-Dimethyl-4-[2-(4-fluorophenyl)-5-(4-pyridyl)-1H-imidazol-2-yl]benzoyloxyacetamide;

2-(4-Aminophenyl)-4-(4-fluorophenyl)-5-(4-pyridyl)-1H-imidazole;

4-(4-Fluorophenyl)-2-(4-methanesulfonamidophenyl)-5-(4-pyridyl)-1H-imidazole;

4-[4-(4-Fluorophenyl)-5-(4-pyridyl)-1H-imidazol-2-yl]phenyl-sulfonamide;

N'-Cyano-N-4-[4-(fluorophenyl)-5-(4-pyridyl)-1H-imidazol-2-yl]benzylguanidine;

2-[4-(Methanesulfonamido)methylphenyl]-4-(4-fluorophenyl)-5-(4-pyridyl)-1H-imidazole;

2-(4-Amino-3-iodophenyl)-4-(4-fluorophenyl)-5-(4-pyridyl)-1H-imidazole;

N-Benzyl-N-methyl-4-[4-(4-fluorophenyl-5-(4-pyridyl)-1H-imidazol-2-yl]benzamide;

2-[4-(N-Benzyl-N-methyl)aminomethylphenyl]-4-(4-fluorophenyl)-5-(4-pyridyl)-1H-imidazole;

4-(3-Chlorophenyl)-2-(4-methylsulfinylphenyl)-5-(4-pyridyl)-1H-imidazole;

4-(4-Fluorophenyl)-2-(4-formamidomethylphenyl)-5-(4-pyridyl)-1H-imidazole;

4-[4-(4-Fluorophenyl)-5-(4-pyridyl)-1H-imidazol-2-yl]-benzohydroxamic acid;

O-Benzyl-4-[4-(4-Fluorophenyl)-5-(4-pyridyl)-1H-imidazol-2-yl]-benzohydroxamic acid;

4-[4-(4-Fluorophenyl)-5-(4-pyridyl)-1H-imidazol-2-yl]benzamidoxime;

N"-Methyl-N'-cyano-N-[4-(4-fluorophenyl)-5-(4-pyridyl)-1H-imidazol-2-yl]benzylguanidine;

4-(3-Methoxyphenyl)-2-(4-methylsulfinylphenyl)-5-(4-pyridyl)-1H-imidazole;

Morpholino-4-[4-(4-fluorophenyl)-5-(4-pyridyl)-1H-imidazol-2-yl]benzamide;

4-(4-Fluorophenyl)-5-[4-(2-methylpyridyl)]-2-(4-methylthiophenyl)-1H-imidazole;

4-(4-Fluorophenyl)-5-[4-(2-methylpyridyl)]-2-(4-methylsulfinylphenyl)-1H-imidazole;

4-(4-Fluorophenyl)-2-(4-Morpholinomethylphenyl)-5-(4-pyridyl)-1H-imidazole;

4-(4-Fluorophenyl)-2-(4-hydroxymethyl)-5-(4-pyridyl)-1H-imidazole;

4-[4-(4-Fluorophenyl)-5-(4-pyridyl)-1H-imidazol-2-yl]-benzaldehyde;

4-(2-Methoxyphenyl)-2-(4-methylsulfinylphenyl)-5-(4-pyridyl)-1H-imidazole;

3-[4-(4-Fluorophenyl)-5-(4-pyridyl)-1H-imidazol-2-yl]phenyl-5-methyl-4,5-dihydro-1,2,4-oxadiazole;

3-[4-(4-Fluorophenyl)-5-(4-pyridyl)-1H-imidazol-2-yl]phenyl-5-methyl-1,2,4-oxadiazole;

3-[4-(4-Fluorophenyl)-5-(4-pyridyl)-1H-imidazol-2-yl]phenyl-1,2,4-oxadiazol-5-(4H)-one;

3-[4-(4-Fluorophenyl)-5-(4-pyridyl)-1H-imidazol-2-yl]-phenyl-5,5-dimethyl-4,5-dihydro-1,2,4-oxadiazole;

4-(3-Methylthiophenyl)-2-(4-morpholinomethylphenyl)-5-(4-pyridyl)-1H-imidazole;

4-(3-Methylsulfinylphenyl)-2-(4-morpholinomethylphenyl)-5-(4-pyridyl)-1H-imidazole;

4-(3-Methanesulfonamidophenyl)-2-(4-methylsulfinylphenyl)-5-(4-pyridyl)-1H-imidazole;

2-(4-Ethylsulfinylphenyl)-4-(4-fluorophenyl)-5-(4-pyridyl)-1H-imidazole;

4-(4-Fluorophenyl)-2-[(4-(4-methyl-1-piperzinyl)-sulfonyl-phenyl]-5-(4-pyridyl)-1H-imidazole;

4-(4-Fluorophenyl)-2-[4-(N-methylmethanesulfonamido)-methylphenyl]-5-(4-pyridyl)-1H-imidazole;

4-(4-Fluorophenyl)-2-(3-methylsulfinylphenyl)-5-(4-pyridyl)-1H-imidazole or a pharmaceutically acceptable salt thereof.

10. The compound according to claim 9 which is 4-(4-Fluorophenyl)-2-(4-methylsulfinylphenyl)-5-(4-pyridyl)-1H-imidazole, or a pharmaceutically acceptable salt thereof.

11. A pharmaceutical composition comprising a compound according to claim 1 and a pharmaceutically acceptable carrier or diluent.

12. A pharmaceutical composition comprising a compound according to claim 9 and a pharmaceutically acceptable carrier or diluent.

13. A pharmaceutical composition comprising 4-(4-Fluorophenyl)-2-(4-methylsulfinylphenyl)-5-(4-pyridyl)-1H-imidazole, or a pharmaceutically acceptable salt thereof, and a pharmaceutically acceptable carrier or diluent.

\* \* \* \* \*